United States Patent
Donda et al.

(10) Patent No.: US 9,603,922 B2
(45) Date of Patent: Mar. 28, 2017

(54) MODULATION OF NKT CELL ACTIVITY WITH ANTIGEN-LOADED CD1D MOLECULES

(75) Inventors: Alena Donda, Auboranges (CH); Jean-Pierre Mach, Bellevue (CH); Kathrin Stirnemann, Zurich (CH)

(73) Assignee: VACCINEX, INC., Rochester, NY (US)

(*) Notice: Subject to any disclaimer, the term of this patent is extended or adjusted under 35 U.S.C. 154(b) by 687 days.

(21) Appl. No.: 12/034,737

(22) Filed: Feb. 21, 2008

(65) Prior Publication Data

US 2008/0254045 A1    Oct. 16, 2008

Related U.S. Application Data

(60) Provisional application No. 60/890,964, filed on Feb. 21, 2007.

(51) Int. Cl.
| | | |
|---|---|---|
| A61K 39/385 | (2006.01) | |
| A61K 39/39 | (2006.01) | |
| A61K 39/00 | (2006.01) | |
| C07K 16/32 | (2006.01) | |

(52) U.S. Cl.
CPC ............ *A61K 39/385* (2013.01); *A61K 39/39* (2013.01); *C07K 16/32* (2013.01); *A61K 2039/55516* (2013.01); *A61K 2039/55561* (2013.01); *A61K 2039/55572* (2013.01); *A61K 2039/55594* (2013.01); *A61K 2039/6018* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,690,915 A | 9/1987 | Rosenberg |
| 5,081,029 A | 1/1992 | Zarling et al. |
| 5,194,425 A | 3/1993 | Sharma et al. |
| 5,264,618 A | 11/1993 | Felgner et al. |
| 5,635,363 A | 6/1997 | Altman et al. |
| 5,679,347 A | 10/1997 | Porcelli et al. |
| 5,780,441 A | 7/1998 | Higa et al. |
| 5,849,716 A | 12/1998 | Akimoto et al. |
| 5,853,737 A | 12/1998 | Modlin et al. |
| 5,936,076 A | 8/1999 | Higa et al. |
| 6,015,884 A | 1/2000 | Schneck et al. |
| 6,162,609 A | 12/2000 | Hafler et al. |
| 6,238,676 B1 | 5/2001 | Porcelli et al. |
| 6,248,564 B1 | 6/2001 | Walter et al. |
| 6,531,453 B1 | 3/2003 | Taniguchi et al. |
| 6,548,067 B1 | 4/2003 | Seeman et al. |
| 6,682,741 B1 | 1/2004 | Ribaudo et al. |
| 6,747,010 B2 | 6/2004 | Taniguchi et al. |
| 6,881,828 B2 | 4/2005 | Edwards et al. |
| 7,273,852 B2 | 9/2007 | Tsuji et al. |
| 7,772,380 B2 | 8/2010 | Porcelli |
| 8,022,043 B2 | 9/2011 | Porcelli |
| 9,139,809 B2 | 9/2015 | Porcelli et al. |
| 9,371,352 B2 | 6/2016 | Porcelli et al. |
| 2002/0051783 A1 | 5/2002 | Savage |
| 2002/0071842 A1 | 6/2002 | Gumperz et al. |
| 2002/0155447 A1 | 10/2002 | Zauderer et al. |
| 2003/0157135 A1 | 8/2003 | Tsuji et al. |
| 2003/0166277 A1 | 9/2003 | Zauderer et al. |
| 2004/0091488 A1 | 5/2004 | Seeman et al. |
| 2004/0096429 A1 | 5/2004 | Savage |
| 2004/0127429 A1 | 7/2004 | Tsuji |
| 2004/0210037 A1 | 10/2004 | Zauderer et al. |
| 2005/0042218 A1 | 2/2005 | Zauderer |
| 2005/0112141 A1 | 5/2005 | Terman |
| 2005/0192248 A1 | 9/2005 | Tsuji et al. |
| 2006/0019246 A1 | 1/2006 | Tsuji et al. |
| 2006/0052316 A1 | 3/2006 | Porcelli |
| 2006/0074235 A1 | 4/2006 | Annoura et al. |
| 2006/0116331 A1 | 6/2006 | Jiang et al. |
| 2006/0148723 A1 | 7/2006 | Yamamura et al. |
| 2006/0211856 A1 | 9/2006 | Tsuji et al. |

(Continued)

FOREIGN PATENT DOCUMENTS

| | | |
|---|---|---|
| AU | B-39005/89 | 2/1990 |
| EP | 0 352 761 B1 | 10/1995 |

(Continued)

OTHER PUBLICATIONS

Tisch et al (PNAS 91: 437-438, 1994).*
Schwartz and Kipnis (The Neuroscientist, 8(5): 405-413, 2002).*
De St. Groth et al (Immunology and Cell Biology 2004, 82: 260-268).*
Kakimi et al (J. Exp. Med. 2000, 192: 921-930).*
Kawakami et al (Infect. Immun. 2001, 69: 213-220).*
Hong et al (Nature Med. 2001, 7: 1052-1056).*
Taniguchi et al (Nature Immunology, 2003 4(12): 1164-1165).*
Jackman et al (abstract of Crit. Rev. Immunol. 1999, 19(1): 49-63).*
Fujii et al (J. Exp. Med. 2003, 198(2): 267-279).*
Fujii et al (Nature Immunol. 2002, 3: 867-874).*
Chirmule et al (J. Immunol., 1995, 155: 917-924).*
Pathologyoutlines.com (Oct. 21, 2016).*
Balk, S.P., et al., "Isolation and characterization of a cDNA and gene coding for a fourth CD1 molecule," *Proc. Natl. Acad. Sci. U.S.A.* 86:252-256, National Academy of Sciences (1989).

(Continued)

*Primary Examiner* — Michael Szperka
*Assistant Examiner* — Marianne Dibrino
(74) *Attorney, Agent, or Firm* — Womble Carlyle Sandridge & Rice, LLP

(57) ABSTRACT

The invention is directed to methods of modulating an immune response in an animal, comprising administering a composition comprising one or more soluble CD1d complexes, in particular non-specific soluble CD1d complexes. Soluble CD1d complexes comprise a soluble CD1d polypeptide, a β2-microglobulin polypeptide, and a ceramide-like glycolipid antigen bound to the CD1d antigen binding groove, and in certain embodiments, an immunogen. The administration of compositions of the present invention affects the activity of CD1d-restricted NKT cells, and in particular, allows for multiple administrations without causing CD1d-restricted NKT cell anergy.

18 Claims, 8 Drawing Sheets

(56) References Cited

U.S. PATENT DOCUMENTS

| | | |
|---|---|---|
| 2006/0269540 A1 | 11/2006 | Robert et al. |
| 2007/0238673 A1 | 10/2007 | Porcelli |
| 2007/0287664 A1 | 12/2007 | Ralston et al. |
| 2007/0292418 A1 | 12/2007 | Fields et al. |
| 2008/0254045 A1 | 10/2008 | Donda |
| 2010/0183549 A1 | 7/2010 | Porcelli et al. |
| 2013/0164325 A1 | 6/2013 | Porcelli et al. |
| 2014/0227296 A1 | 8/2014 | Porcelli et al. |

FOREIGN PATENT DOCUMENTS

| | | |
|---|---|---|
| GB | 2 339 782 A | 2/2000 |
| WO | WO 93/10220 A1 | 5/1993 |
| WO | WO 94/24142 | 10/1994 |
| WO | WO 94/25610 A1 | 11/1994 |
| WO | WO 96/26962 A1 | 9/1996 |
| WO | WO 97/35991 A1 | 10/1997 |
| WO | WO 98/07441 A1 | 2/1998 |
| WO | WO 98/23627 | 6/1998 |
| WO | WO 98/44928 | 10/1998 |
| WO | WO 99/11775 A1 | 3/1999 |
| WO | WO 99/13095 A1 | 3/1999 |
| WO | WO 99/21572 A1 | 5/1999 |
| WO | WO 99/31241 A1 | 6/1999 |
| WO | WO 99/64464 A2 | 12/1999 |
| WO | WO 99/64597 A1 | 12/1999 |
| WO | WO 00/00156 A2 | 1/2000 |
| WO | WO 01/44296 A1 | 6/2001 |
| WO | WO 01/71005 A2 | 9/2001 |
| WO | WO 01/72995 | 10/2001 |
| WO | WO 01/78768 A2 | 10/2001 |
| WO | WO 01/90198 A1 | 11/2001 |
| WO | WO 02/27027 A2 | 4/2002 |
| WO | WO 03/009812 A2 | 2/2003 |
| WO | WO 03/016326 | 2/2003 |
| WO | WO 2004/028475 A2 | 4/2004 |
| WO | WO 2004/029206 A2 | 4/2004 |
| WO | WO 2004/072091 A1 | 8/2004 |
| WO | WO 2005/000348 A2 | 1/2005 |
| WO | WO 2006/026389 A2 | 3/2006 |
| WO | WO 2007/007946 A1 | 1/2007 |
| WO | WO 2008/133801 A1 | 11/2008 |
| WO | WO 2010/081026 A1 | 7/2010 |
| WO | WO 2012/006342 A1 | 1/2012 |
| WO | WO 2014/124245 | 8/2014 |

OTHER PUBLICATIONS

Bendelac, A., et al., "CD1 recognition by mouse NK1+ T lymphocytes," *Science* 268:863-865, American Association for the Advancement of Science (1995).

Benlagha, K., et al., "In vivo identification of glycolipid antigen-specific T cells using fluorescent CD1d tetramers," *J. Exp. Med.* 191:1895-1903, Rockefeller University Press (2000).

Carnaud, C., et al., "Cutting edge: Cross-talk between cells of the innate immune system: NKT cells rapidly activate NK cells," *J. Immunol.* 163:4647-4650, American Association of Immunologists (1999).

Dutronc, Y. and Porcelli, S.A., "The CD1 family and T cell recognition of lipid antigens," *Tissue Antigens* 60:337-353, International Booksellers Publishers (2002).

Eberl, G. and MacDonald, H.R., "Selective induction of NK cell proliferation and cytotoxicity by activated NKT cells," *Eur. J. Immunol.* 30:985-992, VCH Verlagsgesellschaft (2000).

Glick, M., et al., "Novel CD8+ T Cell Antagonists Based on $\beta_2$-Microglobulin," *J. Biol. Chem.* 277:20840-20846, The American Society for Biochemistry and Molecular Biology, Inc. (2002).

Gonzalez-Aseguinolaza, G., et al., "α-galactosylceramide-activated Valpha 14 natural killer T cells mediate protection against murine malaria," *Proc. Natl. Acad. Sci. U.S.A.* 15:8461-8466, National Academy of Sciences (2000).

Gumperz, J.E., et al., "Functionally distinct subsets of CD1d-restricted natural killer T cells revealed by CD1d tetramer staining," *J. Exp. Med.* 195:625-636, Rockefeller University Press (2002).

Hebert, A.M., et al., "Kinetics and Thermodynamics of $\beta$2-Microglobulin Binding to the α3 Domain of Major Histocompatibility Complex Class I Heavy Chain," *Biochem.* 40:5233-5242, American Chemical Society (2001).

Hemmi, H., et al., "Small anti-viral compounds activate immune cells via the TLR7 MyD88-dependent signaling pathway," *Nat. Immunol.* 3:196-200, Nature America Incorporated (2002).

Hermans, I.F., "Dendritic Cell Function Can Be Modulated through Cooperative Action of TLR Ligands and Invariant NKT Cells," *J. Immunol.* 178:2721-2729, The American Association of Immunologists, Inc. (Mar. 2007).

Hermans, I.F., et al., "NKT cells enhance CD4+ and CD8+ T cell responses to soluble antigen in vivo through direct interaction with dendritic cells," *J. Immunol.* 171:5140-5147, American Association of Immunologists (2003).

Hochman, J.H., et al., "Specific Associations of Fluorescent $\beta$-2-Microglobulin with Cell Surfaces. The Affinity of Different H-2 and HLA Antigens for $\beta$-2-Microglobulin," *J. Immunol.* 140:2322-2329, The American Association of Immunologists (1988).

Im, J.S., et al., "Direct measurement of antigen binding properties of CD1 proteins using fluorescent lipid probes," *J. Biol. Chem.* 279:299-310, American Society for Biochemistry and Molecular Biology (2004).

Kang, S.J. and Cresswell, P., "Saposins facilitate CD1d-restricted presentation of an exogenous lipid antigen to T cells," *Nat. Immunol.* 5:175-181, Nature America Incorporated (2004).

Karadimitris, A., et al., "Human CD1d-glycolipid tetramers generated by in vitro oxidative refolding chromatography," *Proc. Natl. Acad. Sci. U.S.A.* 98:3294-3298, National Academy of Sciences (2001).

Kawano, T., et al., "CD1d-restricted and TCR-mediated activation of valphal4 NKT cells by glycosylceramides," *Science* 278:1626-1629, American Association for the Advancement of Science (1997).

Kojo, S., et al., "Alternative splicing forms of the human CD1D gene in mononuclear cells," *Biochem. Biophys. Res. Commun.* 276:107-111, Academic Press (2000).

Kojo, S., et al., "Low expression levels of soluble CD1d gene in patients with rheumatoid arthritis," *J. Rheumatol.* 30:2524-2528, Journal of Rheumatology Publishing Company (2003).

Kono, K., et al., "Identification of HER2/*neu*-Derived Peptide Epitopes Recognized by Gastric Cancer-Specific Cytotoxic T Lymphocytes," *Int. J. Cancer* 78:202-208, Wiley-Liss, Inc. (1998).

Miyamoto, K., et al., "A synthetic glycolipid prevents autoimmune encephalomyelitis by inducing TH2 bias of natural killer T cells," *Nature* 413:531-534, Nature Publishing Group (2001).

Nagarajan, N.A., and Kronenberg, M., "Invariant NKT Cells Amplify the Innate Immune Response to Lipopolysaccharide," *J. Immunol.* 178:2706-2713, The American Association of Immunologists, Inc. (Mar. 2007).

Nishimura, T., et al., "The interface between innate and acquired immunity: glycolipid antigen presentation by CD1d-expressing dendritic cells to NKT cells induces the differentiation of antigen-specific cytotoxic T lymphocytes," *Int. Immunol.* 12:987-994, Oxford University Press (2000).

Parekh, V.V., et al., "Glycolipid antigen induces long-term natural killer T cell anergy in mice," *J. Clin. Invest.* 115:2572-2583, American Society for Clinical Investigation (2005).

Parekh, V.V., et al., "The In Vivo Response of Invariant Natural Killer T Cells to Glycolipid Antigens," *Int. Rev. Immunol.* 26:31-48, Taylor & Francis (Jan.-Apr. 2007).

Parham, P., et al., "Carbohydrate Moiety of HLA Antigens," *J. Biol. Chem.* 252:7555-7567, The American Society of Biological Chemists, Inc. (1977).

Rongcun, Y., et al., "Identification of New HER2/neu-Derived Peptide Epitopes That Can Elicit Specific CTL Against Autologous and Allogenic Carcinomas and Melanomas," *J Immunol.* 163:1037-1044, The American Association of Immunologists (1999).

Sege, K., et al., "Role of $\beta$2-microglobulin in the intracellular processing of HLA antigens," *Biochemistry* 20:4523-4530, American Chemical Society (1981).

(56) References Cited

OTHER PUBLICATIONS

Silk, J.D., et al., "Utilizing the adjuvant properties of CD1d-dependent NK T cells in T cell-mediated immunotherapy," *J. Clin. Invest.* 114:1800-1811, American Society for Clinical Investigation (2004).
Smyth, M.J., et al., "Sequential production of interferon-gamma by NK1.1(+) T cells and natural killer cells is essential for the antimetastatic effect of α-galactosylceramide," *Blood* 99:1259-1266, American Society of Hematology (2002).
Smyth, M.J., et al., "Sequential activation of NKT cells and NK cells provides effective innate immunotherapy of cancer," *J. Exp. Med.* 201:1973-1985, Rockefeller University Press (2005).
Stirnemann, K., et al., "Sustained activation and tumor targeting of NKT cells using a CD1d-anti-HER2-scFv fusion protein induce antitumor effects in mice," *J. Clin. Invest.* 118:994-1005, American Society for Clinical Investigation (Mar. 2008).
Stronge, V.S., et al., "A closer look at CD1d molecules: new horizons in studying NKT cells," *Trends Immunol.* 28:455-462, Elsevier Science Ltd. (Oct. 2007).
Van Kaer, L., "NKT cells: T lymphocytes with innate effector functions," *Curr. Opin. Immunol.* 19:354-364,Elsevier Ltd. (Jun. 2007).
Whitman, M.C., et al., "The isolated major histocompatibility complex class I α3 domain binds β2m and CD8αα dimers," *Mol. Immunol.* 37:141-149, Elsevier Science Ltd. (2000).
Zeng, Z., et al., "Crystal structure of mouse CD1: An MHC-like fold with a large hydrophobic binding groove," *Science* 277:339-345, American Association for the Advancement of Science (1997).
Zhang, H-F., et al., "Targeting of functional antibody-CD59 fusion proteins to a cell surface," *J. Clin. Invest.* 103:55-61, The American Society for Clinical Investigation (1999).
Zhu, X., et al., "A recombinant single-chain human class II MHC molecule (HLA-DR1) as a covalently linked heterotrimer of α chain, β chain, and antigenic peptide, with immunogenicity in vitro and reduced affinity for bacterial superantigens," *Eur. J. Immunol* 27:1933-1941, Verlagsgesellschaft (1997).
Dialog File 351, Accession No. 3301784, Derwent WPI English language abstract for EP 0 133 988, cited on Form PTO/SB/08A as document FP1, 4 pages (Mar. 13, 1985).
NCBI Entrez, GenBank Report, Accession No. P01885 (Entry Date 1993), 3 pages.
NCBI Entrez, GenBank Report, Accession No. P23043 (Entry Date 1993), 3 pages.
NCBI Entrez, GenBank Report, Accession No. NP 004039 (Entry Date 1999), 3 pages.
NCBI Entrez, GenBank Report, Accession No. NP 001757 (Entry Date 1999), 8 pages.
NCBI Entrez, GenBank Report, Accession No. NP 058775 (Entry Date 2000), 5 pages.
NCBI Entrez, GenBank Report, Accession No. NP 031665 (Entry Date 2000), 3 pages.
NCBI Entrez, GenBank Report, Accession No. NP 033865 (Entry Date 2000), 3 pages.
NCBI Entrez, GenBank Report, Accession No. NP 036644 (Entry Date 2000), 3 pages.
NCBI Entrez, GenBank Report, Accession No. O62848 (Entry Date 2001), 3 pages.
NCBI Entrez, GenBank Report, Accession No. Q29422 (Entry Date 2001), 3 pages.
NCBI Entrez, GenBank Report, Accession No. NP 999143 (Entry Date 2004), 2 pages.
NCBI Entrez, GenBank Report, Accession No. NP 001009284 (Entry Date 2005), 2 pages.
NCBI Entrez, GenBank Report, Accession No. NP 001009066 (Entry Date 2005), 2 pages.
Office Action mailed Aug. 31, 2009, in U.S. Appl. No. 10/529,221, Robert, B., et al., filed Jun. 30, 2006.
Office Action mailed Jul. 8, 2010 , in U.S. Appl. No. 10/529,221, Robert, B., et al., filed Jun. 30, 2006.

Abastado, J., et al., "Dimerization of Soluble Major Histocompatibility Complex-Peptide Complexes is Sufficient for Activation of T Cell Hybridoma and Induction of Unresponsiveness," *J. Exp. Med.*, 1995, vol. 182, pp. 439-447.
Abdel-Wahab, Z., et al., "Human Dendritic Cells, Pulsed with either Melanoma Tumor Cell Lysates or the gp100 Peptide$_{(280-288)}$, Induce Pairs of T-Cell Cultures with Similar Phenotype and Lytic Activity," *Cellular Immunology*, 1998, vol. 186, pp. 63-74.
Alexander, J., et al., "Recognition of a Novel Naturally Processed, A2 Restricted, HCV-NS4 Epitope Triggers IFN-gamma Release in Absence of Detectable Cytopathicity," *Human Immunology*, 1998, vol. 59, pp. 776-782.
Alexander, M., et al., "Generation of tumor-specific cytolytic T lymphocytes from peripheral blood of cervical cancer patients by in vitro stimulation with a synthetic human papillomavirus type 16 E7 epitope," *Am. J. Obstet. Gynecol.*, 1996, vol. 175(6), pp. 1586-1593.
Altman, J., et al., "Phenotypic Analysis of Antigen-Specific T Lymphocytes," *Science*, 1996, vol. 274, pp. 94-96.
Battegay, M., et al., "Patients with Chronic Hepatitis C Have Circulating Cytotoxic T Cells Which Recognize Hepatitis C Virus-Encoded Peptides Binding to HLA-A2.1 Molecules," *Journal of Virology*, 1995, vol. 69(4), pp. 2462-2470.
Beaudoin, L., et al., "NKT Cells Inhibit the Onset of Diabetes by Impairing the Development of Pathogenic T Cells Specific for Pancreatic β Cells," *Immunity*, 2002, vol. 17, pp. 725-736.
Bedzyk, W., et al., "Immunological and Structural Characterization of a High Affinity Anti-fluorescein Single-chain Antibody," *The Journal of Biological Chemistry*, 1990, vol. 265(30), pp. 18615-18620.
Bertoletti, A., et al., "Molecular Features of the Hepatitis B Virus Nucleocapsid T-Cell Epitope 18-27: Interaction with HLA and T-Cell Receptor," *Hepatology*, 1997, vol. 26(4), pp. 1027-1034.
Bocchia, M., et al., "Specific Human Cellular Immunity to bcr-abl Oncogene-Derived Peptides," *Blood*, 1996, vol. 87(9), pp. 3587-3592.
Boitel, B., et al., "Strong Similarities in Antigen Fine Specificity Among *DRB1* *1302*-Restricted Tetanus Toxin tt830-843-Specific TCRs in Spite of Highly Heterogeneous CDR3," *The Journal of Immunology*, 1995, vol. 154, pp. 3245-3255.
Boniface, J., et al., "Initiation of Signal Transduction through the T Cell Receptor Requires the Peptide Multivalent Engagement of MHC Ligands," *Immunity*, 1998, vol. 9, pp. 459-466.
Bonish, B., et al., "Overexpression of CD1d by Keratinocytes in Psoriasis and CD1d-Dependent IFN-γ Production by NK-T Cells," *The Journal of Immunology*, 2000, vol. 165, pp. 4076-4085.
Brinckerhoff, L., et al., "Terminal Modifications Inhibit Proteolytic Degradation of an Immunogenic MART-1$_{27-35}$ Peptide: Implications for Peptide Vaccines," *Int. J. Cancer*, 1999, vol. 83, pp. 326-334.
Brusic, V., et al., "Prediction of MHC class II-binding peptides using an evolutionary algorithm and artificial neural network," *Bioinformatics*, 1998, vol. 14(2), pp. 121-130.
Burrows, G., et al., "Two-Domain MHC Class II Molecules Form Stable Complexes with Myelin Basic Protein 69-89 Peptide That Detect and Inhibit Rat Encephalitogenic T Cells and Treat Experimental Autoimmune Encephalomyelitis," *The Journal of Immunology*, 1988, vol. 161, pp. 5987-5996.
Casares, S., et al., "Antigen-specific Signaling by a Soluble, Dimeric Peptide/Major Histocompatibility Complex Class II/Fc Chimera Leading to T Helper Cell Type 2 Differentiation," *J Exp. Med.*, 1999, vol. 190(4), pp. 543-553.
Castelli, C., et al., "Novel HLA-Cw8-Restricted T Cell Epitopes Derived from Tyrosinase-Related Protein-2 and gp100 Melanoma Antigens," *The Journal of Immunology*, 1999, vol. 162, pp. 1739-1748.
Celis, E., et al., "Identification of Potential CTL Epitopes of Tumor-Associated Antigen MAGE-1 for Five Common HLA-A Alleles," *Molecular Immunology*, 1994, vol. 31(18), pp. 1423-1430.
Chaux, P., et al., "Identification of MAGE-3 Epitopes Presented by HLA-DR Molecules to CD4[+] T Lymphocytes," *J. Exp. Med.*, 1999, vol. 189(5), pp. 767-777.

(56) References Cited

OTHER PUBLICATIONS

Chen, H., et al., "Cultured NK1.1+CD4+ T Cells Produce Large Amounts of IL-4 and IFN-γ Upon Activation by Anti-CD3 or CD1," *The Journal of Immunology*, 1997, vol. 159, pp. 2240-2249.

Chikamatsu, K., et al., "Generation of Anti-p53 Cytotoxic T Lymphocytes from Human Peripheral Blood Using Autologous Dendritic Cells," *Clinical Cancer Research*, 1999, vol. 5, pp. 1281-1288.

Cochran, J., et al., "The Relationship of MHC-Peptide Binding and T Cell Activation Probed Using Chemically Defined MHC Class II Oligomers," *Immunity*, 2000, vol. 12, pp. 241-250.

Cormier, J., et al., "Heterogeneous Expression of Melanoma-Associated Antigens and HLA-A2 in Metastatic Melanoma In Vivo," *Int. J. Cancer*, 1998, vol. 75, pp. 517-524.

Cui, J., et al., "Requirement for $V_\alpha 14$ NKT Cells in IL-12-Mediated Rejection of Tumors," *Science*, 1997, vol. 278, pp. 1623-1626.

Dal Porto, J., et al., "A soluble divalent class I major histocompatibility complex molecule inhibits alloreactive T cells at nanomolar concentrations," *Proc. Natl. Acad. Sci. USA*, 1993, vol. 90, pp. 6671-6675.

Daniel, S., et al., "Relationship Between Peptide Selectives of Human Transporters Associated with Antigen Processing and HLA Class I Molecules," *The Journal of Immunology*, 1998, vol. 161, pp. 617-624.

De Backer, O., et al., "Characterization of the *GAGE* Genes That Are Expressed in Various Human Cancers and in Normal Testis," *Cancer Research*, 1999, vol. 59, pp. 3157-3165.

Diepolder, H., et al., "Immunodominant CD4+T-Cell Epitope within Nonstructural Protein 3 in Acute Hepatitis C Virus Infection," *Journal of Virology*, 1997, vol. 71(8), pp. 6011-6019.

Doolan, D., et al., "Degenerate Cytotoxic T Cell Epitopes from P. falciparum Restricted by Multiple HLA-A and HLA-B Supertype Alleles," *Immunity*, 1997, vol. 7, pp. 97-112.

Esser, S., et al., "Vascular endothelial growth factor induces VE-cadherin tyrosine phosphorylation in endothelial cells," *Journal of Cell Science*, 1998, vol. 111, pp. 1853-1865.

Exley, M., et al., "Requirements for CD1d Recognition by Human Invarient $V\alpha24^+$ CD4$^-$ CD8$^-$ T Cells," *J. Exp. Med.*, 1997, vol. 186(1), pp. 109-120.

Fayen, J., et al., "Class I MHC Alpha 3 Domain Can Function As an Independent Structural Unit to Bind CD8α," *Molecular Immunology*, 1995, vol. 32(4), pp. 267-275.

Fleischhauer, K., et al., "Functional Heterogeneity of HLA-A*02 Subtypes Revealed by Presentation of a MAGE-3-Encoded Peptide to Cytotoxic T Cell Clones," *The Journal of Immunology*, 1997, vol. 159, pp. 2513-2521.

Gotch, F., et al., "Cytotoxic T lymphocytes recognize a fragment of influenza virus matrix protein in association with HLA-A2," *Nature*, 1987, vol. 326, pp. 881-882.

Greten, T., et al., "Direct visualization of antigen-specific T cells: HTLV-1 Tax11-19-specific CD8+ T cells are activated in peripheral blood and accumulate in cerebrospinal fluid from HAM/TSP patients," *Proc. Natl. Acad. Sci. USA*, 1998, vol. 95, pp. 7568-7573.

Hamad, A., et al., "Potent T Cell Activation with Dimeric Peptide-Major Histocompatibility Complex Class II Ligand: The Role of CD4 Coreceptor," *J. Exp. Med.*, 1998, vol. 188(9), pp. 1633-1640.

Harbury, P., et al., "A Switch Between Two-, Three-, and Four-Stranded Coiled Coils in GCN4 Leucine Zipper Mutants," *Science*, 1993, vol. 262, pp. 1401-1407.

Harvill, E., et al., "In Vivo Properties of an IgG3-IL-2 Fusion Protein," *The Journal of Immunology*, 1996, vol. 157, pp. 3165-3170.

Heathcote, J., et al., "A Pilot Study of the CY-1899 T-Cell Vaccine in Subjects Chronically Infected with Hepatitis B Virus," *Hepatology*, 1999, vol. 30(2), pp. 531-536.

Hoffman, P., et al., "Large scale in vitro expansion of polyclonal human CD4+CD25$^{high}$ regulatory T cells," *Blood*, 2004, vol. 104(3), pp. 895-903.

Höllsberg, P., et al., "Differential activation of proliferation and cytotoxicity in human T-cell lymphotropic virus type I Tax-specific CD8 T cells by an altered peptide ligand," *Proc. Natl. Acad. Sci. USA*, 1995, vol. 92, pp. 4036-4040.

Illés, Z., et al., "Differential Expression of NK T Cell $V\alpha24J\alpha Q$ Invariant TCR Chain in the Lesions of Multiple Sclerosis and Chronic Inflammatory Demyelinating Polyneuropathy," *The Journal of Immunology*, 2000, vol. 164, pp. 4375-4381.

Jahng, A., et al., "Activation of Natural Killer T Cells Potentiates or Prevents Experimental Autoimmune Encephalomyelitis," *J. Exp. Med.*, 2001, vol. 194(12), pp. 1789-1799.

Kawakami, K., et al., "Activation of $V\alpha14^+$ Natural Killer T Cells by α-Galactosylceramide Results in Development of Th1 Response and Local Host Resistance in Mice Infected with *Cryptococcus neoformans*," *Infection and Immunity*, 2001, vol. 69(1), pp. 213-220.

Kawashima, I., et al., "Identification of GP100-Derived, Melanoma-Specific Cytotoxic T-Lymphocyte Epitopes Restricted by HLA-A3 Supertype Molecules by Primary In Vitro Immunization with Peptide-Pulsed Dendritic Cells," *Int. J. Cancer*, 1998, vol. 78, pp. 518-524.

Kawashima, I., et al., "Identification of HLA-A3-restriction Cytotoxic T Lymphocyte Epitopes from Carcinoembryonic Antigen and HER-2/*neu* by Primary in Vitro Immunization with Peptide-pulsed Dendritic Cells," *Cancer Research*, 1999, vol. 59, pp. 431-435.

Kim, J., et al., "Determinants of T Cell Reactivity to the *Mycobacterium leprae* GroES Homologue," *The Journal of Immunology*, 1997, vol. 159, pp. 335-343.

Kita, H., et al., "Quantitation and Phenotypic Analysis of Natural Killer T Cells in Primary Biliary Cirrhosis Using a Human CD1d Tetramer," *Gastroenterology*, 2002, vol. 123, pp. 1031-1043.

Kobayashi, E., et al., "KRN7000, A Novel Immunomodulator, and Its Antitumor Activities," *Oncology Research*, 1995, vol. 7(10/11), pp. 529-534.

Kundu, S., et al., "Role of Preimmunization Virus Sequences in Cellular Immunity in HIV-Infected Patients during HIV Type 1 MN Recombinant gp160 Immunization," *AIDS Research and Human Retroviruses*, 1998, vol. 14(18), pp. 1669-1678.

Lachman, L., et al., Chapter 29, "Cytokine-Containing Liposomes as Adjuvants for Subunit Vaccines," 1995, *Vaccine Design: The Subunit and Adjuvant Approach*, Powell, MF and Newman, MJ, eds, Plenum Press, New York, NY, pp. 659-671.

Lee, A., et al., "Novel synthesis of α-galactosyl-ceramides and confirmation of their powerful NKT cell agonist activity," *Carbohydrate Research*, 2006, vol. 341, pp. 2785-2798.

Lee, P., et al., "Distinct Functional Lineages of Human $V\alpha24$ Natural Killer T Cells," *J. Exp. Med.*, 2002, vol. 195(5), pp. 637-641.

Livingston, B., et al., "The Hepatitis B Virus-Specific CTL Responses Induced in Humans by Lipopeptide Vaccination Are Comparable to Those Elicited by Acute Viral Infection," *The Journal of Immunology*, 1997, vol. 159, pp. 1383-1392.

Manici, S., et al., "Melanoma Cells Present a MAGE-3 Epitope to CD4+ Cytotoxic T Cells in Association with Histocompatibility Leukocyte Antigen DR11," *J. Exp. Med.*, 1999, vol. 189(5), pp. 871-876.

Matsuda, J., et al., "Tracking the Response of Natural Killer T Cells to a Glycolipid Antigen Using CD1d Tetramers," *J. Exp. Med.*, 2000, vol. 192(5), pp. 741-753.

Morrison, S., et al., "Production and Characterization of Genetically Engineered Antibody Molecules," *Clin. Chem.*, 1988, vol. 34(9), pp. 1668-1675.

Mottez, E., et al., "Cells Expressing a Major Histocompatibility Complex Class I Molecule with a Single Covalently Bound Peptide are Highly Immunogenic," *J. Exp. Med.*, 1995, vol. 181, pp. 493-502.

Naumov, Y., et al., "Activation of CD1d-restricted T Cells protects NOD mice from developing diabetes by regulating dendritic cell subsets," *PNAS*, 2001, vol. 98(24), pp. 13838-13843.

Nukaya, I., et al., "Identification of HLA-A24 Epitope Peptides of Carcinoembryonic Antigen Which Induce Tumor-Reactive Cytotoxic T Lymphocyte," *Int. J Cancer*, 1999, vol. 80, pp. 92-97.

(56) References Cited

OTHER PUBLICATIONS

Ogg, G., et al., "Sensitization of tumour cells to lysis by virus-specific CTL using antibody-targeted MHC class I/peptide complexes," *British Journal of Cancer*, 2000, vol. 82(5), pp. 1058-1062.
Pack, P., et al., "Tetravalent Miniantibodies with High Avidity Assembling in *Escherichia coli*," *J. Mol. Biol.*, 1995, vol. 246, pp. 28-34.
Parker, K., et al., "Subunit Interactions of Class I Histocompatibility Antigens," *Biochemistry*, 1985, vol. 24, pp. 5543-5550.
Parkhurst, M., et al., "Identification of a Shared *HLA-A*0201*-restricted T-Cell Epitope from the Melanoma Antigen Tyrosinase-related Protein 2 (TRP2)," *Cancer Research*, 1998, vol. 58, pp. 4895-4901.
Peiper, M., et al., "Pancreatic Cancer Associated Ascites-Derived CTL Recognize a Nine-Amino-Acid Peptide GP2 Derived from HER2/neu," *Anticancer Research*, 1999, vol. 19, pp. 2471-2476.
Penichet, M., et al., "An Antibody-Avidin Fusion Protein Specific for the Transferrin Receptor Serves as a Delivery Vehicle for Effective Brain Targeting: Initial Applications in Anti-HIV Antisense Drug Delivery to the Brain," *The Journal of Immunology*, 1999, vol. 163, pp. 4421-4426.
Ramakrishna, V., et al., "Generation and Phenotypic Characterization of New Human Ovarian Cancer Cell Lines With the Identification of Antigens Potentially Recognizable by HLA-Restricted Cytotoxic T Cells," *Int. J Cancer*, 1997, vol. 73, pp. 143-150.
Reinhardt, C., et al., "Elevated frequencies of natural killer T lymphocytes in myasthenia gravis," *Neurology*, 1999, vol. 52, pp. 1485-1487.
Ressing, M., et al., "Human CTL Epitopes Encoded by Human Papillomavirus Type 16 E6 and E7 Identified Through In Vivo and In Vitro Immunogenicity Studies of HLA-A*0201-Binding Peptides," *The Journal of Immunology*, 1995, vol. 154, pp. 5934-5943.
Rivoltini, L., et al., "A Superagonist Variant of Peptide MART1/Melan $A_{27-35}$ Elicits Anti-Melanoma CD8$^+$ T Cells with Enhanced Functional Characteristics: Implication for More Effective Immunotherapy," *Cancer Research*, 1999, vol. 59, pp. 301-306.
Robert, B., et al., Redirecting anti-viral CTL against cancer cells by surface targeting of monomeric MHC class I-viral peptide conjugated to antibody fragments, *Cancer Immunity*, 2001, vol. 1, p. 2.
Rötzschke, O., et al., "Conformational variants of class II MHC/peptide complexes induced by N- and C-terminal extensions of minimal peptide epitopes," *Proc. Natl. Acad. Sci. USA*, 1999, vol. 96, pp. 7445-7450.
Salazar-Onfray, F., et al., Synthetic Peptides Derived from the Melanocyte-stimulating Hormone Receptor MC1R Can Stimulate HLA-A2-restricted Cytotoxic T Lymphocytes That Recognize Naturally Processed Peptides on Human Melanoma Cells, *Cancer Research*, 1997, vol. 57, pp. 4348-4355.
Salter, R., et al., "A binding site for the T-cell co-receptor CD8 on the $\alpha_3$ domain of HLA-A2," *Nature*, 1990, vol. 345, pp. 41-46.
Saubermann, L., et al., "Activation of Natural KillerT Cells by $\alpha$-Galactosylceramide in the Presence of CD1d Provides Protection Against Colitis in Mice," *Gastroenterology* 2000, vol. 119, pp. 119-128.
Schmitt, L., et al., "Catalysis of peptide dissociation from class II MHC-peptide complexes," *Proc. Natl. Acad. Sci. USA*, 1999, vol. 96, pp. 6581-6586.
Schnell, S., et al., "Retrovirally Transduced Mouse Dendritic Cells Require CD4$^+$ T Cell Help to Elicit Antitumor Immunity: Implications for the Clinical Use of Dendritic Cells," *The Journal of Immunology*, 2000, vol. 164, pp. 1243-1250.
Sharif, S., et al., "Activation of natural killer T cells by $\alpha$-galactosylceramide treatment prevents the onset and recurrence of autoimmune Type 1 diabetes," *Nature Medicine*, 2001, vol. 7(9), pp. 1057-1062.
Sharif, S., et al., "Regulation of autoimmune disease by natural killer T Cells," *J Mol Med*, 2002, vol. 80, pp. 290-300.

Shi, F., et al., "Germ line deletion of the CD1 locus exacerbates diabetes in the NOD mouse," *PNAS*, 2001, vol. 98(12), pp. 6777-6782.
Sidney, J., et al., "Practical, biochemical and evolutionary implications of the discovery of HLA class I supermotifs," *Immunology Today*, 1996, vol. 17(6), pp. 261-266.
Sidney, J., et al., "Majority of Peptides Binding HLA-A*0201 With High Affinity Crossreact With Other A2-Supertype Molecules," *Human Immunology*, 2001, vol. 62, pp. 1200-1216.
Singh, A., et al., "Natural Killer T Cell Activation Protects Mice Against Experimental Autoimmune Encephalomyelitis," *J. Exp. Med.*, 2001, vol. 194(12), pp. 1801-1811.
Smyth, M., et al., "NKT cells—conductors of tumor immunity?," *Curr Opin Immunol*, 2002, vol. 14, pp. 165-171.
Springer, T., et al., "Detergent-soluble HLA antigens contain a hydrophyilic region at the COOH-terminus and a penultimate hydrophobic region," *Proc. Natl. Acad. Sci. USA*, 1976, vol. 73(7), pp. 2481-2485.
Steller, M., et al., "Cell-mediated Immunological Responses in Cervical and Vaginal Cancer Patients Immunized with a Lipidated Epitope of Human Papillomavirus Type 16 E7," *Clinical Cancer Research*, 1998, vol. 4, pp. 2103-2109.
Stober, D., et al., "NKT Cells Provide Help for Dendritic Cell-Dependent Priming of MHC Class I-Restricted CD8$^+$T Cells In Vivo," *The Journal of Immunology*, 2003, vol. 170, pp. 2540-2548.
Sumida, T., et al., "Selective Reduction of T Cells Bearing Invariant $V\alpha 24J\alpha Q$ Antigen Receptor in Patients with Systemic Sclerosis," *J. Exp. Med.*, 1995, vol. 182, pp. 1163-1168.
Tahir, S., et al., "Loss of IFN-$\gamma$ Production by Invariant NK T Cells in Advanced Cancer," *The Journal of Immunology*, 2001, vol. 167, pp. 4046-4050.
Takahashi, T., et al., "707-AP Peptide Recognized by Human Antibody Induces Human Leukocyte Antigen A2-restricted Cytotoxic T Lymphocyte Killing of Melanoma," *Clinical Cancer Research*, 1997, vol. 3, pp. 1363-1370.
Takahashi, T., et al., "Cytotoxic T lymphocytes that recognize decameric peptide sequences of retinoblastoma binding protein 1 (RBP-1) associated with human breast cancer," *British Journal of Cancer*, 1999, vol. 81(2), pp. 342-349.
Takeda, K., et al., "Relative contribution of NK and NKT cells to the anti-metastatic activities of IL-12," *International Immunology*, 2000, vol. 12(6), pp. 909-914.
Tanzarella, S., et al., "Identification of a Promiscuous T-Cell Epitope Encoded by Multiple Members of the *MAGE* Family" *Cancer Research*, 1999, vol. 59, pp. 2668-2674.
Timmerman, J., et al., "Dendritic Cell Vaccines for Cancer Immunotherapy," *Annu. Rev. Med.*, 1999, vol. 50, pp. 507-529.
Turkewitz, A., et al., "Large-Scale Purification of Murine I-A$^K$ and I-E$^K$ Antigens and Characterization of the Purified Proteins," *Molecular Immunology*, 1983, vol. 20(11), pp. 1139-1147.
Turner, M., et al., "Purification of Papain-solubilized Histocompatibility Antigens from a Cultured Human Lymphoblastoid Line, RPMI 4265," *The Journal of Biological Chemistry*, 1975, vol. 250(12), pp. 4512-4519.
Valmori, D., et al., "Analysis of MAGE-3-specific Cytolytic T Lymphocytes in Human Leukocyte Antigen-A2 Melanoma Patients," *Cancer Research*, 1997, vol. 57, pp. 735-741.
Valmori, D., et al., "Diversity of the Fine Specificity Displayed by HLA-A*0201—Restricted CTL Specific for the Immunodominant Melan-A/MART-1 Antigenic Peptide," *The Journal of Immunology*, 1998, vol. 161, pp. 6956-6962.
Valmori, D., et al., "Analysis of the Cytolytic T Lymphocyte Response of Melanoma Patients to the Naturally HLA-A*0201—associated Tyrosinase Peptide 368-376," *Cancer Research*, 1999, vol. 59, pp. 4050-4055.
Van Der Vliet, H., et al., "Circulating $V\alpha 24^+$ $V\beta 11^+$ NKT Cell Numbers are Decreased in a Wide Variety of Diseases That Are Characterized by Autoreactive Tissue Damage," *Clinical Immunology*, 2001, vol. 100(2), pp. 144-148.
Wang, B., et al., "CD1-restricted NK T Cells Protect Nonobese Diabetic Mice from Developing Diabetes," *J. Exp. Med.*, 2001, vol. 194(3), pp. 313-319.

(56) References Cited

OTHER PUBLICATIONS

Wang, R., et al., "Recognition of an Antigenic Peptide Derived from Tyrosinase-Related Protein-2 by CTL in the Context of HLA-A31 and—A33," *The Journal of Immunology*, 1998, vol. 160, pp. 890-897.

Wilson, M., et al., "Immunotherapy with ligands of natural killer T cells," *TRENDS in Molecular Medicine*, 2002, vol. 8(5), pp. 225-231.

Wizel, B., et al., "HLA-A2-Retricted Cytotoxic T Lymphocyte Responses to Multiple *Plasmodium falciparum* Sporozoite Surface Protein 2 Epitopes in Sporozoite-Immunized Volunteers," *The Journal of Immunology*, 1995, vol. 155, pp. 766-775.

Wizel, B., et al., "Human Infection with *Trypanosoma cruzi* Induces Parasite Antigen-Specific Cytotoxic T Lymphocyte Responses," *J. Clin. Invest.*, 1998, vol. 102(5), pp. 1062-1071.

Zarour, H., et al., "Melan-A/MART-1$_{51-73}$ represents an immunogenic HLA-DR4-restricted epitope recognized by melanoma-reactive CD4$^+$ T cells," *PNAS*, 2000, vol. 97(1), pp. 400-405.

Zarutskie, J., et al., "A Conformational Change in the Human Major Histocompatibility Complex Protein HLA-DR1 Induced by Peptide Binding," *Biochemistry*, 1999, vol. 38, pp. 5878-5887.

Zemon, Harry, "An artificial solution for adoptive immunotherapy," *TRENDS in Biotechnology*, 2003, vol. 21(10), pp. 418-420.

Bendle, G. M., et al., "A Study of T Cell Tolerance to the Tumor-Associated Antigen MDM2: Cytokines Can Restore Antigen Responsiveness, but Not High Avidity T Cell Function," *PLoS ONE* 2(4): e353-e353 (9 pages), Public Library of Science, United States (Apr. 2007).

Donda, A., et al., "In vivo targeting of an anti-tumor antibody coupled to antigenic MHC class I complexes induces specific growth inhibition and regression of established syngeneic tumor grafts," *Cancer Immun.* 3.11 (17 pages) Academy of Cancer Immunology, United States (Aug. 2003).

Fujtt, S., et al., "Prolonged IFN-γ—producing NKT response induced with α-galactosylceramide—loaded DCs," *Nat Immunol.* 3(9):867-874, Nature Publishing Group, United States (Sep. 2002).

Mallevaey, T., et al., "Invariant and Noninvariant Natural Killer T Cells Exert Opposite Regulatory Functions on the Immune Response during Murine Schistosomiasis," *Infect. Immun.* 75(5): 2171-2180, American Society for Microbiology, United States (May 2007).

Pavlinkova, G., et al., "Pharmacokinetics and biodistribution of a light-chain-shuffled CC49 single-chain Fv antibody construct," *Cancer Immunol. Immunother.* 49(4-5): 267-275, Springer Verlag, Germany (Jul. 2000).

Porubsky, S. et al., "Normal development and function of invariant natural killer T cells in mice with isoglobotrihexosylceramide (iGb3) deficiency," *Proc Natl Acad Sci U.S.A.* 104(14): 5977-5982, National Academy of Sciences, United States (Apr. 2007).

Singh, A. K., at al., "The natural killer T cell ligand α-galactosylceramide prevents or NPL64 promotes pristane-induced lupus in mice," *Eur. J. Immunol.* 35(4):1143-1154, Weinheim : Wiley-VCH, Germany (Apr. 2005).

Supplementary European Search Report with the European Search Opinion for European Patent Application No. EP 08 72 5849, European Patent Office, Germany, mailed on Oct. 27, 2011.

Naidenko, O., et al., "Binding and Antigen Presentation of Ceramide-containing Glycolipids by Soluble Mouse and Human CD1d Molecules," *J. Exp. Med.*, 1999, vol. 190(8), pp. 1069-1079.

Behar, S. M., et al., "Susceptibility of Mice Deficient in CD1D or TAP1 to Infection with *Mycobacterium tuberculosis*," *J. Exp. Med.*, 1999, vol. 189, No. 12, pp. 1973-1980.

Behar, S. M., et al., "CD1-Restricted T cells in Host Defense to Infectious Diseases," *Curr. Top. Microbiol. Immunol.*, 2007, vol. 314, pp. 215-248.

Bendelac, A., "Mouse NK1$^+$ T cells," *Curr. Opinion in Immunol.*, 1995, vol. 7, pp. 367-374.

Bendelac, A., et al., "Mouse CD-1 Specific NK1 T Cells: Development, Specificity, and Function," *Annu. Rev. Immunol.*, 1997, vol. 15, pp. 535-562.

Bendelac, A. & Medzhitov, R., "Adjuvants of Immunity: Harnessing Innate Immunity to Promote Adaptive Immunity," *J. Exp. Med.*, 2002, vol. 195, No. 5, pp. F19-F23.

Brat, S., et al., "Galactosyl ceramide or a derivative is an essential component of the neural receptor for human immunodeficiency virus type 1 envelope glycoprotein gp120," *Proc. Natl. Acad. Sci. USA*, 1991, vol. 88, pp. 7131-7134.

Bocchia, M., et al., "Specific Binding of Leukemia Oncogene Fusion Protein Pepties to HLA Class I Molecules," *Blood*, 1995, vol. 85, No. 10, pp. 2680-2684.

Bocchia, M., et al., "Specific Human Cellular Immunity to bcr-abl Oncogene-Derived Peptides," *Blood*, 1996, vol. 87, No. 9, pp. 3587-3592.

Brossay, L., et al., "Cutting Edge: Structural Requirements for Galactosylceramide Recognition by CD1-Restricted NK T Cells," *J. Immunol.*, 1998, vol. 161, pp. 5124-5128.

Brossay, L., et al., "CD1d-mediated Recognition of an α-Galactosylceramide by Natural Killer T Cells is Highly Conserved through Mammalian Evolution," *J. Exp. Med.*, 1998, vol. 188, pp. 1521-1528.

Brutkiewicz, R. R. and Sriram, V., "Natural killer T (NKT) cells and thier role in antitumor immunity," *Crit. Rev. Oncol. Hematol.*, 2002, vol. 41, pp. 287-298.

Burdin, N., et al., "Immunization with α-galactosylceramide polarizes CD1-Reactive NK T cells toward Th2 cytokine synthesis," *Eur. J. Immunol.*, 1999, vol. 29, pp. 2014-2025.

Bynoe, M., et al., "Characterization of anti-DNA B cells that escape negative selection," *Eur. J. Immunol.*, 1999, vol. 29, pp. 1304-1313.

Bynoe, M., et al., "Estrogen up-regulates Bcl-2 and blocks tolerance induction of naïve B cells," *PNAS* 2000, vol. 97, No. 6, pp. 2703-2708.

Chackerian, A., et al., "Activation of NKT cells Protects Mice from Tuberculosis," *Infection and Immunity*, 2002, vol. 70, No. 11, pp. 6302-6309.

Chambers, B. J., et al., "Triggering of Natural Killer Cells by the Costimulatory Molecule CD80 (B7-1)," *Immunity*, 1996, vol. 5, pp. 311-317.

Chang, Y.-T., et al., "The Synthesis and Biological Characterization of a Ceramide Library," *J. Am. Chem. Soc.*, 2002, vol. 124, No. 9, pp. 1856-1857.

Chen, H., et al., NK1.1$^+$CD4$^+$ T Cells Lose NK1.1 Expression Upon In Vitro Activation, *J. Immunol.*, 1997, vol. 158, pp. 5112-5119.

Crowe, N., et al., "Glycolipid Antigen Drives Rapid Expansion and Sustained Cytokine Production by NK T Cells," *J. Immunol.*, 2003, vol. 171, pp. 4020-4027.

Davodeau, F., et al., "Close Phenotypic and Functional Similarities Between Human and Murine αβ T Cells Expressing Invariant TCR α-Chains," *J. Immunol.*, 1997, vol. 158, pp. 5603-5611.

Eberl, G. and Macdonald, R., "Rapid Death and Regeneration of NKT Cells in Anti-CD3ε- or IL-12-Treated Mice: A Major Role for Bone Marrow in NKT Cell Homeostasis," *Immunity*, 1998, vol. 9, pp. 345-353.

Eberl, G., et al., "Tissue-Specific Segregation of CD1d-Dependent and CD1d-Independent NK T Cells," *J. Immunol.*, 1999, vol. 162, pp. 6410-6419.

Emoto, M., et al., "Induction of IFN-γ-producing CD4$^+$ natural killer T cells by *Mycobacterium bovis* bacillus Calmette Guérin," *Eur. J. Immunol.*, 1999, vol. 29, pp. 650-659.

Enomoto, N., et al., "Immunization with dendritic cells loaded with α-galactosylceramide at priming phase, but not at boosting phase, enhances cytotoxic T lymphocyte activity against infection by intracellular bacteria," *FEMS Immunol. Med. Microbiol.*, 2007, vol. 51, pp. 350-362.

Fischer, K., et al., "Mycobacterial phosphatidylinositol mannoside is a natural antigen for CD1d-restricted T Cells," *PNAS*, 2004, vol. 101, No. 29, pp. 10685-10690.

Fujii, S-i., et al., "Glycolipid α-C-galactosylceramide is a distinct inducer of dendritic cell function during innate and adaptive immune responses of mice," *PNAS*, 2006, vol. 103, No. 30, pp. 11252-11257.

Fujii, S-i., et al., "Innate Vα14$^+$ natural killer T cells mature dendritic cells, leading to strong adaptive immunity," *Immunol. Rev.*, 2007, vol. 220, pp. 183-198.

(56) References Cited

OTHER PUBLICATIONS

Galli, G., et al., "Invariant NKT cells sustain specific B cell responses and memory," *PNAS*, 2007, vol. 104, No. 10, pp. 3984-3989.
Godfrey, D., et al., "NKT cells: facts, functions and fallacies," *Immunol. Today*, 2000, vol. 21, No. 11, pp. 573-583.
Gonzalez-Aseguinolaza, G., et al., "Natural Killer T Cell Ligand α-Galactosylceramide Enhances Protective Immunity Induced by Malaria Vaccines," *J. Exp. Med.*, 2002, vol. 195, No. 5, pp. 617-624.
Gumperz, J. E., et al., "Murine CD1d-Restricted T Cell Recognition of Cellular Lipids," *Immunity*, 2000, vol. 12, pp. 211-221.
Hayakawa, Y., et al., "Critical contribution of IFN-γ and NK cells, but not perforin-mediated cytotoxicity, to anti-metastatic effect of α-galactosylceramide," *Eur. J. Immunol.*, 2001, vol. 31, pp. 1720-1727.
Hong, S. and Van Kaer, L., "Immune Privilege: Keeping an Eye on Natural Killer T Cells," *J. Exp. Med.*, 1999, vol. 190, No. 9, pp. 1197-1200.
Ikarashi, Y., et al., "Dendritic Cell Maturation Overrules H-2D-mediated Natural Killer T (NKT) Cell Inhibition: Critical Role for B7 in CD1d-dependent NKT Cell Interferon γ Production," *J. Exp. Med.*, 2001, vol. 194, No. 8, pp. 1179-1186.
Inoue, H., et al., "α-Galactosylceramide (AGL-517) treatment protects mice from lethal irradiation," *Experimental Hematology*, 1997, vol. 25, pp. 935-944.
Ishikawa, H., et al., "$CD4^+ V_\alpha 14$ NKT cells play a crucial role in an early stage of protective immunity against infection with *Leishmania major*," *Int. Immunol.*, 2000, vol. 12, No. 9, pp. 1267-1274.
Joyce, S., et al., "Natural Ligand of Mouse CD1d1: Cellular Glycosylphosphatidylinositol," *Science*, 1998, vol. 279, pp. 1541-1544.
Kobayashi, E., et al., "Enhancing Effects of Agelasphin-11 on Natural Killer Cell Activities of Normal and Tumor-Bearing Mice," *Biol. Pharm. Bull.*, 1996, vol. 19, No. 3, pp. 350-353.
Kobayashi, E., et al., "Enhancing Effects of α-, β-Monoglycosylceramides on Natural Killer Cell Activity," *Bioorg. Med. Chem.*, 1996, vol. 4, No. 4, pp. 615-619.
Kojo, S., et al., "Dysfunction of T Cell Receptor AV24AJ18+, BV11+ Double-Negative Regulatory Natural Killer T Cells in Autoimmune Diseases," *Arthritus & Rheumatism*, 2001, vol. 44, No. 5, pp. 1127-1138.
Koseki, H., et al., "Dominant expression of a distinctive V14+ T-cell antigen receptor α chain in mice," *Proc. Natl. Acad. Sci. USA*, 1991, vol. 88, pp. 7518-7522.
Kronenberg, M. and Gapin, L., "The Unconventional Lifestyle of NKT Cells," *Nature Reviews*, 2002, vol. 2, pp. 557-568.
Kronenberg, M., "Toward an Understanding of NKT Cell Biology: Progress and Paradoxes," *Annu. Rev. Immunol.*, 2005, vol. 26, pp. 877-900.
Livingston, P., et al., "Improved Survival in Stage III Melanoma Patients With GM2 Antibodies: A Randomized Trial of Adjuvant Vaccination With GM2 Ganglioside," *Journal of Clinical Oncology*, May 1994, vol. 12(5), pp. 1036-1044.
MacDonald, H., "Development and selection of NKT cells," *Current Opinion in Immunology*, 2002, vol. 14, pp. 250-254.
Matsuda, J. & Kronenberg, M. "Presentation of self and microbial lipids by CD1 molecules," *Current Opinion in Immunology*, 2001, vol. 13, pp. 19-25.
Mattner, J., et al., "Exogenous and endogenous glycolipid antigens activate NKT cells during microbial infections," *Nature*, 2005, vol. 434, pp. 525-529.
Mieza, M. A., et al., "Selective Reduction of $v\alpha 14^+$ NK T Cells Associated with Disease Development in Autoimmune-Prone Mice," *J. Immunol.*, 1996, vol. 156, pp. 4035-4040.
Minamino, M., et al., "Bacterial ceramides and sphingophospholipids induce apoptosis of human leukaemic cells," *Microbiology*, 2003, vol. 149, pp. 2071-2081.
Moody, D., et al., "The molecular basis of CD1-mediated presentation of lipid antigens," *Immunol. Rev.*, 1999, vol. 172, pp. 285-296.
Morita, M., et al., "Structure-Activity Relationship of α-Galactosylceramides against B16-Bearing Mice," *J. Med. Chem.*, 1995, vol. 38, pp. 2176-2187.
Motoki, K., et al., "Immunostimulatory and Antitumor Activities of Monoglycosylceramides Having Various Sugar Moieties," *Biol. Pharm. Bull.*, 1995, vol. 18, No. 11, pp. 1487-1491.
Motoki, K., et al., "Effects of α-Galactosylceramides on Bone Marrow Cells in Vitro and Hematopoiesis in Vivo," *Biol. Pharm. Bull.*, 1996, vol. 19, No. 7, pp. 952-955.
Nagle, D., et al., "New Glycosphingolipids from the Marine Sponge *Halichondria panicea*," *Journal of Natural Products*, 1992, vol. 55, No. 7, pp. 1013-1017.
Nakagawa, R., et al., "Antotumor Activity of α-Galactosylceramide, KRN7000, in Mice with EL-4 Hepatic Metastasis and its Cytokine Production," *Oncology Research*, 1998, vol. 10, pp. 561-568.
Nakagawa, R., et al., "Antitumor Activity of α-Galactosylceramide, KRN7000, in Mice with the Melanoma B16 Hepatic Metastasis and Immunohistological Study of Tumor Infiltrating Cells," *Oncology Research*, 2000, vol. 12, pp. 51-58.
NCBI Entrez, GenBank Report, Accession No. NP 001065272 (Entry Date 2006), 2 pages.
Oishi, Y., et al., "Selective Reduction and Recovery of Invariant $V\alpha 24 J\alpha Q$ T Cell Receptor T Cells in Correlation with Disease Activity in Patients with Systemic Lupus Erythematosus," *J. Rheumatol.*, 2001, vol. 28, No. 2, pp. 275-283.
Park, S-H and Bendelac, A., "CD1-restricted T-cell responses and microbial infection", *Nature*, 2000, vol. 406, pp. 788-792.
Peterson, P. A., et al., "$\beta_2$-Microglobulin and the Major Histocompatibility Complex," *Adv. Cancer Res.*, 1977, vol. 24, pp. 115-163.
Porcelli, S., et al., "Analysis of T Cell Antigen Receptor (TCR) Expression by Human Peripheral Blood $CD4^{-8-}\alpha/\beta$ T Cells Demonstrates Preferential Use of Several Vβ Genes and an Invariant TCR α Chain," *J. Exp. Med.*, 1993, vol. 178, pp. 1-16.
Porcelli, S., "The CD1 Family: A Third Lineage of Antigen-Presenting Molecules," *Advances in Immunology*, 1995, vol. 59, pp. 1-98.
Porcelli, S., et al., "The CD1 family of lipid antigen-presenting molecules," *Review Immunology Today*, 1998, vol. 19, No. 8, pp. 362-368.
Porcelli, S. and Modlin, R., "The CD1 System: Antigen-Presenting Molecules for T Cell Recognition of Lipids and Glycolipids," *Annu. Rev. Immunol.*, 1999, vol. 17, pp. 297-.
Ranson, T., et al., "Invariant $V\alpha 14^+$ NKT Cells Participate in the Early Response to Enteric *Listeria monocytogenes* Infection," *J. Immunol.*, 2005, vol. 175, pp. 1137-1144.
Robert, B., et al., "Antibody-conjugated MHC class I tetramers can target tumor cells for specific lysis by T lymphocytes," *Eur. J. Immunol.*, 2000, vol. 30, pp. 3165-3170.
Rötzschke, O., et al., "Superactivation of an immune response triggered by oligomerized T cell epitopes," *Proc. Natl. Acad. Sci. USA*, 1997, vol. 94, pp. 14642-14647.
Schmieg, J., "Superior Protection against Malaria and Melanoma Metastases by a C-glycoside Analogue of the Natural Killer T Cell Ligand α-Galactosylceramide," *J. Exp. Med.*, 2003, vol. 198, No. 11, pp. 1631-1641.
Seino, K-i., et al., "Requirement for natural killer T (NKT) cells in the induction of allograft tolerance," *PNAS*, 2001, vol. 98, No. 5, pp. 2577-2581.
Shamshiev, A., et al., "Self glycolipids as T-cell autoantigens," *Eur. J. Immunol.*, 1999, vol. 29, pp. 1667-1675.
Shin, S-U. and Morrison, S. L., "[32] Production and Properties of Chimeric Antibody Molecules," *Methods in Enzymology*, 1989, vol. 178, pp. 459-477.
Shin, S-U., et al., "Functional and Pharmacokinetic Properties of Antibody-Avidin Fusion Proteins," *J. Immunol.*, 1997, vol. 158, pp. 4797-4804.
Sidobre, S., et al., "The Vα14 NKT Cell TCR Exhibits High-Affinity Binding to a Glycolipid/CD1d Complex," *J. Immunol.*, 2002, vol. 169, pp. 1340-1348.
Sidobre, S. and Kronenberg, M., "CD1 tetramers: a powerful tool for the analysis of glycolipid-reactive T cells," *Journal of Immunological Methods*, 2002, vol. 268, pp. 107-121.

(56) References Cited

OTHER PUBLICATIONS

Sieling, P. A., et al., "Human Double-Negative T Cells in Systematic Lupus Erythematosus provide Help for IgG and are Restricted by CD1c," *J. Immunol.*, 2000, vol. 165, pp. 5338-5344.
Smyth, M. and Godfrey, D. I., "NKT cells and tumor immunity-a double-edged sword," *Nature Immunology*, 2000, vol. 1, No. 6, pp. 459-460.
Sonoda, K-H, et al., "CD1-reactive Natural Killer T Cells are Required for Development of Systemic Tolerance through an Immune-priviledged Site," *J. Exp. Med.*, 1999, vol. 190, No. 9, pp. 1215-1225.
Spada, F. M., et al., "CD1d-restricted Recognition of Synthetic Glycolipid Antigens by Human Natural Killer T Cells," *J. Exp. Med.*, 1998, vol. 188, No. 8, pp. 1529-1534.
Takeda, K. and Dennert, G., "The Development of Autoimmunity in C57BL/6 lpr Mice Correlates with the Disappearance of Natural Killer Type 1-positive Cells: Evidence for Their Suppressive Action on Bone Marrow Stem Cell Proliferation, B Cell Immunoglobulin Secretion, and Autoimmune Symptoms," *J. Exp. Med.*, 1993, vol. 177, pp. 155-164.
Tomioka, H., "Adjunctive Immunotherapy of Mycobacterial Infections," *Current Pharmaceutical Design*, 2004, vol. 10, pp. 3297-3312.
Tsuji, M., "Glycolipids and phospholipids as natural CD1d-binding NKT cell ligands," *Cell Mol. Life Sci.*, 2006, vol. 63, pp. 1889-1898.
Uchimura, A., et al., "Immunostimulatory Activities of Mono- or Diglycosylated α-Galactosylceramides," *Bioorg. Med. Chem.*, 1997, vol. 5, No. 7, pp. 1447-1452.
Uchimura, A., et al., "Immunostimulatory Activities of Monoglycosylated α-D-Pyranosylceramides," *Bioorg. Med. Chem.*, 1997, vol. 5, No. 12, pp. 2245-2249.
Vincent, M. S., et al., "CD1-dependent dendritic cell instruction," *Nature Immunol.*, 2002, vol. 3, No. 12, pp. 1163-1168.
Wang, B., et al., "CD1-restricted NK T Cells Protect Nononese Diabetic Mice from Developing Diabetes," *J. Exp. Med.*, 2001, vol. 194, No. 3, pp. 313-319.
Whitmire, J., et al., "Direct Interferon-γ Signaling Dramatically Enhances $CD4^+$ and $CD8^+$ T Cell Memory[1]," *The Journal of Immunology*, 2007, vol. 179, pp. 1190-1197.
Wilson, S., et al., "Exreme Th1 bias of invariant Vα24JαQ T cells in type 1 diabetes," *Nature*, Jan. 1998, vol. 391, pp. 177-181.
Wilson, S. & Delovitch, T., Janus-Like Roe of Regulatory iNKT Cells in Autoimmune Disease and Tumor Immunity, *Nature Review Immunology*, 2003, vol. 3, pp. 211-222.
Wu, D., et al., "Cross-presentation of Disialoganglioside GD3 to Natural Killer T Cells," *J. Exp. Med.*, 2003, vol. 198, No. 1, pp. 173-181.
Yamaguchi, Y., et al., "Enhancing Effects of (2S,3S,4R)-1-O-(α-D-galactopyranosyl)-2-(N-Hexacosanoylamino)-1,3,4-Octadecanetriol (KRN7000) on Antigen-Presenting Function of Antigen-Presenting Cells and Antimetastatic Activity of KRN7000-Pretreated Antigen-Presenting Cells," *Oncology Research*, 1996, vol. 8, Nos. 10/11, pp. 399-407.
Yoshimoto, T. and Paul W. E., "$CD4^{pos}$, $NK1.1^{pos}$ T Cells Promptly Produce Interlukin 4 in Response to In Vivo Challenge with Anti-CD3," *J. Exp. Med.*, 1994, vol. 179, pp. 1285-1295.
Yoshimoto, T., at al., "Defective IgE production by SJL mice is linked to the absence of $CD4^+$, $NK1.1^+$ T cells that promptly produce interleukin 4," *Proc. Nod Acad. Sci. USA*, 1995, vol. 92, pp. 11931-11934.
Yoshimoto, T., et al., "Role of $NK1.1^+$ T Cells in a $T_H2$ Response and in Immunoglobulin E Production," *Science*, 1995, vol. 270, Issue 5243, pp. 1845-1847.
Yu, K. O. A., at al., "Modulation of CD1d-restricted NKT cell responses by using N-acyl variants of α-galactosylceramides," *PNAS*, 2005, vol. 102, No. 9, pp. 3383-3388.
Yu, K. O. A., et al., "Production and characterization of monoclonal antibodies against complexes of the NKT cell ligand α-galactosylceramide bound to mouse CD1d," *J. Immunol. Methods*, 2007, vol. 323, pp. 11-23.
Zeng, D., at al., "Bone Marrow $NK1.1^-$ and $NK1.1^+$ T Cells Reciprocally Regulate Acute Graft versus Host Disease," *J. Exp. Med.*, 1999, vol. 189, No. 7, pp. 1073-1081.
Zeng, D., et al., "Cutting Edge: A Role for CD1 in the Pathogenesis of Lupus in NZB/NZW Mice," *J. Immunol.*, 2000, vol. 164, pp. 5000-5004.
Hammond, K., et al., "α/β-T Cell Receptor $(TCR)^+CD4^- CD8^-$ (NKT) Thymocytes Prevent Insulin-dependent Diabetes Mellitus in Nonobese Diabetic (NOD)/Lt Mice by the Influence of Interleukin (IL)-4 and/or IL-10," *J. Exp. Med.*, 1998, vol. 187, No. 7, pp. 1047-1056.
Iijima, H., et al., "Structure-Activity Relationship and Conformational Analysis of Monoglycosylceramides on the Syngeneic Mixed Leukocyte Reaction," *Bioorg. Med. Chem.*, 1998, vol. 6, pp. 1905-1910.
Kitamura, H., et al., "The Natural Killer T (NKT) Cell Ligand α-Galactosylceramide Demonstrates Its Immunopotentiating Effect by Inducing Interleukin (IL)-12 Production by Dendritic Cells and IL-12 Receptor Expression on NKT Cells," *J. Exp. Med.*, 1999, vol. 189, No. 7, pp. 1121-1127.
Laloux, V., et al., "NK T Cell-Induced Protection Against Diabetes in Vα14-Jα281 Transgenic Nonobese Diabetic Mice Is Associated with a Th2 Shift Circumscribed Regionally to the Islets and Functionally to Islet Autoantigen," *J. Immunol.*, 2001, vol. 166, pp. 3749-3756.
Burdin, N., et al, "Selective ability of mouse CD1 to present glycolipids: α-galactosylceramide specifically stimulates $Vα14^+$ NK T lymphocytes," *J. Immunol.*, 1998, vol. 161, pp. 3271-3281.
Dunbar, et al., "Direct isolation, phenotyping and cloning of low-frequency antigen-specific cytotoxic T lymphocytes from peripheral blood," *Curr Biol*, 1998, vol. 8, No. 7, pp. 413-416.
Gaynor, B., et al, "Peptide inhibition of glomerular deposition of an anti-DNA antibody," *Proc. Natl. Acad. Sci USA.*, 1997, vol. 94, pp. 1955-1960.
Hahn, B., "Antibodies to DNA," *New England Journal of Medicine*, 1998, vol. 338(19), pp. 1359-1368.
Hashimoto, M., et al, "Versatile Synthesis of Phenoxydiazirine-Based Fatty Acid Analogues and Photoreactive Galactosylceramide," *Bioorganic & Medicinal Chemistry Letters*, 2002, vol. 12, pp. 89-91.
Hu, V. W. and Wisnieski, B. J., "Photoreactive labeling of M13 coat protein in model membranes by use of a glycolipid probe," *Proc. Natl. Acad. Sci. USA*, 1979, vol. 76, No. 11, pp. 5460-5464.
Huang, Y., et al., "Enhancement of HIV DNA vaccine immunogenicity by the NKT cell ligand, α-galactosylceramide," *Vaccine*, 2008, vol. 26, pp. 1807-1816.
Kotzin, B., "Systemic Lupus Erythematosus," *Cell*, 1996, vol. 85, pp. 303-306.
Kuo, P., et al., "Bcl-2 leads to expression of anti-DNA B cells but no nephritis: a model for a clinical subset," *Eur. J. Immunol.*, 1999, vol. 29, pp. 3168-3178.
Lutz, M., et al., "An advanced culture method for generating large quantities of highly pure dendritic cells from mouse bone marrow," *J. Immunol. Methods*, 1999, vol. 223, pp. 77-92.
Parekh, V., et al., "Quantitative and Qualitative Differences in the In Vivo Response of NKT Cells to Distinct α-and β-Anomeric Glycolipids[1]", *The Journal of Immunology*, 2004, vol. 173, pp. 3693-3706.
Park, . J-E et al., "Fine specificity of natural killer T cells against GD3 ganglioside and identification of GM3 as an inhibitory natural killer T-cell ligand," *Immunology*, 2008, vol. 123, pp. 145-155.
Pisetsky, D., "Systemic Lupus Erythematosus Diagnosis and Treatment," *The Medical Clinics of North America*, 1997, vol. 81(1), pp. 113-128.
Putterman, C., et al., "Immunization with a Peptide Surrogate for Double-stranded DNA (dsDNA) Induces Autoantibody Production and Renal Immunoglobulin Deposition," *J. Exp. Med.*, 1998, vol. 188(1), pp. 29-38.
Putterman, C., et al., "Molecular Analysis of the Autoantibody Response in Peptide-Induced Autoimmunity," *The Journal of Immunology*, 2000, vol. 164, pp. 2542-2549.

(56) References Cited

OTHER PUBLICATIONS

Rao, V., et al., "*Mycobacterium tuberculosis* controls host innate immune activation through cyclopropane modification of a glycolipid effector molecule," *J. Exp. Med.*, 2005, vol. 201(4), pp. 535-543.

Rao, V., et al., "Trans-cyclopropanation of mycolic acids on trehalose dimycolate suppresses *Mycobacterium tuberculosis*-induced inflammation and virulence," *J. Clin. Invest.*, 2006, vol. 116(6), pp. 1660-1667.

Sonnino et al., "A Photoreactive Derivative of Radiolabeled GM1 Ganglioside: preparation and use to establish the involvement of specific proteins in GM1 uptake by human fibroblasts in culture," *Biochemistry*, 1989, vol. 28, pp. 77-84.

Spatz, L., et al., "Light Chain Usage in Anti-double-stranded DNA B Cell Subsets: Role in Cell Fate Determination," *J. Exp. Med.*, 1997, vol. 185(7), pp. 1317-1326.

Sullivan and Kronenberg, "Activation or anergy: NKT cells are stunned by α-galactosylceramide," *J. Clin. Invest.*, 2005, vol. 115, pp. 2328-2329.

Tamada, K., et al., "Immunosuppressive activity of cloned natural killer (NK1.1+) T cells established from murine tumor-infiltrating lymphocytes," *J. Immunol.*, 1997, vol. 158, pp. 4846-4854.

Taraban, V., et al., "Invariant NKT Cells Promote CD8+ Cytotoxic T Cell Responses by Inducing CD70 Expression on Dendritic Cells," *J. Immunol.*, 2008, vol. 180, pp. 4615-4620.

Uldrich et al., "NKT cell stimulation with glycolipid antigen in vivo: costimulation-dependent expansion, bim-dependent contraction, and hyporesponsiveness to further antigenic challenge," *J. Immunol.*, 2005, vol. 175, pp. 3092-3101.

Venkataswamy, M., et al., "Incorporation of NKT cell activating glycolipids enhances immunogenicity and vaccine efficacy of *Mycobacterium bovis* BCG," *J. Immunol.*, 2009, vol. 183(3), pp. 1644-1656.

Wheeler, et al, "A novel cationic lipid greatly enhances plasmid DNA delivery and expression in mouse lung," *Proc. Natl. Acad. Sci. USA*, 1996, vol. 93, pp. 11454-11459.

Zegers, M. M. P., et al., "Use of photoactivatable sphingolipid analogues to monitor lipid transport in mammalian cells," *Biochem. J.*, 1997, vol. 328, pp. 489-498.

Zuidam and Barenholz, "Electrostatic parameters of cationic liposomes commonly used for gene delivery as determined by 4-heptadecyl-7-hydroxycoumarin," *Biochim Biophys Acta*, 1997, vol. 1329, pp. 211-222.

\* cited by examiner

Higher frequencies of iNKT cells in the blood upon systemic treatment with recombinant CD1d molecules a b

Pretreatment of mice with aGalCer-loaded sCD1d confers protection against tumor development

αGalCer/CD1d-anti HER2 fusion protein blocks tumor development only when bound to HER2-expressing cancer cells a b

Systemic treatment with the αGalCer/CD1d-anti HER2 fusion protein inhibits lung metastasis development induced by B16-HER2 cells a b

αGalCer/CD1d molecules promote innate and adaptive immune responses induced by activated iNKT cells a b c

αGalCer/sCD1d protein acts as adjuvant in the development of an antigen-specific immune response a b c

MODULATION OF NKT CELL ACTIVITY WITH ANTIGEN-LOADED CD1D MOLECULES

CROSS-REFERENCE TO RELATED APPLICATIONS

This application claims the benefit of the filing date of U.S. Patent Appl. No. 60/890,964, filed Feb. 21, 2007, which is incorporated by reference herein in its entirety.

BACKGROUND OF THE INVENTION

Field of the Invention

The invention generally relates to the field of immunology.

Background Art

The natural immune system strikes a complex balance between highly aggressive, protective immune responses to foreign pathogens and the need to maintain tolerance to normal tissues. In recent years there has been increasing recognition that interactions among many different cell types contribute to maintaining this balance. Such interactions can, for example, result in polarized responses with either production of pro-inflammatory cytokines (e.g., interferon-gamma) by TH1 type T cells or production of interleukin-4 (IL-4) by TH2 type T cells that suppress TH1 activity. In a number of different animal models, T cell polarization to TH1 has been shown to favor protective immunity to tumors or infectious pathogens whereas T cell polarization to TH2 can be a critical factor in preventing development of cell-mediated autoimmune disease. The conditions that determine whether immune stimulation will result in aggressive cell-mediated immunity or in down regulation of such responses are highly localized in the sense that each tissue is comprised of a distinctive set of antigen presenting cells (APC) and lymphocyte lineages that interact to favor different immune responses. For example, under optimal conditions, the dendritic cells (DC) localized in a normal tissue may represent predominantly a lineage and stage of maturation that favors tolerogenic interactions and serves as a barrier to cell-mediated autoimmunity whereas a tumor or site of infection will attract mature myeloid dendritic cells that stimulate potent cell-mediated immune responses.

CD1d-restricted NKT cells are a unique class of non-conventional T cells that appear to play an important role in defining the outcome of immune stimulation in the local environment. They share with the larger class of NKT cells the expression of markers of both the T cell and natural killer (NK) cell lineages. As such, NKT cells are considered as part of innate immunity like NK cells and in humans their frequency in normal individuals can be as high as 2.0% of total T lymphocytes (Gumperz et al., 2002. J Exp Med 195:625; Lee et al., 2002. J Exp Med 195:637).

CD1d-restricted NKT cells are distinguished from other NKT cells by their specificity for lipid and glycolipid antigens presented by the monomorphic MHC class Ib molecule, CD1d (Kawano et al., Science 278 (1997), pp. 1626-1629). CD1d is a non-MHC encoded molecule that associates with β2-microglobulin and is structurally related to classical MHC class I molecules. CD1d has a hydrophobic antigen-binding pocket that is specialized for binding the hydrocarbon chains of lipid tails or hydrophobic peptides (Zeng et al., Science 277 (1997), pp. 339-345). CD1d is known to bind a marine sponge derived α-glycosylated sphingolipid, α-galactosylceramide (α-GalCer), and related molecules such as ceramide-like glycolipid antigens with α-linked galactose or glucose but not mannose (Kawano et al., Science 278 (1997), pp. 1626-1629; and Zeng et al., Science 277 (1997), pp. 339-345). As discussed below, the ability to activate CD1d-restricted NKT cells by stimulation with α-GalCer or related molecules bound to CD1d of antigen presenting cells has greatly facilitated functional analysis of this non-conventional T cell subset. In the absence of inflammation, CD1d-restricted NKT cells have been shown to localize preferentially in certain tissues like thymus, liver and bone marrow (Wilson et al., 2002. Trends Mol Med 8:225) and antitumor activity of NKT cells has been mainly investigated in mouse liver metastasis.

NKT cells have an unusual ability of secreting both TH1 and TH2 cytokines and potent cytotoxic as well as regulatory functions have been documented in inflammation, autoimmunity and tumor immunity (Bendelac et al., (1995) Science 268:863; Chen and Paul. 1997. J Immunol 159: 2240; and Exley et al., 1997. J Exp Med 186:109).

Among the CD1d-restricted NKT cells is a subset, referred to herein as "iNKT cells," that express a highly conserved αβT cell receptor (TCR). In man this invariant TCR is comprised of Vα24Jα15 in association with Vβ11 whereas in mice the receptor comprises the highly homologous Vα14Jα18 and Vβ8.2. Other CD1d-restricted NKT cells express more variable TCR. Both TCR invariant and TCR variant classes of CD1d-restricted T cells can be detected by binding of CD1d-tetramers loaded with α-GalCer (Benlagha et al., J Exp Med 191 (2000), pp. 1895-1903; Matsuda et al., J Exp Med 192 (2000), pp. 741-754; and Karadimitris et al., Proc Natl Acad Sci USA 98 (2001), pp. 3294-3298). CD1d-restricted NKT cells, as defined in this application (CD1d-restricted NKT), include cells that express either invariant or variant TCR and that bind or are activated by CD1d loaded with either α-GalCer or with related ceramide-like glycolipid antigens. CD1d-restricted NKT cells, as defined in this application (CD1d-NKT), include cells that express either invariant or variant TCR and that bind or are activated by CD1d loaded with either α-GalCer or with related sphingolipids that have α-linked galactose or glucose including molecules such as OCH, which differs from α-GalCer by having a shortened long-chain sphingosine base (C5 vs. C14) and acyl chain (C24 vs. C26) (Miyamoto et al., Nature 2001 413:531-4).

CD1d-restricted NKT have been shown to have direct cytotoxic activity against targets that express CD1d. It is likely, however, that the effect of CD1d-restricted NKT on immune responses is amplified through recruitment of other lymphocytes either by direct interaction or, perhaps even more importantly, by indirect recruitment through interaction with DC. CD1d-restricted NKT have the unique ability to secrete large quantities of IL-4 and IFN-γ early in an immune response. Secretion of IFN-γ induces activation of DC which produce interleukin-12 (IL-12). IL-12 stimulates further IFN-γ secretion by NKT cells and also leads to activation of NK cells which secrete more IFN-γ.

Since CD1d-restricted NKT are able to rapidly secrete large amounts of both IL-4 and IFN-γ, the polarization of immune responses will depend on whether the effect of pro-inflammatory IFN-γ or anti-inflammatory IL-4 cytokines predominate. This has been reported to be, in part, a function of the relative frequency of different subsets of CD1d-restricted NKT. These subsets include (i) an invariant CD1d-restricted NKT population that is negative for both CD4 and CD8 and that gives rise to predominantly a TH1 type response including secretion of pro-inflammatory IFN-γ and TNF-α and (ii) a separate population of CD1d-restricted NKT that is CD4+ and that gives rise to both a TH1 type and TH2 type response including secretion of the anti-inflammatory Th2-type cytokines IL-4, IL-5, IL-10 and IL-13 (Lee et al., J Exp Med 2002; 195:637-41; and Gumperz et al., J Exp Med 2002; 195:625-36). In addition, NKT cell activity is differentially modulated by depending on the particular ceramide-like glycolipid bound to CD1d (see, e.g., US Patent Application Publication No. 2006/0052316). Local factors that influence activation of CD1d-restricted NKT subsets include the cytokine environment and, importantly, the DC that are recruited to that environment.

A number of indirect mechanisms contribute to the protective effect of CD1d-restricted NKT cells. Activation of NKT cells by administration of α-GalCer in vivo results in concomitant activation of NK cells (Eberl and MacDonald, Eur. J. Immunol. 30 (2000), pp. 985-992; and Carnaud et al., J. Immunol. 163 (1999), pp. 4647-4650). In mice deficient in NKT cells, α-GalCer is unable to induce cytotoxic activity by NK cells. NKT cells also enhance the induction of classical MHC class I restricted cytotoxic T cells (Nishimura et al., Int Immunol 2000; 12:987-94; and Stober et al., J immunol 2003; 170:2540-8).

The availability of a defined antigen, e.g., α-GalCer and related antigens, that can be employed to specifically activate CD1d-restricted NKT cells has made it possible to examine the role of these non-conventional T cells in a variety of immune responses.

Indeed, α-GalCer has significant promise as a therapeutic agent or adjuvant. For example, α-GalCer administration has a dramatic effect on a number of different microbial infections, including protective effects in murine malaria, fungal and hepatitis B virus infections (Kakimi et al, J Exp Med 192 (2000), pp. 921-930; Gonzalez-Aseguinolaza et al., Proc Natl Acad Sci USA 97 (2000), pp. 8461-8466; and Kawakami et al., Infect Immun 69 (2001), pp. 213-220). Dramatic effects of administration of α-GalCer have also been observed in animal models of tumor immunity. For example, stimulation with α-GalCer suppresses lung and liver metastases in an NKT dependent manner (Smyth et al., 2002. Blood 99:1259). In addition, α-GalCer has been shown to have a protective effect against certain autoimmune diseases, including type 1 diabetes a,d experimental autoimmune encephalomyelitis (EAE, a well-known model system for multiple sclerosis) (Hong S, et al. Nat. Med. 2001; 7:1052-1056 and Miyamoto K. et al. Nature. 2001; 413:531-534).

However, NKT cells, upon restimulation with α-GalCer, become unresponsive, e.g., reduced in their capacity to proliferate, produce cytokines, transactivate other cell types, and prevent tumor metastasis. Parekh, V V, et al. J. Clin. Invest. 115:2572-2583 (2005). Accordingly, there remains a 0need in the art for methods of stimulating NKT cells multiple times without causing the NKT cells to become nonresponsive.

SUMMARY OF THE INVENTION

In one embodiment, the present invention is directed to a method of modulating an immune response in an animal, comprising administering to an animal in need of immune modulation a composition comprising: (a) non-specific CD1d complex which comprises: (i) an isolated soluble CD1d polypeptide sufficient to associate with β2-microglobulin and bind a ceramide-like glycolipid antigen; (ii) an isolated polypeptide comprising β2-microglobulin or a fragment thereof associated with the CD1d polypeptide; and (iii) a ceramide-like glycolipid antigen bound to the CD1d polypeptide; and (b) a carrier; wherein the non-specific CD1d complex is administered in an amount sufficient to affect the activity of NKT cells in the animal.

In another embodiment, the present invention is directed to a method of treating a disease in an animal, comprising administering to an animal with said disease a composition comprising: (a) non-specific CD1d complex which comprises: (i) an isolated soluble CD1d polypeptide sufficient to associate with β2-microglobulin and bind a ceramide-like glycolipid antigen; (ii) an isolated polypeptide comprising β2-microglobulin or a fragment thereof associated with the CD1d polypeptide; and (iii) a ceramide-like glycolipid antigen bound to the CD1d polypeptide; and (b) a carrier; wherein said composition is administered in an amount sufficient to alter the progression of the disease.

In another embodiment the present invention is directed to a method of inhibiting an anergic effect of a ceramide-like glycolipid antigen on NKT cell activity, comprising: stimulating NKT cells with the ceramide-like glycolipid antigen as part of a CD1d complex, where the complex comprises: (a) an isolated soluble CD1d polypeptide sufficient to associate with β2-microglobulin and bind a ceramide-like glycolipid antigen; (b) an isolated polypeptide comprising β2-microglobulin or a fragment thereof associated with the CD1d polypeptide; and (c) the ceramide-like glycolipid antigen bound to the CD1d polypeptide; and restimulating said NKT cells one or more times with said complex; wherein said NKT cells are activated in response to said stimulation, and wherein said NKT cells are reactivated in response to said restimulation by said complex.

In yet another embodiment, the present invention is directed to a method of modulating an immune response to an immunogen in an animal, comprising administering to an animal in need thereof a composition comprising: (a) an immunogen; (b) a CD1d complex, said complex comprising: (i) an isolated soluble CD1d polypeptide sufficient to associate with β2-microglobulin and bind a ceramide-like glycolipid antigen; (ii) an isolated polypeptide comprising β2-microglobulin or a fragment thereof associated with the CD1d polypeptide; and (iii) a ceramide-like glycolipid antigen bound to the CD1d polypeptide; and (c) a carrier; wherein the CD1d complex is administered in an amount sufficient to modulate the immune response against the immunogen relative to administration of the immunogen in the absence of the CD1d complex.

In yet another embodiment the present invention is directed to a method of treating a disease in an animal, comprising administering to an animal in need thereof a composition comprising: (a) an immunogen; (b) a CD1d complex which comprises: (i) an isolated soluble CD1d polypeptide sufficient to associate with β2-microglobulin and bind a ceramide-like glycolipid antigen; (ii) an isolated polypeptide comprising β2-microglobulin or a fragment thereof associated with the CD1d polypeptide; and (iii) a ceramide-like glycolipid antigen bound to the CD1d polypeptide; and (c) a carrier; wherein an immune response against the immunogen is effective in treating the disease, and wherein the CD1d complex is administered in an amount sufficient to modulate the immune response against the immunogen relative to administration of the immunogen in the absence of the CD1d complex.

In yet another embodiment the present invention is directed to a method of preventing a disease in an animal, comprising administering to an animal in need thereof a composition comprising: (a) an immunogen; (b) a CD1d complex which comprises: (i) an isolated soluble CD1d polypeptide sufficient to associate with β2-microglobulin and bind a ceramide-like glycolipid antigen; (ii) an isolated polypeptide comprising β2-microglobulin or a fragment thereof associated with the CD1d polypeptide; and (iii) a ceramide-like glycolipid antigen bound to the CD1d polypeptide; and (c) a carrier; wherein an immune response against the immunogen is effective in treating the disease, and wherein the CD1d complex is administered in an amount sufficient to modulate the immune response against the immunogen relative to administration of the immunogen in the absence of the CD1d complex.

The present invention is further directed to a composition comprising any CD1d complex described herein.

BRIEF DESCRIPTION OF THE FIGURES

FIG. 2: a Sustained IFNγ production by liver and spleen iNKT cells after several injections of CD1d/anti-HER2 fusion. Liver and spleen lymphocytes were isolated 20 minutes after the sixth injection of either PBS (control, white bar), αGalCer 0.4 µg (grey bar), or αGalCer/CD1d-anti-HER2 fusion protein 40 µg (black bar) and cultured for 1 hour in presence of GOLGI PLUG™ reagent. NKT cells were then stained with anti NK1.1-PE and anti CD3-FITC antibodies, fixed and stained for intracellular IFNγ with anti IFNγ-APC. Graph shows percentage of IFNγ producing NKT cells (gated on NK1.1+ CD3+ cells). b Sustained IFNγ production by liver NKT cells after several injections i.v. and in vitro rechallenge with αGalCer or αGalCer loaded recombinant CD1d molecules. Liver lymphocytes were isolated after 5 injections i.v. of either PBS (Control), αGalCer, αGalCer/CD1d-anti-HER2 fusion protein (Fusion) or αGalCer/sCD1d (sCD1d) and stimulated in vitro for 6 hours in presence of GOLGI PLUG™ as indicated. (PBS, white; αGalCer, light grey; αGalCer/CD1d-anti-HER2 fusion, black; αGalCer/sCD1d, dark grey) Cells were stained for FACS analysis as described in a.

DETAILED DESCRIPTION OF THE INVENTION

Figure 1:
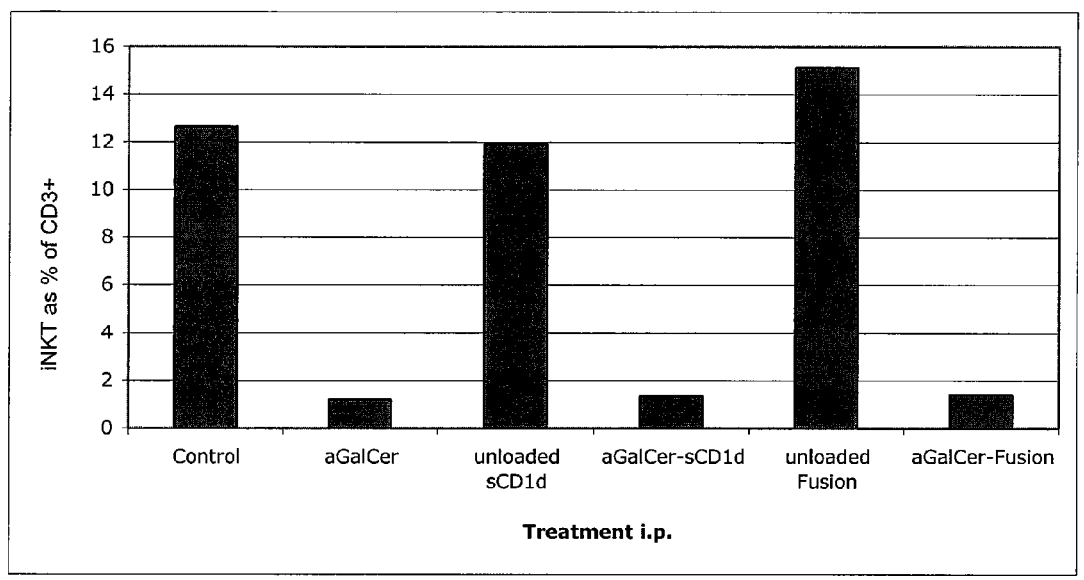
FIG. 1: In vivo biological activity of αGalCer-loaded sCD1d and CD1d-anti HER2 fusion protein shown by the transient disappearance of liver iNKT cells 20 hours after i.p. injection with PBS (control), αGalCer 5 µg, or αGalCer/sCD1d 20 µg or αGalCer/CD1d-anti-HER2 fusion 40 µg (loaded or unloaded). Frequency of iNKT cells was measured by flow cytometry using CD1d-Tetramer-EXTRAVIDIN®-PE and anti CD3 FITC.

The present invention provides compositions and methods which are useful for modulating, i.e., either eliciting, inhibiting, or stimulating, an immune response. The compounds comprise one or more CD1d complexes comprising a ceramide-like glycolipid antigen bound to a soluble CD1d polypeptide fragment associated with beta-2 microglobulin. In certain embodiments, the soluble CD1d complexes of the present invention are non-specific, i.e., they are not targeted to any particular tissue, cell, or cell surface marker. Soluble CD1d complexes for use in the methods of the present invention modulate an immune response by affecting the activity of CD1d-restricted natural killer T ("NKT") cells. Soluble CD1d complexes as described herein are useful for stimulating desirable immune responses, for example, immune responses against infectious agents or cancer; or for inhibiting undesirable immune responses, such as allergic responses, allograft rejections, and autoimmune diseases. In certain embodiments, soluble CD1d complexes of the present invention are administered with an immunogen and function as an adjuvant by, for example, increasing or modulating the immune response to the immunogen.

Definitions

It is to be noted that the term "a" or "an" entity refers to one or more of that entity; for example, "a vector" is understood to represent one or more vectors. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to polypeptides of the present invention include any polypeptides that retain at least some of the biological, antigenic, or immunogenic properties of the corresponding native polypeptide. Fragments of polypeptides of the present invention include proteolytic fragments, as well as deletion fragments, in addition to other specific fragments discussed elsewhere herein. Variants of polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of polypeptides of the present invention, are polypeptides which have been altered so as to exhibit additional features not found on the native polypeptide. Examples include fusion proteins. Variant polypeptides may also be referred to herein as "polypeptide analogs." As used herein a "derivative" of a polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "polynucleotide" is intended to encompass a singular nucleic acid as well as plural nucleic acids, and refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a therapeutic polypeptide contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of the present invention, as well as positive and negative strand forms, and double-stranded forms, of pestivirus vectors disclosed herein.

Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' non-translated regions, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a vector of the present invention may encode one or more polyproteins, which are post- or co-translationally separated into the final proteins via proteolytic cleavage. In addition, a vector, polynucleotide, or nucleic acid of the invention may encode heterologous coding regions, either fused or unfused to a first or second nucleic acid encoding of the invention, or variant or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid, which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions, which function in vertebrate cells, such as, but not limited to, promoter and enhancer segments from cytomegaloviruses (e.g., the immediate early promoter, in conjunction with intron-A), simian virus 40 (e.g., the early promoter), and retroviruses (such as, e.g., Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence).

In other embodiments, a polynucleotide of the present invention is RNA, for example, in the form of messenger RNA (mRNA). RNA of the present invention may be single stranded or double stranded.

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

The term "construct" refers to an engineered vector.

The term "artificial" refers to a synthetic, or non-host cell derived composition, e.g., a chemically-synthesized oligonucleotide.

As discussed in more detail below, a functional antigen-loaded soluble fragment of a CD1d polypeptide, including both CD1d and β-2 microglobulin subunits, is referred to herein as a "soluble CD1d complex." The antigen to be loaded onto the CD1d polypeptide is a glycolipid, typically a ceramide-like glycolipid, e.g., an alpha-galctosylceramide, e.g., α-GalCer. "Ceramide-like glycolipids," as referred to herein include glycolipids with α-linked galactose or glucose. Examples of glycolipid antigens which bind to CD1d are found, e.g., in Porcelli, U.S. Patent Appl. Publ. No. 2006/0052316, Tsuji, U.S. Patent Appl. Publ. No. 2006/0211856, Jiang, U.S. Patent Appl. Publ. No. 2006/0116331, Hirokazu et al., U.S. Patent Appl. Publ. No. 2006/0074235, Tsuji et al, U.S. Patent Appl. Publ. No. 2005/0192248, Tsuji, U.S. Patent Application No. 2004/0127429, and Tsuji et al., U.S. Patent Application No. 2003/0157135, all of which are incorporated by reference herein in their entireties.

The term "non-specific soluble CD1d complex" refers to a soluble CD1d complex which has not been engineered to be targeted to any specific organ, tissue, cell, or cell-surface molecule. A "non-specific soluble CD1d complex" is, however, capable of interacting with NKT cells, in a way similar to that in which a cell-surface-expressed CD1d molecule, when loaded with antigen, would interact. In contrast to a "non-specific soluble CD1d complex" is a "targeted CD1d complex," which is fused or conjugated to an antibody or other binding molecule, thus targeting the complex to a specific organ, tissue, cell, or cell-surface marker. Targeted CD1d complexes exert their effect on NKT cells locally, e.g., in the vicinity of a tumor. See, e.g., Bruno et al. U.S. Patent Appl. Publ. No. 2006/0269540, incorporated herein by reference in its entirety.

Antibodies are constructed of one, or several, units, each of which consists of two heavy (H) polypeptide chains and two light (L) polypeptide chains. The H and L chains are made up of a series of domains. The L chains, of which there are two major types (κ and λ), consists of two domains. The H chains are of several types, including μ, δ, and γ (of which there are several subclasses), α and ε. In humans, there are eight genetically and structurally identified antibody classes and subclasses as defined by heavy chain isotypes: IgM, IgD, IgG3, IgG1, IgG2, IgG4, IgE, and IgA. Further, for example, "IgG" means an antibody of the G class, and that, "IgG1" refers to an IgG molecules of subclass 1 of the G class. IgG1 antibodies, like all antibodies of the IgG class, are comprised of 4 domains, one of which is variable and the other 3 are constant. An Fab antibody fragment is comprised of an intact light chain and a truncated heavy chain that each comprise two domains, one variable and one constant.

As used herein, the term "antibody" (Ab) or "monoclonal antibody" (MAb) is meant to include intact molecules as well as antibody portions (such as, for example, Fab and F(ab')2 portions and Fv fragments) which are capable of specifically binding to a cell surface marker. Such portions are typically produced by proteolytic cleavage, using enzymes such as papain (to produce Fab portions) or pepsin (to produce F(ab')2 portions). Especially preferred in the compounds of the invention are Fab portions. Alternatively, antigen-binding portions can be produced through the application of recombinant DNA technology.

In addition, the immunoglobin may be a single chain antibody ("SCA"). These may consist of single chain Fv fragments ("scFv") in which the variable light ("V[L]") and variable heavy ("V[H]") domains are linked by a peptide bridge or by disulfide bonds. Also, the immunoglobulin may consist of single V[H]domains (dAbs) which possess antigen-binding activity. See, e.g., G. Winter and C. Milstein, Nature 349:295 (1991); R. Glockshuber et al., Biochemistry 29:1362 (1990); and, E. S. Ward et al., Nature 341:544 (1989).

Also preferred for use in the present invention are chimeric monoclonal antibodies, preferably those chimeric antibodies having specificity toward a tumor associated surface membrane antigen, a surface membrane antigen of a tissue or organ affected by autoimmune disease, or an antigen of a pathogen infected cell. As used in this example, the term "chimeric antibody" refers to a monoclonal antibody comprising a variable region, i.e. binding region, from one source or species and at least a portion of a constant region derived from a different source or species, usually prepared by recombinant DNA techniques.

Encompassed by the term "chimeric antibody" is the concept of "humanized antibody", that is those antibodies in which the framework or "complementarity" determining regions ("CDR") have been modified to comprise the CDR of an immunoglobulin of different specificity as compared to that of the parent immunoglobulin. In certain embodiments, a murine CDR is grafted into the framework region of a human antibody to prepare the "humanized antibody". See, e.g., L. Riechmann et al., Nature 332:323 (1988); M. S. Neuberger et al., Nature 314:268 (1985).

In other embodiments, fully human antibodies or fragments thereof are used in the compositions and methods of the invention, preferably those fully human antibodies having specificity toward a tumor associated surface membrane antigen, a surface membrane antigen of a tissue or organ affected by autoimmune disease, or an antigen of a pathogen infected cell. Methods have been described for selection of fully human antibodies in human immunoglobulin transgenic mice, from libraries of human immunoglobulin genes constructed in phage and expressed in bacteria or constructed in a mammalian viral expression vector for expression in mammalian cells, and from human hybridoma cells. A method for selection of fully human antibodies from libraries of human immunoglobulin genes constructed in vaccinia virus is described in Zauderer, M. et al. WO 01/72995, published 4 Oct. 2001, the disclosure of which is incorporated by reference herein.

In certain embodiments, targeted CD1d complexes of the present invention comprise, instead of, or in addition to an antibody, a specific binding molecule, e.g., a receptor or ligand that has a matching or counterpart ligand or receptor expressed on a cell surface of a target cell. In these embodiments, the targeted CD1d complex comprises a ligand or receptor specific for a cell surface marker. Examples include: CD4 coupled to CD1d for interaction with HIV infected cells; chemokine or chemokine receptor coupled to CD1d for interaction with DC subset; or hereguilins coupled to CD1d for interaction with ErbB2 positive tumor cells.

In one embodiment, the antibody is specific for a cell surface marker of a tumor cell. In another embodiment, the antibody is specific for a cell surface marker of a CD1d-restricted NKT cell. In another embodiment, the antibody is specific for a cell surface marker of a target tissue of autoimmune disease or inflammatory response. In another embodiment, the antibody is specific for an infectious agent or a cell surface marker of an infected cell or tissue.

In another embodiment, the antibody is specific for a cell surface marker of a professional antigen presenting cell, e.g., a dendritic cell.

The term "antigen" and the related term "antigenic" as used herein refers to a substance that binds specifically to an antibody or to a T-cell receptor.

The term "immunogen" and the related term "immunogenic" as used herein refers to the ability to induce an immune response, including an antibody and/or a cellular immune response in an animal, preferably a mammal. It is quite likely that an immunogen will also be antigenic, but an "antigen," because of its size or conformation, may not necessarily be an "immunogen." An "immunogenic composition" induces an immune response in a subject, e.g., antibodies that specifically recognize one or more antigens, contained within that "immunogenic composition."

The term "immune response" is meant to include any activity of cells of the immune system in response to an antigen or immunogen. Such activities include, but are not limited to production of antibodies, cytotoxicity, lymphocyte proliferation, release of cytokines, inflammation, phagocytosis, antigen presentation, and the like. An immune response which is highly specific to a given antigen or immunogen, e.g., production of specific antibodies or production of specific T lymphocytes is referred to herein as an "adaptive immune response." An immune response which is not specific to a given antigen, e.g., release of cytokines by NK and NKT cells, is referred to herein an "innate immune response." Examples of immune responses include an antibody response or a cellular, e.g., cytotoxic T-cell, response.

The terms "protective immune response" or "therapeutic immune response" refer to an immune response to an immunogen which in some way prevents or at least partially arrests disease symptoms, side effects or progression. By "protective" is meant that the immune response is induced in a subject animal which has not contracted a disease, where the immune response alleviates, reduces, moderates or, in some cases fully prevents disease symptoms if the animal later contracts or is suceptible to that disease. By "therapeutic" is meant that the immune response is induced in a subject animal which has the disease, where the immune response alleviates, reduces, moderates, or in some cases fully eliminates disease symptoms.

The term "modulating an immune response" is meant to refer to any way in which a given immune response is increased, decreased, or changed by a composition or treatment relative to the immune response without that composition or treatment. For example, use of an adjuvant to increase an immune response to an antigen is considered modulation of that immune response. Decrease in an immune response, e.g., prevention of autoimmunity, is also a modulation. In addition, changing an immune response, e.g., from a TH2 response to a TH1 response, is a modulation of an immune response.

The term "anergy" refers to a specific kind if immune modulation, in which certain cells of the immune system are rendered non-responsive to antigen stimulus. An example would be the ability of free α-GalCer, upon multiple administrations to an animal, to render the NKT cells of that animal non-responsive to stimulus, e.g., unable to proliferate or produce cytokines.

The term "adjuvant" refers to any material having the ability to (1) alter or increase the immune response to a particular antigen or (2) increase or aid an effect of a pharmacological agent. In certain embodiments, a soluble CD1d complex of the present invention, e.g., a non-specific soluble CD1d complex, functions as an adjuvant upon administration with an immunogen. Other suitable adjuvants include, but are not limited to, cytokines and growth factors; bacterial components (e.g., endotoxins, in particular superantigens, exotoxins and cell wall components); aluminum-based salts; calcium-based salts; silica; polynucleotides; toxoids; serum proteins, viruses and virally-derived materials, poisons, venoms, imidazoquiniline compounds, poloxamers, and cationic lipids.

A great variety of materials have been shown to have adjuvant activity through a variety of mechanisms. Any compound which may increase the expression, antigenicity or immunogenicity of the polypeptide is a potential adjuvant. Potential adjuvants include, but are not limited to: inert carriers, such as alum, bentonite, latex, and acrylic particles; pluronic block polymers, such as TiterMax® (block copolymer CRL-8941, squalene (a metabolizable oil) and a microparticulate silica stabilizer), depot formers, such as Freunds adjuvant, surface active materials, such as saponin, lysolecithin, retinal, Quil A, liposomes, and pluronic polymer formulations; macrophage stimulators, such as bacterial lipopolysaccharide; alternate pathway complement activators, such as insulin, zymosan, endotoxin, and levamisole; and non-ionic surfactants, such as poloxamers, poly(oxyethylene)-poly(oxypropylene) tri-block copolymers.

In certain embodiments, the adjuvant is a cytokine. A composition of the present invention can comprise one or more cytokines, chemokines, or compounds that induce the production of cytokines and chemokines. Examples include, but are not limited to granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFNα), interferon beta (IFNβ), interferon gamma (IFNγ), interferon omega (IFNω), interferon tau (IFNτ), interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), Leishmania elongation initiating factor (LEIF), and Flt-3 ligand.

The term "vertebrate" is intended to encompass a singular "vertebrate" as well as plural "vertebrates" and comprises mammals and birds, as well as fish, reptiles, and amphibians.

The term "mammal" is intended to encompass a singular "mammal" and plural "mammals," and includes, but is not limited to humans; primates such as apes, monkeys (e.g., owl, squirrel, cebus, rhesus, African green, patas, cynomolgus, and cercopithecus), orangutans, baboons, gibbons, and chimpanzees; canids such as dogs and wolves; felids such as cats, lions, and tigers; equines such as horses, donkeys, and zebras, food animals such as cows, pigs, and sheep; ungulates such as deer and giraffes; ursids such as bears; and others such as rabbits, mice, ferrets, seals, whales. In particular, the mammal can be a human subject, a food animal or a companion animal.

The term "bird" is intended to encompass a singular "bird" and plural "birds," and includes, but is not limited to feral water birds such as ducks, geese, terns, shearwaters, and gulls; as well as domestic avian species such as turkeys, chickens, quail, pheasants, geese, and ducks. The term "bird" also encompasses passerine birds such as starlings and budgerigars.

Soluble CD1d Complexes

As mentioned above, soluble CD1d complexes of the present invention can be used both to prevent a disease, and also to therapeutically treat a disease. In individuals already suffering from a disease, the present invention is used to further stimulate or modulate the immune system of the animal, thus reducing or eliminating the symptoms associated with that disease or disorder. As defined herein, "treatment" refers to the use of one or more compositions of the present invention to prevent, cure, retard, or reduce the severity of given disease symptoms in an animal, and/or result in no worsening of the disease over a specified period of time in an animal which has already contracted the disease and is thus in need of therapy. The term "prevention" refers to the use of one or more compositions of the present invention to generate immunity in an animal which has not yet contracted a disease, thereby preventing or reducing disease symptoms if the vertebrate is later disposed to develop that disease. The methods of the present invention therefore may be referred to as therapeutic methods or preventative or prophylactic methods. It is not required that any composition of the present invention provide total immunity to a disease agent or totally cure or eliminate all disease symptoms. As used herein, an "animal in need of therapeutic and/or preventative immunity" refers to an individual for whom it is desirable to treat, i.e., to prevent, cure, retard, or reduce the severity of certain disease symptoms, and/or result in no worsening of disease over a specified period of time.

The present invention provides methods of modulating an immune response comprising administering to an animal a composition which comprises an antigen-loaded soluble CD1d molecule, which interact with, and thereby affects, the activity of CD1d-restricted NKT cells. The monomorphic CD1d molecule is suitable for activation of a broad spectrum of CD1d-restricted NKT in an entire species. Soluble CD1d molecules, which include both CD1d and β-2 microglobulin subunits, are loaded with a ceramide-like glycolipid antigen, for example, α-GalCer, to produce a soluble CD1d complex. Soluble CD1d complexes of the present invention, e.g., non-specific soluble CD1d complexes, can be the primary or only active ingredient in a composition of the present invention, for example for treatment of cancer. In other embodiments, soluble CD1d complexes of the present invention may be used as an adjuvant in combination with a specific immunogen, thereby, stimulating, increasing, modulating, or otherwise altering an immune response to that immunogen relative to administration of the immunogen without the soluble CD1d complex. The present invention further encompasses pharmaceutical compositions which comprise an immunogen and a soluble CD1d complex adjuvant.

Moreover, soluble CD1d complexes of the present invention may be used as a diagnostic or therapeutic agent not only for cancer and infectious diseases but also for a large class of autoimmune and inflammatory diseases that result from a failure to down modulate cell-mediated immune responses.

Soluble CD1d complexes for use in the methods of the present invention comprise a soluble fragment of a CD1d polypeptide sufficient to bind β2-microglobulin as well as a ceramide-like glycolipid antigen, a β2-microglobulin polypeptide, and a ceramide-like glycolipid antigen, e.g., α-GalCer. The ceramide-like glycolipid antigen is bound in the antigen binding groove of the CD1d molecule.

As taught by WO 9964597, published 16 Dec. 1999 and incorporated herein by reference, it is possible to introduce mutations into β2-microglobulin that increase affinity for the class I heavy chain so as to facilitate assembly and increase stability of the CD1d complex in the fusion protein. In certain embodiments, a soluble CD1d polypeptide is linked to β2-microglobulin as a fusion protein. In certain embodiments, the β2-microglobulin polypeptide is linked via its C-terminus to the N-terminus of the soluble CD1d polypeptide. Such fusion constructs can be made using conventional recombinant nucleic acid techniques. The fusion may be direct or may contain spacers. A short linker amino acid sequence may be inserted between the CD1d polypeptide and the β2-microglobulin polypeptide. If a linker sequence is included, this sequence will preferably contain at least 3 and not more than 30 amino acids. More preferably, the linker is about 5, 6, 7, 8, 9, 10, 11, 12, 13, 14, 15, 20, or 25 amino acids long. Generally, the linker consists of short glycine/serine spacers, but any known amino acid may be used. Examples of linkers known to those skilled in the art include (Gly$_4$Ser)$_3$ (SEQ ID NO:3) and (Gly$_4$Ser)$_2$ Gly$_3$AlaSer (SEQ ID NO:4).

Alternatively, the CD1d and β2-microglobulin polypeptides may be chemically linked. A number of reagents capable of cross-linking proteins are known in the art, illustrative entities include: azidobenzoyl hydrazide, N-[4-(p-azidosalicylamino)butyl]-3'-[2'-pyridyldithio]propionamide), bis-sulfosuccinimidyl suberate, dimethyladipimidate, disuccinimidyltartrate, N-γ-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, formaldehyde and succinimidyl 4-[N-maleimidomethyl]cyclohexane-1-carboxylate.

In certain embodiments, multiple CD1d complexes are linked together through a multivalent compound. The CD1d complexes may be linked to the multivalent compound through any site. In a preferred embodiment soluble CD1d polypeptides are linked to the multivalent compound through the CD1d carboxyl terminus. These compounds typically comprise 2 or more CD1d complexes. The compounds may comprise 2, 3, 4, 5, 6, 7, 8, 9 or 10 CD1d complexes.

Examples of multivalent compounds are chicken avidin or streptavidin (Shin, S. U. et al., *J. Immunology* 158: 4797-4804 (1997)) to which biotinylated CD1d complexes are bound (Altman, J. et al, *Science* 274:94-96 (1996); Boniface, J. J. et al., *Immunity* 9:459-66 (1998)); or a leucine zipper system.

Alternatively, CD1d and β2-microglobulin polypeptides can be genetically modified by including sequences encoding amino acid residues with chemically reactive side chains such as Cys or His. Such amino acids with chemically reactive side chains may be positioned in a variety of positions on the CD1d and β2-microglobulin polypeptides, preferably distal to the site(s) where β2-microglobulin and CD1d interact. Suitable side chains can be used to chemically link two or more assembled CD1d complexes to a suitable dendrimer particle. Dendrimers are synthetic chemical polymers that can have any one of a number of different functional groups on their surface (D. Tomalia, Aldrichimica Acta 26:91:101 (1993)). Exemplary dendrimers for use in accordance with the present invention include e.g. E9 starburst polyamine dendrimer and E9 combburst polyamine dendrimer, which can link cysteine residues. The CD1d and/or β2-microglobulin polypeptides are modified to introduce a cysteine residue at the carboxyl terminus. Following synthesis in eukaryotic cells, a complete cysteine modified CD1d complex is assembled in vitro. Cysteine modified CD1d and/or β2-microglobulin polypeptides will react with the maleimide groups on the various peptide backbones with either two, three, or four modified lysine residues for formation of CD1d dimers, trimers, and tetramers.

Cochran, J. R. et al., *Immunity* 12:241-50 (2000) describe the use of chemically synthesized peptide-based cross-linking reagents in which two or more thiol-reactive maleimide groups are linked to lysine side chains in a flexible peptide of 8 to 19 residues containing glycine, serine, and glutamic acid in addition to the modified lysine residues. Isolated CD1d and/or β2-microglobulin polypeptides are modified to introduce a cysteine residue at the carboxyl terminus. Cysteine modified CD1d and/or β2-microglobulin polypeptides react with the maleimide groups on the various peptide backbones with either two, three, or four modified lysine residues for formation of dimers, trimers, and tetramers.

Another means of assembling polymeric CD1d complexes is to exploit the observation that defined amino acid substitutions in the GCN4 leucine zipper dimerization domain results in formation of highly stable trimeric and tetrameric structures of the synthetic peptide (Harbury, P. B. et al., *Science* 262:1401-7 (1993)). For example, multivalent CD1d complexes are constructed by attaching a modified GCN4-zipper to the carboxyl terminus of soluble CD1d or β2-microglobulin polypeptides. Tetravalent CD1d complexes could be assembled from a mixture of CD1d complexes each separately fused to a modified GCN4-zipper motif.

The attachment site(s) on a soluble CD1d complex for binding to a multivalent compound may be naturally occurring, or may be introduced through genetic engineering. The site will be a specific binding pair member or one that is modified to provide a specific binding pair member, where the complementary pair has a multiplicity of specific binding sites. Binding to the complementary binding member can be a chemical reaction, epitope-receptor binding or hapten-receptor binding where a hapten is linked to the subunit chain.

In a preferred embodiment, the CD1d and/or β2 microglobulin contain an amino acid sequence which is a recognition site for a modifying enzyme. Modifying enzymes include BirA, various glycosylases, farnesyl protein transferase, and protein kinases. The group introduced by the modifying enzyme, e.g. biotin, sugar, phosphate, farnesyl, etc. provides a complementary binding pair member, or a unique site for further modification, such as chemical cross-linking, biotinylation, etc. that will provide a complementary binding pair member.

For example, the CD1d molecule may be engineered to contain a site for biotinylation, for example a BirA-dependent site. The multivalent compound can be avidin or can be linked to avidin either directly or indirectly.

Both the soluble CD1d and β2-microglobulin polypeptides useful in the present invention may be autologous to any mammalian or avian species, for example, primates (esp. humans), rodents, rabbits, equines, bovines, canines, felines, etc. β2-microglobulin is typically not inflammatory in vivo. However, it is preferable to employ β2-microglobulin derived from the same species as is to be treated so as to reduce the risk of a xenogeneic immune response.

Soluble CD1d Polypeptides

In certain embodiments, the non-specific CD1d complex comprises soluble CD1d polypeptides and polypeptide fragments, which associates with $\beta_2$-microglobulin and binds antigen, e.g., ceramide-like glycolipid. The CD1d molecule is a member of the family of major histocompatibility complex (MN+HC) antigen-like glycoproteins which associate with $\beta_2$-microglobulin and are expressed at the surface of cortical thymocytes, B cells, dendritic cells, Langerhans cells in the skin, and gastrointestinal epithelial cells. CD1d is mainly expressed on dendritic cells or epithelial cells of the gastrointestinal tract. The CD1 family members are involved in the presentation of glycolipids as antigens. In particular, CD1d regulates cytokine tone through activation of a distinct subset of T-lymphocytes, namely NK1 T cells which secrete IL-4 and INF-β. All of the CD1 glycoproteins have been cloned and analyzed. For a detailed discussion of CD1 glycoproteins, and in particular CD1d, see, e.g., Balk et al., *Proc. Natl. Acad. Sci. USA* 86:252-256 (1989); Kojo et al., *Biochem. Biophy. Res. Comm.* 276:107-111 (2000); Kojo et al., *J. Rheumatology* 30:2524-2528 (2003); Kang and Cresswell, *Nature Immunology* 5:175-181 (2004); Im et al., *J. Biol. Chem.* 279:299-310 (2004); Dutronc and Porcelli, *Tissue Antigens* 60:337-353 (2002) which are incorporated by reference herein in their entirety.

Domains of CD1d

Full-length CD1d consists of a signal sequence, an extracellular domain, a transmembrane domain and a cytoplasmic domain. The full-length CD1d polypeptide is 335 amino acids in length.

The following polypeptide sequence was reported as the human CD1d sequence and has the accession number NP_001757 in Genbank.

Full-Length Human CD1d (SEQ ID NO:1):

```
MGCLLFLLLW ALLQAWGSAE VPQRLFPLRC LQISSFANSS

WTRTDGLAWL GELQTHSWSN DSDTVRSLKP WSQGTFSDQQ

WETLQHIFRV YRSSFTRDVK EFAKMLRLSY PLELQVSAGC

EVHPGNASNN FFHVAFQGKD ILSFQGTSWE PTQEAPLWVN

LAIQVLNQDK WTRETVQWLL NGTCPQFVSG LLESGKSELK

KQVKPKAWLS RGPSPGPGRL LLVCHVSGFY PKPVWVKWMR

GEQEQQGTQP GDILPNADET WYLRATLDVV AGEAAGLSCR

VKHSSLEGQD IVLYWGGSYTSMGLIALAVL ACLLFLLIVG

FTSRFKRQTS YQGVL
```

A variant of human CD1d includes, but is not limited to, a polypeptide with the following mutation:T64S.

The sequence of mouse CD1d can be found on Genbank with the following accession number: NP_031665. The sequence of rat CD1d can be found on Genbank with the following accession number: NP_058775. The sequence of sheep CD1d can be found on Genbank with the following accession numbers: O62848 and Q29422. The sequence of chimpanzee CD1d can be found on Genbank with the following accession number: NP_001065272. The sequence of rabbit CD1d can be found on Genbank with the following accession number: P23043. All of the above Genbank accession numbers are incorporated herein by reference.

The accession number was reported as the mouse CD1d: NP_031665 in Genbank.

The extracellular domain of CD1d consists of three domains: the α1 domain, the α2 domain, and the α3 domain. The α1 and α2 domains comprise the antigen binding sites. The α3 domain includes a $\beta_2$-microglobulin association site.

The CD1d domain designations used herein are defined as follows:

TABLE 1

| CD1d domains | |
|---|---|
| Domain | CD1d (human) |
| Signal Seq. | 1-19 |
| Extracellular | 20-301 |
| α1 domain | 20-108 |
| α2 domain | 109-201 |
| α3 domain | 202-295 |
| Transmembrane | 302-322 |
| Cytoplasmic | 323-335 |

As one of skill in the art will appreciate, the beginning and ending residues of the domains listed above may vary depending upon the computer modeling program used or the method used for determining the domain.

Some embodiments of the invention provide a CD1d complex, e.g., a non-specific CD1d complex, which comprises a soluble CD1d polypeptide or polypeptide fragment. Specifically, soluble CD1d polypeptides of the present invention include fragments, variants, or derivative thereof of a soluble CD1d polypeptide. Table 1 above describes the various domains of the CD1d polypeptide. Soluble CD1d polypeptides of the invention generally comprise a portion or all of the extracellular domain of the polypeptides, including the α1, α2, and α3 domains. Soluble CD1d polypeptides generally lack some or all of the transmembrane domain and cytoplasmic domain. As one of skill in the art would appreciate, the entire extracellular domain of CD1d may comprise additional or fewer amino acids on either the C-terminal or N-terminal end of the extracellular domain polypeptide.

Soluble human CD1d polypeptides for use in the methods of the present invention include, but are not limited to, a soluble CD1d polypeptide comprising, consisting essentially of, or consisting of an amino acid sequence identical to a reference amino acid sequence, except for up to twenty amino acid substitutions, wherein said reference amino acid sequence is selected from the group consisting of amino acids a to 295 of SEQ ID NO:1, amino acids 21 to b of SEQ ID NO:1, and a to b of SEQ ID NO:1, wherein a is any integer from 1 to 100, and b is any integer from 201 to 301, and wherein said soluble CD1d polypeptide associates with $\beta_2$-microglobulin and binds a ceramide-like glycolipid antigen. In one embodiment, the soluble CD1d polypeptide comprises amino acids 21 to 295 of SEQ ID NO:1. In another embodiment, the soluble CD1d polypeptide comprises amino acids 20-295, 20-296, 20-297, 20-298, 20-299, 20-300 and 20 to 301 of SEQ ID NO:1.

By "a reference amino acid sequence" is meant the specified sequence without the introduction of any amino acid substitutions. As one of ordinary skill in the art would understand, if there are no substitutions, the "isolated polypeptide" of the invention comprises an amino acid sequence which is identical to the reference amino acid sequence.

Soluble CD1d polypeptides described herein may have various alterations such as substitutions, insertions or deletions. Exemplary amino acids that can be substituted in the polypeptide include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Corresponding fragments of soluble CD1d polypeptides at least 70%, 75%, 80%, 85%, 90%, or 95% identical to the polypeptides and reference polypeptides described herein are also contemplated.

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wisc. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

In methods of the present invention, a soluble CD1d polypeptide or polypeptide fragment of the invention may be administered directly as a preformed polypeptide. In certain embodiments, however, the soluble CD1d polypeptide or fragment thereof is associated with $\beta_2$-microglobulin, and is bound to a ceramide-like glycolipid antigen.

$\beta_2$-Microglobulin Polypeptides

In certain embodiments, a CD1d complex of the invention comprises a $\beta_2$-microglobulin polypeptide, which associates with a soluble CD1d polypeptide or polypeptide fragment. $\beta_2$-microglobulin is present on the surface of all nucleated cells as the small extracellular subunit of the major histocompatibility complex (MHC) class I molecule and actively participates in the immune response. For a detailed discussion of $\beta_2$-microglobulin, see, e.g., Peterson et al., *Adv. Cancer Res.* 24:115-163 (1977); Sege et al., *Biochemistry* 20:4523-4530 (1981); which are incorporated by reference herein in their entirety.

$\beta_2$-Microglobulin Domains

Full-length $\beta_2$-microglobulin is a secreted protein which comprises a signal sequence and Ig-like domain. The full-length CD1d polypeptide is 119 amino acids in length.

The following polypeptide sequence was reported as the human $\beta_2$-microglobulin sequence and has the accession number NP_004039 in Genbank.

Full-Length Human $\beta_2$-microglobulin (SEQ ID NO:2):

```
MSRSVALAVL ALLSLSGLEA IQRTPKIQVY SRHPAENGKS

NFLNCYVSGF HPSDIEVDLL KNGERIEKVE HSDLSFSKDW

SFYLLYYTEF TPTEKDEYAC RVNHVTLSQP KIVKWDRDM
```

Variants of human $\beta_2$-microglobulin include, but are not limited to, polypeptides with one or more of the following mutations: A20G, P52Q, S55V, and Y86YS.

The sequence of mouse $\beta_2$-microglobulin can be found on Genbank with the following accession number: NP_033865. The sequence of pig $\beta_2$-microglobulin can be found on Genbank with the following accession number: NP_999143. The sequence of rat $\beta_2$-microglobulin can be found on Genbank with the following accession number: NP_036644. The sequence of chimpanzee $\beta_2$-microglobulin can be found on Genbank with the following accession number: NP_001009066. The sequence of rabbit $\beta_2$-microglobulin can be found on Genbank with the following accession number:P01885. The sequence of sheep $\beta_2$-microglobulin can be found on Genbank with the following accession number: NP_001009284.

The $\beta_2$-microglobulin domain designations used herein are defined as in Table 2:

TABLE 2

| $\beta_2$-microglobulin domains | |
|---|---|
| Domain | $\beta_2$-microglobulin (human) |
| Signal Seq. | 1-20 |
| $\beta_2$-microglobulin | 21-119 |
| Ig domain | 25-113 or 22-116 |

As one of skill in the art will appreciate, the beginning and ending residues of the domains listed above may vary depending upon the computer modeling program used or the method used for determining the domain.

Some embodiments of the invention provide a CD1d complex, e.g., a non-specific CD1d complex, which comprises a $\beta_2$-microglobulin polypeptide or polypeptide fragment. $\beta_2$-microglobulin polypeptides of the present invention include fragments, variants, or derivative thereof of a $\beta_2$-microglobulin polypeptide. Table 2 above describes the various domains of the $\beta_2$-microglobulin polypeptide. $\beta_2$-microglobulin polypeptides of the invention generally comprise a portion or all of the secreted portion of the polypeptides.

Human $\beta_2$-microglobulin polypeptides for use in the methods of the present invention include, but are not limited to, a $\beta_2$-microglobulin polypeptide comprising, consisting essentially of, or consisting of an amino acid sequence identical to a reference amino acid sequence, except for up to twenty amino acid substitutions, wherein said reference amino acid sequence is selected from the group consisting of amino acids a to 119 of SEQ ID NO:2, amino acids 21 to b of SEQ ID NO: 2, and a to b of SEQ ID NO:2, wherein a is any integer from 15 to 25, and b is any integer from 100 to 119, wherein said $\beta_2$-microglobulin polypeptide associates with CD1d and supports binding of ceramide-like glycolipid antigens. In one embodiment, the $\beta_2$-microglobulin polypeptide comprises amino acids 21 to 113 of SEQ ID NO:2. In one embodiment, the $\beta_2$-microglobulin polypeptide comprises amino acids 21 to 119 of SEQ ID NO:2.

By "a reference amino acid sequence" is meant the specified sequence without the introduction of any amino acid substitutions. As one of ordinary skill in the art would understand, if there are no substitutions, the "isolated polypeptide" of the invention comprises an amino acid sequence which is identical to the reference amino acid sequence.

$\beta_2$-microglobulin polypeptides described herein may have various alterations such as substitutions, insertions or deletions. Exemplary amino acids that can be substituted in the polypeptide include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Corresponding fragments of $\beta_2$-microglobulin polypeptides at least 70%, 75%, 80%, 85%, 90%, or 95% identical to the polypeptides and reference polypeptides described herein are also contemplated.

In methods of the present invention, a $\beta_2$-microglobulin polypeptide or polypeptide fragment of the invention is typically administered directly as a preformed polypeptide. In certain embodiments, the $\beta_2$-microglobulin polypeptide or fragment thereof is associated with a soluble CD1d polypeptide.

A soluble CD1d polypeptide may contain some or all of the amino acids from the transmembrane domain, provided that the polypeptide is still capable of remaining soluble in an aqueous, e.g., a physiological solution. Preferably, not more than about 20, 19, 18, 17, 16, 15, 14, 13, 12, 11, 10, 9, 8, 7, 6, 5, 4, 3, 2 or 1, and preferably none of the amino acids of the transmembrane domain will be included.

Additionally, fragments of $\beta_2$-microglobulin are useful in the present invention. To be useful in the present invention, the fragment of $\beta_2$-microglobulin would have to retain the ability to associate with the CD1d molecule. Preferably, not more than about 20, 19, 18, 17, 16, 15, 14, 13, 12, 11, 10, 9, 8, 7, 6, 5, 4, 3, 2 or 1, and preferably none of the amino acids of $\beta_2$-microglobulin will be deleted.

One may wish to introduce a small number of amino acids at the polypeptide termini of either the soluble CD1d polypeptide or the $\beta_2$-microglobulin polypeptide, usually not more than 20, 19, 18, 17, 16, 15, 14, 13, 12, 11, 10, 9, 8, 7, 6, 5, 4, 3, 2 or 1. The deletion or insertion of amino acids will usually be as a result of the needs of the construction, providing for convenient restriction sites, addition of processing signals, ease of manipulation, improvement in levels of expression, or the like. In addition, one may wish to substitute one or more amino acids with a different amino acid for similar reasons, usually not substituting more than about 10, 9, 8, 7, 6, 5, 4, 3, 2 or 1 amino acids in any one domain.

The soluble CD1d polypeptide and $\beta_2$-microglobulin polypeptide may be separately produced and allowed to associate to form a stable heteroduplex complex, or both of the subunits may be expressed in a single cell.

Soluble CD1d polypeptides and $\beta_2$-microglobulin polypeptides for use in the methods and compositions of the present invention may be isolated from a multiplicity of cells, e.g., transformed cell lines JY, BM92, WIN, MOC, and MG, and CHO using a variety of techniques known to those skilled in the art.

Additionally, the amino acid sequences of CD1d and β2-microglobulin from a variety of species are known, and the polynucleotides encoding these polypeptides have been cloned, therefore, the polypeptides can be made using recombinant methods. The coding regions for the CD1d and $\beta_2$ microglobulin chains or their fusion products are inserted into expression vectors, expressed separately in an appropriate host, such as E. coli, yeast, insect cells, mammalian cells or other suitable cells, and the recombinant proteins obtained are recombined in the presence of a ceramide like glycolipid antigen (e.g. α-GalCer).

Fusion Proteins, Modified Proteins and Conjugated Polypeptides

Some embodiments of the invention involve the use of a soluble CD1d polypeptide and/or $\beta_2$-microglobulin polypeptide fused to a heterologous polypeptide moiety to form a fusion protein. Such fusion proteins can be used to accomplish various objectives, e.g., increased serum halflife, improved bioavailability, in vivo targeting to a specific organ or tissue type, improved recombinant expression efficiency, improved host cell secretion, ease of purification, and higher avidity. Depending on the objective(s) to be achieved, the heterologous moiety can be inert or biologically active. Also, it can be chosen to be stably fused to the soluble CD1d polypeptide or $\beta_2$-microglobulin polypeptide of the invention or to be cleavable, in vitro or in vivo. Heterologous moieties to accomplish these other objectives are known in the art.

As an alternative to expression of a fusion protein, a chosen heterologous moiety can be preformed and chemically conjugated to the soluble CD1d polypeptide or $\beta_2$-microglobulin polypeptide of the invention. In most cases, a chosen heterologous moiety will function similarly, whether fused or conjugated to the soluble CD1d polypeptide or $\beta_2$-microglobulin polypeptide. Therefore, in the following discussion of heterologous amino acid sequences, unless otherwise noted, it is to be understood that the heterologous sequence can be joined to the soluble CD1d polypeptide or $\beta_2$-microglobulin polypeptide in the form of a fusion protein or as a chemical conjugate.

Soluble CD1d polypeptides or $\beta_2$-microglobulin polypeptides for use in the treatment methods disclosed herein include derivatives that are modified, i.e., by the covalent attachment of any type of molecule such that covalent attachment does not prevent the soluble CD1d polypeptide and $\beta_2$-microglobulin polypeptide from associating and binding antigen to form a CD1d complex, e.g., a non-specific CD1d complex. For example, but not by way of limitation, the soluble CD1d polypeptides and/or $\beta_2$-microglobulin polypeptides of the present invention may be modified e.g., by glycosylation, acetylation, pegylation, phosphylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Soluble CD1d polypeptides or $\beta_2$-microglobulin polypeptides for use in the treatment methods disclosed herein can be composed of amino acids joined to each other by peptide bonds or modified peptide bonds, i.e., peptide isosteres, and may contain amino acids other than the 20 gene-encoded amino acids. Soluble CD1d polypeptides and/or $\beta_2$-microglobulin polypeptides may be modified by natural processes, such as posttranslational processing, or by chemical modification techniques which are well known in the art. Such modifications are well described in basic texts and in more detailed monographs, as well as in a voluminous research literature. Modifications can occur anywhere in the soluble CD1d polypeptides or $\beta_2$-microglobulin polypeptide including the peptide backbone, the amino acid side-chains and the amino or carboxyl termini, or on moieties such as carbohydrates. It will be appreciated that the same type of modification may be present in the same or varying degrees at several sites in a given soluble CD1d polypeptides or $\beta_2$-microglobulin polypeptide. Also, a given soluble CD1d polypeptides or $\beta_2$-microglobulin polypeptide may contain many types of modifications. Soluble CD1d polypeptides or $\beta_2$-microglobulin polypeptides may be branched, for example, as a result of ubiquitination, and they may be cyclic, with or without branching. Cyclic, branched, and branched cyclic soluble CD1d polypeptides or $\beta_2$-microglobulin polypeptides may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, *Proteins—Structure And Molecular Properties*, T. E. Creighton, W. H. Freeman and Company, New York 2nd Ed., (1993); *Posttranslational Covalent Modification Of Proteins*, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

A heterologous polypeptide to which the soluble CD1d polypeptides or $\beta_2$-microglobulin polypeptide is fused may be useful therapeutically or useful to target the soluble CD1d polypeptides and/or $\beta_2$-microglobulin polypeptide. Soluble CD1d fusion polypeptides and/or $\beta_2$-microglobulin fusion proteins can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the heterologous moiety can be inert or biologically active. Also, it can be chosen to be stably fused to the soluble CD1d polypeptides or $\beta_2$-microglobulin polypeptide or to be cleavable, in vitro or in vivo. Heterologous moieties to accomplish these various objectives are known in the art.

Various heterologous amino acid sequences, i.e., polypeptide moieties or "carriers," for increasing the in vivo stability, i.e., serum half-life, of therapeutic polypeptides are known. Examples include serum albumins such as, e.g., bovine serum albumin (BSA) or human serum albumin (HSA).

Due to its long half-life, wide in vivo distribution, and lack of enzymatic or immunological function, essentially full-length human serum albumin (HSA), or an HSA fragment, is commonly used as a heterologous moiety. Through application of methods and materials such as those taught in Yeh et al., *Proc. Natl. Acad. Sci. USA*, 89:1904-08 (1992) and Syed et al., *Blood* 89:3243-52 (1997), HSA can be used to form a fusion protein or polypeptide conjugate that displays pharmacological activity of a CD1d complex, e.g., a non-specific CD1d complex of the invention, while displaying significantly increased in vivo stability, e.g., 10-fold to 100-fold higher. The C-terminus of the HSA can be fused to the N-terminus of the soluble CD1d polypeptides or $\beta_2$-microglobulin polypeptide moiety. Since HSA is a naturally secreted protein, the HSA signal sequence can be exploited to obtain secretion of the fusion protein into the cell culture medium when the fusion protein is produced in a eukaryotic, e.g., mammalian, expression system.

Some embodiments of the invention employ a soluble CD1d polypeptide or $\beta_2$-microglobulin polypeptide moiety fused to a hinge and Fc region, i.e., the C-terminal portion of an immunoglobulin heavy chain constant region.

Potential advantages of a soluble CD1d polypeptide-Fc fusion or a $\beta_2$-microglobulin polypeptide-Fc fusion include solubility, in vivo stability, and multivalency, e.g., dimerization. The Fc region used can be an IgA, IgD, or IgG Fc region (hinge-CH2-CH3). Alternatively, it can be an IgE or IgM Fc region (hinge-CH2-CH3-CH4). An IgG Fc region is generally used, e.g., an IgG1 Fc region or IgG4 Fc region. Materials and methods for constructing and expressing DNA encoding Fc fusions are known in the art and can be applied to obtain fusions without undue experimentation. Some embodiments of the invention employ a fusion protein such as those described in Capon et al., U.S. Pat. Nos. 5,428,130 and 5,565,335.

Fully intact, wild-type Fc regions display effector functions that normally are unnecessary and undesired in an Fc fusion protein used in the methods of the present invention. Therefore, certain binding sites typically are deleted from the Fc region during the construction of the secretion cassette. For example, since coexpression with the light chain is unnecessary, the binding site for the heavy chain binding protein, Bip (Hendershot et al., *Immunol. Today* 8:111-14 (1987)), is deleted from the CH2 domain of the Fc region of IgE, such that this site does not interfere with the efficient secretion of the immunofusion. Transmembrane domain sequences, such as those present in IgM, also are generally deleted.

The IgG1 Fc region is most often used. Alternatively, the Fc region of the other subclasses of immunoglobulin gamma (gamma-2, gamma-3 and gamma-4) can be used in the secretion cassette. The IgG1 Fc region of immunoglobulin gamma-1 is generally used in the secretion cassette and includes at least part of the hinge region, the CH2 region, and the CH3 region. In some embodiments, the Fc region of immunoglobulin gamma-1 is a CH2-deleted-Fc, which includes part of the hinge region and the CH3 region, but not the CH2 region. A CH2-deleted-Fc has been described by Gillies et al., *Hum. Antibod. Hybridomas* 1:47 (1990). In some embodiments, the Fc region of one of IgA, IgD, IgE, or IgM, is used.

Soluble CD1d polypeptide-Fc fusion proteins or $\beta_2$-microglobulin-polypeptide-moiety-Fc fusion proteins can be constructed in several different configurations. In one configuration the C-terminus of the soluble CD1d or $\beta_2$-microglobulin polypeptide moiety is fused directly to the N-terminus of the Fc hinge moiety. In a slightly different configuration, a short polypeptide, e.g., 2-10 amino acids, is incorporated into the fusion between the N-terminus of the soluble CD1d or $\beta_2$-microglobulin polypeptide moiety and the C-terminus of the Fc moiety. In the alternative configuration, the short polypeptide is incorporated into the fusion between the C-terminus of the soluble CD1d or $\beta_2$-microglobulin polypeptide moiety and the N-terminus of the Fc moiety. Such a linker provides conformational flexibility, which may improve biological activity in some circumstances. If a sufficient portion of the hinge region is retained in the Fc moiety, the soluble CD1d polypeptide-Fc fusion or $\beta_2$-microglobulin-polypeptide-moiety-Fc fusion will dimerize, thus forming a divalent molecule. A homogeneous population of monomeric Fc fusions will yield monospecific, bivalent dimers. A mixture of two monomeric Fc fusions each having a different specificity will yield bispecific, bivalent dimers.

Soluble CD1d or $\beta_2$-microglobulin polypeptides of the invention can be fused to a polypeptide tag. The term "polypeptide tag," as used herein, is intended to mean any sequence of amino acids that can be attached to, connected to, or linked to a soluble CD1d or $\beta_2$-microglobulin polypeptide and that can be used to identify, purify, concentrate or isolate the soluble CD1d or $\beta_2$-microglobulin polypeptide. The attachment of the polypeptide tag to the soluble CD1d or $\beta_2$-microglobulin polypeptide may occur, e.g., by constructing a nucleic acid molecule that comprises: (a) a nucleic acid sequence that encodes the polypeptide tag, and (b) a nucleic acid sequence that encodes a soluble CD1d or $\beta_2$-microglobulin polypeptide. Exemplary polypeptide tags include, e.g., amino acid sequences that are capable of being post-translationally modified, e.g., amino acid sequences that are biotinylated. Other exemplary polypeptide tags include, e.g., amino acid sequences that are capable of being recognized and/or bound by an antibody (or fragment thereof) or other specific binding reagent. Polypeptide tags that are capable of being recognized by an antibody (or fragment thereof) or other specific binding reagent include, e.g., those that are known in the art as "epitope tags." An epitope tag may be a natural or an artificial epitope tag. Natural and artificial epitope tags are known in the art, including, e.g., artificial epitopes such as FLAG, Strep, or poly-histidine peptides. FLAG peptides include the sequence Asp-Tyr-Lys-Asp-Asp-Asp-Asp-Lys (SEQ ID NO:5) or Asp-Tyr-Lys-Asp-Glu-Asp-Asp-Lys (SEQ ID NO:6) (Einhauer, A. and Jungbauer, A., *J. Biochem. Biophys. Methods* 49:1-3:455-465 (2001)). The Strep epitope has the sequence Ala-Trp-Arg-His-Pro-Gln-Phe-Gly-Gly (SEQ ID NO:7). The VSV-G epitope can also be used and has the sequence Tyr-Thr-Asp-Ile-Glu-Met-Asn-Arg-Leu-Gly-Lys (SEQ ID NO:8). Another artificial epitope is a poly-His sequence having six histidine residues (His-His-His-His-His-His (SEQ ID NO:9). Naturally-occurring epitopes include the influenza virus hemagglutinin (HA) sequence Tyr-Pro-Tyr-Asp-Val-Pro-Asp-Tyr-Ala-Ile-Glu-Gly-Arg (SEQ ID NO:10) recognized by the monoclonal antibody 12CA5 (Murray et al., *Anal. Biochem.* 229:170-179 (1995)) and the eleven amino acid sequence from human c-myc (Myc) recognized by the monoclonal antibody 9E10 (Glu-Gln-Lys-Leu-Leu-Ser-Glu-Glu-Asp-Leu-Asn (SEQ ID NO:11) (Manstein et al., *Gene* 162:129-134 (1995)). Another useful epitope is the tripeptide Glu-Glu-Phe which is recognized by the monoclonal antibody YL 1/2. (Stammers et al. *FEBS Lett.* 283:298-302(1991)).

In certain embodiments, the soluble CD1d or $\beta_2$-microglobulin polypeptide and the polypeptide tag may be connected via a linking amino acid sequence. As used herein, a "linking amino acid sequence" may be an amino acid sequence that is capable of being recognized and/or cleaved by one or more proteases. Amino acid sequences that can be recognized and/or cleaved by one or more proteases are known in the art. Exemplary amino acid sequences include, but are not limited to, those that are recognized by the following proteases: factor VIIa, factor IXa, factor Xa, APC, t-PA, u-PA, trypsin, chymotrypsin, enterokinase, pepsin, cathepsin B,H,L,S,D, cathepsin G, renin, angiotensin converting enzyme, matrix metalloproteases (collagenases, stromelysins, gelatinases), macrophage elastase, Cir, and Cis. The amino acid sequences that are recognized by the aforementioned proteases are known in the art. Exemplary sequences recognized by certain proteases can be found, e.g., in U.S. Pat. No. 5,811,252.

Polypeptide tags can facilitate purification using commercially available chromatography media.

By fusing a soluble CD1d or $\beta_2$-microglobulin polypeptide moiety at the amino and carboxy termini of a suitable fusion partner, bivalent or tetravalent forms of a soluble CD1d or $\beta_2$-microglobulin polypeptide or polypeptide fragment of the invention can be obtained. For example, a soluble CD1d or $\beta_2$-microglobulin polypeptide moiety can be fused to the amino and carboxy termini of an Ig moiety to produce a bivalent monomeric polypeptide containing two soluble CD1d or $\beta_2$-microglobulin polypeptide moieties. Upon dimerization of two of these monomers, by virtue of the Ig moiety, a tetravalent form of a soluble CD1d or $\beta_2$-microglobulin polypeptide is obtained. Such multivalent forms can be used to achieve increased binding affinity for the target. Multivalent forms of a soluble CD1d or $\beta_2$-microglobulin polypeptide or polypeptide fragment of the invention also can be obtained by placing soluble CD1d or $\beta_2$-microglobulin polypeptide moieties in tandem to form concatamers, which can be employed alone or fused to a fusion partner such as Ig or HSA.

Conjugated Polymers (Other than Polypeptides)

Some embodiments of the invention involve a soluble CD1d or $\beta_2$-microglobulin polypeptide or polypeptide fragment of the invention wherein one or more polymers are conjugated (covalently linked) to the soluble CD1d or $\beta_2$-microglobulin polypeptide. Examples of polymers suitable for such conjugation include polypeptides (discussed above), sugar polymers and polyalkylene glycol chains. Typically, but not necessarily, a polymer is conjugated to the soluble CD1d or $\beta_2$-microglobulin polypeptide or polypeptide fragment of the invention for the purpose of improving one or more of the following: solubility, stability, or bioavailability.

The class of polymer generally used for conjugation to a soluble CD1d or $\beta_2$-microglobulin polypeptide or polypeptide fragment of the invention is a polyalkylene glycol. Polyethylene glycol (PEG) is most frequently used. PEG moieties, e.g., 1, 2, 3, 4 or 5 PEG polymers, can be conjugated to each soluble CD1d or $\beta_2$-microglobulin polypeptide to increase serum half life, as compared to the soluble CD1d or $\beta_2$-microglobulin polypeptide alone. PEG moieties are non-antigenic and essentially biologically inert. PEG moieties used in the practice of the invention may be branched or unbranched.

The number of PEG moieties attached to the soluble CD1d or $\beta_2$-microglobulin polypeptide and the molecular weight of the individual PEG chains can vary. In general, the higher the molecular weight of the polymer, the fewer polymer chains attached to the polypeptide. Usually, the total polymer mass attached to a soluble CD1d or $\beta_2$-microglobulin polypeptide or polypeptide fragment is from 20 kDa to 40 kDa. Thus, if one polymer chain is attached, the molecular weight of the chain is generally 20-40 kDa. If two chains are attached, the molecular weight of each chain is generally 10-20 kDa. If three chains are attached, the molecular weight is generally 7-14 kDa.

The polymer, e.g., PEG, can be linked to the soluble CD1d or $\beta_2$-microglobulin polypeptide through any suitable, exposed reactive group on the polypeptide. The exposed reactive group(s) can be, e.g., an N-terminal amino group or the epsilon amino group of an internal lysine residue, or both. An activated polymer can react and covalently link at any free amino group on the soluble CD1d or $\beta_2$-microglobulin polypeptide. Free carboxylic groups, suitably activated carbonyl groups, hydroxyl, guanidyl, imidazole, oxidized carbohydrate moieties and mercapto groups of the soluble CD1d or $\beta_2$-microglobulin polypeptide (if available) also can be used as reactive groups for polymer attachment.

In a conjugation reaction, from about 1.0 to about 10 moles of activated polymer per mole of polypeptide, depending on polypeptide concentration, is typically employed. Usually, the ratio chosen represents a balance between maximizing the reaction while minimizing side reactions (often non-specific) that can impair the desired pharmacological activity of the soluble CD1d or $\beta_2$-microglobulin polypeptide moiety. Preferably, at least 50% of the biological activity (as demonstrated, e.g., in any of the assays described herein or known in the art) of the soluble CD1d or $\beta_2$-microglobulin polypeptide is retained, and most preferably nearly 100% is retained.

The polymer can be conjugated to the soluble CD1d or $\beta_2$-microglobulin polypeptide using conventional chemistry. For example, a polyalkylene glycol moiety can be coupled to a lysine epsilon amino group of the soluble CD1d or $\beta_2$-microglobulin polypeptide. Linkage to the lysine side chain can be performed with an N-hydroxylsuccinimide (NHS) active ester such as PEG succinimidyl succinate (SS-PEG) and succinimidyl propionate (SPA-PEG). Suitable polyalkylene glycol moieties include, e.g., carboxymethyl-NHS and norleucine-NHS, SC. These reagents are commercially available. Additional amine-reactive PEG linkers can be substituted for the succinimidyl moiety. These include, e.g., isothiocyanates, nitrophenylcarbonates (PNP), epoxides, benzotriazole carbonates, SC-PEG, tresylate, aldehyde, epoxide, carbonylimidazole and PNP carbonate. Conditions are usually optimized to maximize the selectivity and extent of reaction. Such optimization of reaction conditions is within ordinary skill in the art.

PEGylation can be carried out by any of the PEGylation reactions known in the art. See, e.g., *Focus on Growth Factors*, 3:4-10, 1992 and European patent applications EP 0 154 316 and EP 0 401 384. PEGylation may be carried out using an acylation reaction or an alkylation reaction with a reactive polyethylene glycol molecule (or an analogous reactive water-soluble polymer).

PEGylation by acylation generally involves reacting an active ester derivative of polyethylene glycol. Any reactive PEG molecule can be employed in the PEGylation. PEG esterified to N-hydroxysuccinimide (NHS) is a frequently used activated PEG ester. As used herein, "acylation" includes without limitation the following types of linkages between the therapeutic protein and a water-soluble polymer such as PEG: amide, carbamate, urethane, and the like. See, e.g., *Bioconjugate Chem.* 5:133-140, 1994. Reaction parameters are generally selected to avoid temperature, solvent, and pH conditions that would damage or inactivate the soluble CD1d or $\beta_2$-microglobulin polypeptide.

Generally, the connecting linkage is an amide and typically at least 95% of the resulting product is mono-, di- or tri-PEGylated. However, some species with higher degrees of PEGylation may be formed in amounts depending on the specific reaction conditions used. Optionally, purified PEGylated species are separated from the mixture, particularly unreacted species, by conventional purification methods, including, e.g., dialysis, salting-out, ultrafiltration, ion-exchange chromatography, gel filtration chromatography, hydrophobic exchange chromatography, and electrophoresis.

PEGylation by alkylation generally involves reacting a terminal aldehyde derivative of PEG with a soluble CD1d or $\beta_2$-microglobulin polypeptide or polypeptide fragment of the invention in the presence of a reducing agent. In addition, one can manipulate the reaction conditions to favor PEGylation substantially only at the N-terminal amino group of the soluble CD1d or $\beta_2$-microglobulin polypeptide, i.e. a mono-PEGylated protein. In either case of mono-PEGylation or poly-PEGylation, the PEG groups are typically attached to the protein via a —CH2-NH— group. With particular reference to the —CH2- group, this type of linkage is known as an "alkyl" linkage.

Derivatization via reductive alkylation to produce an N-terminally targeted mono-PEGylated product exploits differential reactivity of different types of primary amino groups (lysine versus the N-terminal) available for derivatization. The reaction is performed at a pH that allows one to take advantage of the pKa differences between the epsilon-amino groups of the lysine residues and that of the N-terminal amino group of the protein. By such selective derivatization, attachment of a water-soluble polymer that contains a reactive group, such as an aldehyde, to a protein is controlled: the conjugation with the polymer takes place predominantly at the N-terminus of the protein and no significant modification of other reactive groups, such as the lysine side chain amino groups, occurs.

The polymer molecules used in both the acylation and alkylation approaches are selected from among water-soluble polymers. The polymer selected is typically modified to have a single reactive group, such as an active ester for acylation or an aldehyde for alkylation, so that the degree of polymerization may be controlled as provided for in the present methods. An exemplary reactive PEG aldehyde is polyethylene glycol propionaldehyde, which is water stable, or mono C1-C10 alkoxy or aryloxy derivatives thereof (see, e.g., Harris et al., U.S. Pat. No. 5,252,714). The polymer may be branched or unbranched. For the acylation reactions, the polymer(s) selected typically have a single reactive ester group. For reductive alkylation, the polymer(s) selected typically have a single reactive aldehyde group. Generally, the water-soluble polymer will not be selected from naturally occurring glycosyl residues, because these are usually made more conveniently by mammalian recombinant expression systems.

Methods for preparing a PEGylated soluble CD1d or $\beta_2$-microglobulin polypeptide of the invention generally include the steps of (a) reacting a soluble CD1d or B$_2$-microglobulin polypeptide or polypeptide fragment of the invention with polyethylene glycol (such as a reactive ester or aldehyde derivative of PEG) under conditions whereby the molecule becomes attached to one or more PEG groups, and (b) obtaining the reaction product(s). In general, the optimal reaction conditions for the acylation reactions will be determined case-by-case based on known parameters and the desired result. For example, a larger the ratio of PEG to protein, generally leads to a greater the percentage of poly-PEGylated product.

Reductive alkylation to produce a substantially homogeneous population of mono-polymer/soluble CD1d or $\beta_2$-microglobulin polypeptide generally includes the steps of: (a) reacting a soluble CD1d or $\beta_2$-microglobulin polypeptide or polypeptide fragment of the invention with a reactive PEG molecule under reductive alkylation conditions, at a pH suitable to permit selective modification of the N-terminal amino group of soluble CD1d or $\beta_2$-microglobulin; and (b) obtaining the reaction product(s).

For a substantially homogeneous population of mono-polymer/soluble CD1d or $\beta_2$-microglobulin polypeptide, the reductive alkylation reaction conditions are those that permit the selective attachment of the water-soluble polymer moiety to the N-terminus of a soluble CD1d or $\beta_2$-microglobulin polypeptide or polypeptide fragment of the invention. Such reaction conditions generally provide for pKa differences between the lysine side chain amino groups and the N-terminal amino group. For purposes of the present invention, the pH is generally in the range of 3-9, typically 3-6.

In some embodiments, the polyalkylene glycol moiety is coupled to a cysteine group of the soluble CD1d or $\beta_2$-microglobulin polypeptide. Coupling can be effected using, e.g., a maleimide group, a vinylsulfone group, a haloacetate group, or a thiol group.

Optionally, the soluble CD1d or $\beta_2$-microglobulin polypeptide is conjugated to the polyethylene-glycol moiety through a labile bond. The labile bond can be cleaved in, e.g., biochemical hydrolysis, proteolysis, or sulfhydryl cleavage. For example, the bond can be cleaved under in vivo (physiological) conditions.

The reactions may take place by any suitable method used for reacting biologically active materials with inert polymers, generally at about pH 5-8, e.g., pH 5, 6, 7, or 8, if the reactive groups are on the alpha amino group at the N-terminus. Generally the process involves preparing an activated polymer and thereafter reacting the protein with the activated polymer to produce the soluble protein suitable for formulation.

Vectors

Vectors comprising nucleic acids encoding soluble CD1d or $\beta_2$-microglobulin polypeptides may be used to produce CD1d complexes, e.g., non-specific CD1d complexes for use in the methods of the invention. The choice of vector and expression control sequences to which such nucleic acids are operably linked depends on the functional properties desired, e.g., protein expression, and the host cell to be transformed.

Expression control elements useful for regulating the expression of an operably linked coding sequence are known in the art. Examples include, but are not limited to, inducible promoters, constitutive promoters, secretion signals, and other regulatory elements. When an inducible promoter is used, it can be controlled, e.g., by a change in nutrient status, or a change in temperature, in the host cell medium.

The vector can include a prokaryotic replicon, i.e., a DNA sequence having the ability to direct autonomous replication and maintenance of the recombinant DNA molecule extrachromosomally in a bacterial host cell. Such replicons are well known in the art. In addition, vectors that include a prokaryotic replicon may also include a gene whose expression confers a detectable marker such as a drug resistance. Examples of bacterial drug-resistance genes are those that confer resistance to ampicillin or tetracycline.

Vectors that include a prokaryotic replicon can also include a prokaryotic or bacteriophage promoter for directing expression of the coding gene sequences in a bacterial host cell. Promoter sequences compatible with bacterial hosts are typically provided in plasmid vectors containing convenient restriction sites for insertion of a DNA segment to be expressed. Examples of such plasmid vectors are pUC8, pUC9, pBR322 and pBR329 (BioRad® Laboratories), pPL and pKK223 (Pharmacia). Any suitable prokaryotic host can be used to express a recombinant DNA molecule encoding a protein used in the methods of the invention.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. The neomycin phosphotransferase (neo) gene is an example of a selectable marker gene (Southern et al., *J. Mol. Anal. Genet.* 1:327-341 (1982)). Additional elements may also be needed for optimal synthesis of mRNA. These elements may include signal sequences, splice signals, as well as transcriptional promoters, enhancers, and termination signals.

Of course, any expression vector which is capable of eliciting expression in eukaryotic cells may be used in the present invention. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6/V5-His, pVAX1, and pZeoSV2 (available from Invitrogen, San Diego, Calif.), and plasmid pCI (available from Promega, Madison, Wisc.). Additional eukaryotic cell expression vectors are known in the art and are commercially available. Typically, such vectors contain convenient restriction sites for insertion of the desired DNA segment. Exemplary vectors include pSVL and pKSV-10 (Pharmacia), pBPV-1, pml2d (International Biotechnologies), pTDT1 (ATCC 31255), retroviral expression vector pMIG and pLL3.7, adenovirus shuttle vector pDC315, and AAV vectors. Other exemplary vector systems are disclosed e.g., in U.S. Pat. No. 6,413,777.

In general, screening large numbers of transformed cells for those which express suitably high levels of a soluble CD1d or $\beta_2$-microglobulin polypeptide is routine experimentation which can be carried out, for example, by robotic systems.

Frequently used regulatory sequences for mammalian host cell expression include viral elements that direct high levels of protein expression in mammalian cells, such as promoters and enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdmlP)), polyoma and strong mammalian promoters such as native immunoglobulin and actin promoters. For further description of viral regulatory elements, and sequences thereof, see e.g., Stinski, U.S. Pat. No. 5,168,062; Bell, U.S. Pat. No. 4,510,245; and Schaffner, U.S. Pat. No. 4,968,615.

The recombinant expression vectors may carry sequences that regulate replication of the vector in host cells (e.g., origins of replication) and selectable marker genes. The selectable marker gene facilitates selection of host cells into which the vector has been introduced (see, e.g., Axel, U.S. Pat. Nos. 4,399,216; 4,634,665 and 5,179,017). For example, typically the selectable marker gene confers resistance to a drug, such as G418, hygromycin or methotrexate, on a host cell into which the vector has been introduced. Frequently used selectable marker genes include the dihydrofolate reductase (DHFR) gene (for use in dhfr-host cells with methotrexate selection/amplification) and the neo gene (for G418 selection).

Vectors encoding soluble CD1d or $\beta_2$-microglobulin polypeptides can be used for transformation of a suitable host cell. Transformation can be by any suitable method. Methods for introduction of exogenous DNA into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

Transformation of host cells can be accomplished by conventional methods suited to the vector and host cell employed. For transformation of prokaryotic host cells, electroporation and salt treatment methods can be employed (Cohen et al., Proc. Natl. Acad. Sci. USA 69:2110-14 (1972)). For transformation of vertebrate cells, electroporation, cationic lipid or salt treatment methods can be employed. See, e.g., Graham et al., Virology 52:456-467 (1973); Wigler et al., Proc. Natl. Acad. Sci. USA 76:1373-76 (1979).

The host cell line used for protein expression may be of mammalian origin; those skilled in the art are credited with ability to determine particular host cell lines which are best suited for the desired gene product to be expressed therein. Exemplary host cell lines include, but are not limited to, NSO, SP2 cells, baby hamster kidney (BHK) cells, monkey kidney cells (COS), human hepatocellular carcinoma cells (e.g., Hep G2), A549 cells DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

Expression of polypeptides from production cell lines can be enhanced using known techniques. For example, the glutamine synthetase (GS) system is commonly used for enhancing expression under certain conditions. See, e.g., European Patent Nos. 0 216 846, 0 256 055, and 0 323 997 and European Patent Application No. 89303964.4.

Ceramide-Like Glycolipid Antigens

Ceramide like glycolipid antigens useful within the present invention include any which are capable of modulating an immune response in an animal when presented in conjunction with a CD1d molecule. The antigens may be derived from foreign antigens or from autoantigens. Further, the antigens may be synthetic. Suitable antigens are disclosed, e.g., in Porcelli, U.S. Patent Appl. Publ. No. 2006/0052316, Tsuji, U.S. Patent Appl. Publ. No. 2006/0211856, Jiang, U.S. Patent Appl. Publ. No. 2006/0116331, Hirokazu et al., U.S. Patent Appl. Publ. No. 2006/0074235, Tsuji et al., U.S. Patent Appl. Publ. No. 2005/0192248, Tsuji, U.S. Patent Application No. 2004/0127429, and Tsuji et al., U.S. Patent Application No. 2003/0157135, which are incorporated herein by reference. In certain embodiments, the ceramide-like glycolipid antigen is α-GalCer.

Other Ceramide-like glycolipid antigens for use in the present invention include, but are not limited to, the antigens in Table 3.

TABLE 3

| Compound Name Bronx | UK/ other | CHO group | N-linked group | sphingoid base | MW | Structure | Activity in vitro | Activity in vivo | Comments |
|---|---|---|---|---|---|---|---|---|---|
| DB04-1 | KRN 7000 | α-D-Gal | C26:0 | C18 aminotriol | 858.32 | | +++ | +++ | KRN7000. Strong agonist, mixed IL-4 and IFNγ response both in vivo and in vitro. |
| DB01-1 | | α-D-Gal | C24:0 | C18 aminotriol | 830.27 | | ++ | ++ | Similar to KRN7000, but slightly less potent. Strong agonist, mixed IL-4 and IFNγ response both in vivo and in vitro. |
| DB02-1 | | α-D-Glu | C24:0 | C18 aminotriol | 830.27 | | + | + | Moderate to weak iNKT agonist in vitro and in vivo. Gives reasonably strong early IL-4 response, with reduced late IFNγ like DB03-4 or OCH. |
| DB03-4 | | α-D-Gal | C20; 11, 14 cis dienoic | C18 aminotriol | 770.13 | | +++ | +++ | "Type 2 Cytokine bias": Strong inducer of iNKT cell IL-4 response, with blunted IFNγ and NK cell transactivation. |

TABLE 3-continued

| Compound Name | | CHO group | N-linked group | sphingoid base | MW | Structure | Activity in vitro | Activity in vivo | Comments |
|---|---|---|---|---|---|---|---|---|---|
| Bronx | UK/other | | | | | | | | |
| DB03-5 | | α-D-Gal | C20; 5, 8, 11, 14 cis tetra-enoic (arachi-donate) | C18 aminotriol | 766.10 | | ++ | ++ | "Type 2 Cytokine bias". Strong inducer of iNKT cell IL-4 response, with blunted IFNγ and NK cell transactivation. |
| DB03-8 | PI-11 | α-L-Fuc | C24:0 | C18 aminotriol | 814.27 | | + | +/− | Weak iNKT agonist activity in vitro. No serum cytokine response in vivo, but exacerbates SLE in NZB/W F1 mice. Possible antagonist/partial agonist. |
| DB04-9 | PI-14 | β-D-Man | C20, 11, 14 cis dienoic | C18 aminotriol | 770.13 | | ++ | ++ | Similar to DB03-4. Most active among the β-Man analogues tested to date (7/30/05) |
| DB05-9 | PI-19 | α-D-Gal | C18:2 (10t, 12c, conj) | C18 aminotriol | 742.08 | | ++ | ND | A potent Th2-biased agonist in vitro. Not tested yet in vivo (122206) |

TABLE 3-continued

| Compound Name | | CHO group | N-linked group | sphingoid base | MW | Structure | Activity in vitro | Activity in vivo | Comments |
|---|---|---|---|---|---|---|---|---|---|
| Bronx | UK/other | | | | | | | | |
| DB05-10 | PI-20 | α-D-Gal | C18:3 (9c, 11t, 13c, conj) | C18 aminotriol | 740.06 | 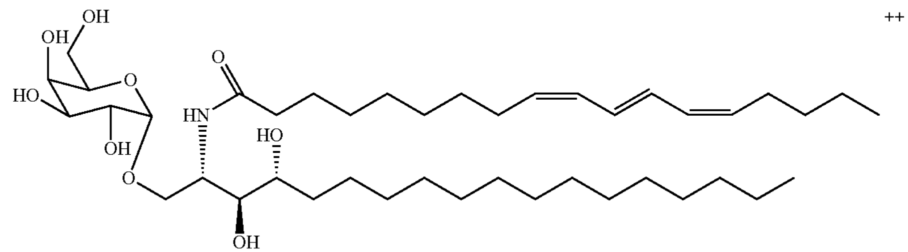 | ++ | ND | Similar to DB05-9, possibly slightly more potent |
| DB05-11 | PI-21 | α-D-Gal | C18:2 (9c, 11c, conj) | C18 aminotriol | 742.08 | 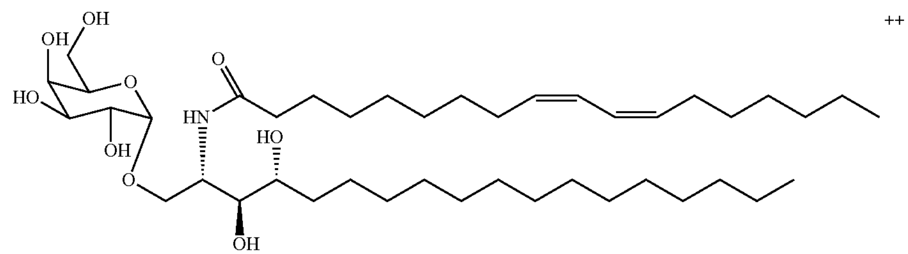 | ++ | ND | A potent Th2-biased analogue similar to DB05-9, possibly more active in proliferation assay |
| DB05-12 | PI-22 | α-D-Gal | C20:2 (11c, 13t, conj) | C18 aminotriol | 770.13 | 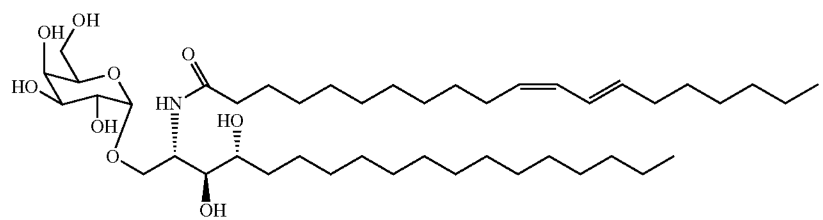 [SMILES: CCCCCC/C=C/C=C\CCCCCCCCCC(=O)N[C@@H](COC1OC(CO)C(O)C(O)C1O)[C@H](O)[C@H](O)CCCCCCCCCCCCCC] | ++ | ND | Similar to DB05-11, but possibly less potent and less Th2-bias |

TABLE 3-continued

| Compound Name | | | | | | Activity | Activity | |
| Bronx | UK/other | CHO group | N-linked group | sphingoid base | MW | Structure | in vitro | in vivo | Comments |
| --- | --- | --- | --- | --- | --- | --- | --- | --- | --- |
| DB05-14 | PI-24 | α-D-Gal | C18:3 (8t, 10t, 12c, conj) | C18 aminotriol | 740.06 | | +++ | ND | Very active in prolif, strong IL-4 secretion bias |
| DB05-15 | PI-26 | α-D-Gal | C18:2 (9c, 11t, conj) | C18 aminotriol | 742.08 | | ++ | ND | Similar to DB05-14 |
| DB05-16 | PI-27 | α-D-Gal | C18:2 (9t, 11t, conj) | C18 aminotriol | 742.08 | | ++ | ND | Similar to DB05-14 |

TABLE 3-continued

| Compound Name | | | | | | | Activity in vitro | Activity in vivo | Comments |
|---|---|---|---|---|---|---|---|---|---|
| Bronx | UK/other | CHO group | N-linked group | sphingoid base | MW | Structure | | | |
| DB05-17 | PL-29 | α-D-Gal | C18:3 (9c, 11t, 13t, conj) | C18 aminotriol | 740.06 | | ++ | ND | Weak in splenocyte prolif, but moderately strong in cytokine secretion assays with moderate IL-4 predominance |
| DB06-14 | | α-L-Fuc | C26:0 | C18 aminotriol | 842.32 | | + | ND | Weakly active in splenocyte stimulation in vitro. Minimal or no prolif, but moderate IL-4 secretion at high concentration with weak IFNg (needs to be compared directly to DB03-8) |
| DB06-15 | | α-D-Glu | C20:2 (cis 11, 14) | C18 aminotriol | 770.13 | | + | ND | Moderately active in splenocyte prolif; Weak IL-4 and even weaker INFg secretion |
| AH04-1 | RMN 3-84 | α-D-Gal | C24:0 | C9 aminotriol | 704.03 | | ++ | ++ | Identical to OCH |

TABLE 3-continued

| Compound Name | | CHO group | N-linked group | sphingoid base | MW | Structure | Activity in vitro | Activity in vivo | Comments |
|---|---|---|---|---|---|---|---|---|---|
| Bronx | UK/other | | | | | | | | |
| AH04-2 | | α-D-Gal | C24:0 | C9 aminotriol | 688.03 | | ++ | ND | Similar activity to OCH in B6 splenocyte assay. About a half log more potent than OCH in hybridoma stimulation assay. No info on recognition by human iNKT cells. |
| YTC03-15 | | α-D-Gal | C18:0 | C18 aminotriol | 746.11 | | + | ND | EXTREMELY active when presented to mouse iNKT hybridoma by human CD1d + HeLa cells |
| YTC03-17 | | α-D-Gal | Bi-phenylacetate | C18 aminotriol | 705.96 | | ++ | − | Very strong agonist in some in vitro studies, but no activity detectable in vivo (cytokine stimulation). |

TABLE 3-continued

| Compound Name | | CHO group | N-linked group | sphingoid base | MW | Structure | Activity in vitro | Activity in vivo | Comments |
|---|---|---|---|---|---|---|---|---|---|
| Bronx | UK/other | | | | | | | | |
| YTC03-24 | | α-D-Gal | di-methoxy-phenyl acetate | C18 aminotriol | 657.83 | 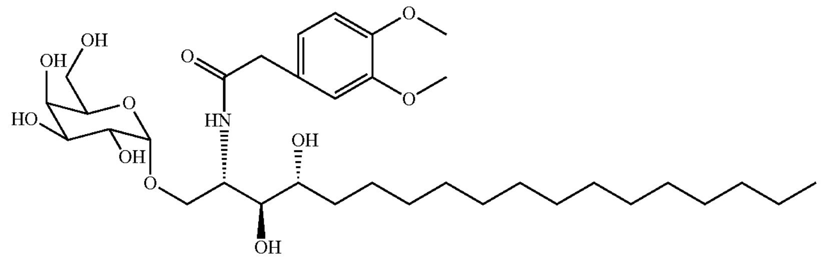 [SMILES: CCCCCCCCCCCCCC[C@@H](O)[C@@H](O)[C@H](COC1OC(CO)C(O)C(O)C1O)NC(=O)Cc1ccc(OC)c(OC)c1] | + | − | Possible enhanced IL-4 relative to IFNγ in vitro with splenocytes from NZB/W F1 mice |
| YTC03-30 | | α-D-Gal | fluoro-phenyl acetate | C18 aminotriol | 615.77 | 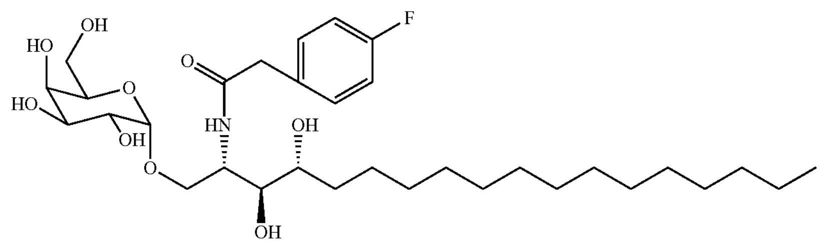 [SMILES: CCCCCCCCCCCCCC[C@@H](O)[C@@H](O)[C@H](COC1OC(CO)C(O)C(O)C1O)NC(=O)Cc1ccc(F)cc1] | + | − | Possible enhanced IL-4 relative to IFNγ in vitro with splenocytes from NZB/W F1 mice. EXTREMELY active when presented to mouse iNKT hybridoma by human CD1d + HeLa cells |
| YTC03-33 | | α-D-Gal | methoxy-phenyl acetate | C18 aminotriol | 627.81 | 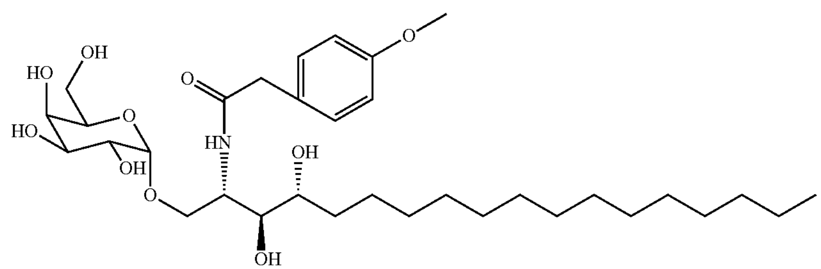 [SMILES: CCCCCCCCCCCCCC[C@@H](O)[C@@H](O)[C@H](COC1OC(CO)C(O)C(O)C1O)NC(=O)Cc1ccc(OC)cc1] | + | ND | |

TABLE 3-continued

| Compound Name | | CHO group | N-linked group | sphingoid base | MW | Structure | Activity in vitro | Activity in vivo | Comments |
|---|---|---|---|---|---|---|---|---|---|
| Bronx | UK/other | | | | | | | | |
| YTC03-34 | | α-D-Gal | C10:0 | C18 aminotriol | 633.90 | | + | + | Moderate activity with mouse iNKT hybridoma. Possible TH2 skewing of cytokine response? Active in vivo with good IL-4 production assoc. with weak IFNgamma and weak IL-12 p70 (very interesting compound!) |
| SKRN 7000 | | α-D-Gal | C26:0 | C18 aminotriol | 874.39 | | − | ND | S-glycoside of KRN7000 from D. Bundle. No agonist activity in iNKT hybridoma assay. However, seemed to reduce autoreactivity of iNKT cell hybridoma, so might be worth evaluating as an antagonist. |
| RF03-1 | | α-D-Gal | C26:0 | C19 aminotriol | 856.35 | | +/− | ND | C-glycoside of KRN7000. Reported to be strong agonist, with enhanced IFNγ production in vivo. May have slower kinetics of activation. |
| OCH | (AH04-1) | α-D-Gal | C24:0 | C9 aminotriol | 704.03 | | ++ | ++ | Famous "TH2-skewing" analogue. Weaker agonist than DB03-4 in our hands, and skewing of cytokine response not very impressive in most assays. Also, seems NOT to be recognized by human iNKT cells. |

Ceramide-like glycolipid antigens are bound or associated with soluble CD1d polypeptides by standard methods known to those of ordinary skill in the art. For example, a preparation of purified CD1d protein (including both the CD1d and $\beta_2$-microglobulin subunits is mixed with a 2.5 molar excess of α-GalCer, insuring that every CD1d protein is bound with antigen. Excess α-GalCer is then removed, e.g., by chromatographic methods, e.g., size exclusion FPLC.

In certain embodiments, compositions for use in the methods of the present invention further comprise another component, e.g., a polypeptide with immunological activity. Preferably, the protein with immunological activity is a costimulatory molecule, such as a Saponin, a toll-like receptor ("TLR"), B7.1 or B7.2. "B7" is used herein to generically refer to either B7.1 or B7.2. In one embodiment, a costimulatory molecule, e.g., the extracellular domain of B7-1 (CD80) or B7-2 (CD86) that interacts with CD28 on T- and NK-cells, is administered as an amino terminal fusion to β2-microglobulin incorporated into the structure of a soluble CD1d complex for use in the present invention. See, e.g., WO 9964597, published 16 Dec. 1999. Alternatively, a costimulatory molecule is administered as an amino-terminal fusion to the CD1d heavy chain. In certain embodiments, incorporation of a costimulatory molecule, e.g., a B7 signaling molecule in the compositions of the invention allows more effective and prolonged activation of CD1d-restricted NKT cells by the soluble CD1d complex.

In other embodiments, the compositions for use in the methods of the present invention further comprise adjuvant components, e.g., Toll-like receptor (TLR) agonists. Examples of TLR agonist adjuvants which may be effective, include, but are not limited to: N-acetylmuramyl-L-alanine-D-isoglutamine (MDP), lipopolysaccharides (LPS), genetically modified and/or degraded LPS, alum, glucan, colony stimulating factors (e.g., EPO, GM-CSF, G-CSF, M-CSF, PEGylated G-CSF, SCF, IL-3, IL6, PIXY 321), interferons (e.g., γ-interferon, α-interferon), interleukins (e.g., IL-2, IL-7, IL-12, IL-15, IL-18), saponins (e.g., QS21), monophosphoryl lipid A (MPL), 3 De-O-acylated monophosphoryl lipid A (3D-MPL), unmethylated CpG sequences, 1-methyl tryptophan, arginase inhibitors, cyclophosphamide, antibodies that block immunosuppressive functions (e.g., anti-CTLA4 antibodies), lipids (such as palmitic acid residues), tripalmitoyl-S-glycerylcystein lyseryl-serine ($P_3$ CSS), and Freund's adjuvant.

Alternatively or additionally, compositions of the present invention my further comprise a lymphokine or cytokine that modulates immune cell activation such as interleukins IL-1, IL-2, IL-3, IL-4, IL-5, IL-6, IL-10, IL-12, IL-15, IL-18; granulocyte-macrophage colony stimulating factor (GM-CSF); transforming growth factor (TGF, e.g., TGFα and TGFβ); α interferons (e.g. IFNα); β interferons (e.g. IFNβ); γ interferons (e.g. IFNγ) or lymphocyte function-associated protein, such as LFA-1 or LFA-3; or an intercellular adhesion molecule, such as ICAM-1 or ICAM-2.

Compositions of the present invention may contain a homogenous or heterogeneous population of antigens and/or costimulatory molecules. That is, each soluble CD1d polypeptide in the composition may be linked to the same ceramide-like glycolipid antigen or soluble CD1d polypeptides may be linked to different antigens. Likewise, various soluble CD1d complexes may be associated with the same costimulatory molecules or different costimulatory molecules.

The soluble CD1d complexes of the present invention, or compositions comprising same may be labeled, so as to be directly detectable, or will be used in conjunction with secondary labeled immunoreagents which will specifically bind the compound for example, for detection or diagnostic purposes. Labels of interest may include dyes, enzymes, chemiluminescers, particles, radioisotopes, or other directly or indirectly detectable agent. Alternatively, a second stage label may be used, e.g. labeled antibody directed to one of the constituents of the compound of the invention.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, 58Co, 59Fe, 75Se, 152Eu, 90Y, 67Cu, 217Ci, 211At, 212Pb, 47Sc, 109Pd, etc. Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and Fe.

Typical techniques for binding the above-described labels to polypeptides are provided by Kennedy et al., Clin. Chim. Acta 70:1-31 (1976), and Schurs et al., Clin. Chim. Acta 81:1-40 (1977). Coupling techniques mentioned in the latter are the glutaraldehyde method, the periodate method, the dimaleimide method, the m-maleimidobenzyl-N-hydroxysuccinimide ester method, all of which methods are incorporated by reference herein.

Immunogenic and Therapeutic Molecules

An "immunogenic polypeptide" is meant to encompass any antigenic or immunogenic polypeptides including polyamino acid materials having epitopes or combinations of epitopes. As used herein, an immunogenic polypeptide is a polypeptide which, when introduced into a vertebrate, reacts with the immune system molecules of the vertebrate, i.e., is antigenic, and/or induces an immune response in the vertebrate, i.e., is immunogenic. It is quite likely that an immunogenic polypeptide will also be antigenic, but an antigenic polypeptide, because of its size or conformation, may not necessarily be immunogenic. Examples of antigenic and immunogenic polypeptides include, but are not limited to, polypeptides from infectious agents such as bacteria, viruses, parasites, or fungi, allergens such as those from pet dander, plants, dust, and other environmental sources, as well as certain self polypeptides, for example, tumor-associated antigens.

Antigenic and immunogenic polypeptides of the present invention can be used to prevent or treat, i.e., cure, ameliorate, lessen the severity of, or prevent or reduce contagion of viral, bacterial, fungal, and parasitic infectious diseases, as well as to treat allergies.

In addition, antigenic and immunogenic polypeptides of the present invention can be used to prevent or treat, i.e., cure, ameliorate, or lessen the severity of cancer including, but not limited to, cancers of oral cavity and pharynx (i.e., tongue, mouth, pharynx), digestive system (i.e., esophagus, stomach, small intestine, colon, rectum, anus, anal canal, anorectum, liver, gallbladder, pancreas), respiratory system (i.e., larynx, lung), bones, joints, soft tissues (including heart), skin, melanoma, breast, reproductive organs (i.e., cervix, endometirum, ovary, vulva, vagina, prostate, testis, penis), urinary system (i.e., urinary bladder, kidney, ureter, and other urinary organs), eye, brain, endocrine system (i.e., thyroid and other endocrine), lymphoma (i.e., hodgkin's disease, non-hodgkin's lymphoma), multiple myeloma, leukemia (i.e., acute lymphocytic leukemia, chronic lymphocytic leukemia, acute myeloid leukemia, chronic myeloid leukemia).

Examples of viral antigenic and immunogenic polypeptides include, but are not limited to, adenovirus polypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (AE) polypeptides, e.g., a hepatitis B core or surface antigen, herpesvirus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picoma virus polypeptides, e.g., a poliovirus capsid polypeptide, pox virus polypeptides, e.g., a vaccinia virus polypeptide, rabies virus polypeptides, e.g., a rabies virus glycoprotein G, reovirus polypeptides, retrovirus polypeptides, and rotavirus polypeptides.

Examples of bacterial antigenic and immunogenic polypeptides include, but are not limited to, *Actinomyces* polypeptides, *Bacillus* polypeptides, e.g., immunogenic polypeptides from *Bacillus anthracis*, *Bacteroides* polypeptides, *Bordetella* polypeptides, *Bartonella* polypeptides, *Borrelia* polypeptides, e.g., *B. burgdorferi* OspA, *Brucella* polypeptides, *Campylobacter* polypeptides, *Capnocytophaga* polypeptides, *Chlamydia* polypeptides, *Clostridium* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides, e.g., *H. influenzae* type b outer membrane protein, *Helicobacter* polypeptides, *Klebsiella* polypeptides, L form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., *S. pyogenes* M proteins, *Treponema* polypeptides, and *Yersinia* polypeptides, e.g., *Y. pestis* F1 and V antigens.

Examples of tumor-associated antigenic and immunogenic polypeptides include, but are not limited to, tumor-specific immunoglobulin variable regions, GM2, Tn, sTn, Thompson-Friedenreich antigen (TF), Globo H, Le(y), MUC1, MUC2, MUC3, MUC4, MUC5AC, MUC5B, MUC7, carcinoembryonic antigens, beta chain of human chorionic gonadotropin (hCG beta), C35, HER2/neu, CD20, PSMA, EGFRvIII, KSA, PSA, PSCA, GP100, MAGE 1, MAGE 2, TRP 1, TRP 2, tyrosinase, MART-1, PAP, CEA, BAGE, MAGE, RAGE, and related proteins.

Compositions of the present invention may further comprise other therapeutic agents. The therapeutic agent or agents may be linked to or otherwise associated with the soluble the CD1d complex. Examples of therapeutic agents include, but are not limited to, antimetabolites, alkylating agents, anthracyclines, antibiotics, and anti-mitotic agents. Antimetabolites include methotrexate, 6-mercaptopurine, 6-thioguanine, cytarabine, 5-fluorouracil decarbazine. Alkylating agents include mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin. Anthracyclines include daunorubicin (formerly daunomycin) and doxorubicin (also referred to herein as adriamycin). Additional examples include mitozantrone and bisantrene. Antibiotics include dactinomycin (formerly actinomycin), bleomycin, mithramycin, and anthramycin (AMC). Antimytotic agents include vincristine and vinblastine (which are commonly referred to as vinca alkaloids). Other cytotoxic agents include procarbazine, hydroxyurea, asparaginase, corticosteroids, mytotane (O,P'-(DDD)), interferons. Further examples of cytotoxic agents include, but are not limited to, ricin, doxorubicin, taxol, cytochalasin B, gramicidin D, ethidium bromide, etoposide, tenoposide, colchicin, dihydroxy anthracin dione, 1-dehydrotestosterone, and glucocorticoid.

Analogs and homologs of such therapeutic and cytotoxic agents are encompassed by the present invention. For example, the chemotherapuetic agent aminopterin has a correlative improved analog namely methotrexate. Further, the improved analog of doxorubicin is an Fe-chelate. Also, the improved analog for 1-methylnitrosourea is lomustine. Further, the improved analog of vinblastine is vincristine. Also, the improved analog of mechlorethamine is cyclophosphamide.

NKT Activity Assays

The ability of a composition of the present invention to modulate an immune response can be readily determined by an in vitro assay. NKT cells for use in the assays include transformed NKT cell lines, or NKT cells which are isolated from a mammal, e.g., from a human or from a rodent such as a mouse. NKT cells can be isolated from a mammal by sorting cells that bind CD1d:α-GalCer tetramers. See, for example, Benlagha et al., J Exp Med 191 (2000), pp. 1895-1903; Matsuda et al., J Exp Med 192 (2000), pp. 741-754; and Karadimitris et al., Proc Natl Acad Sci USA 98 (2001), pp. 3294-3298. A suitable assay to determine if a compound of the present invention is capable of modulating the activity of NKT cells is conducted by coculturing NKT cells and antigen presenting cells, adding the particular compound of interest to the culture medium that targets either the antigen presenting cells or the NKT cells directly, and measuring IL-4 or IFN-γ production. A significant increase or decrease in IL-4 or IFN-γ production over the same co-culture of cells in the absence of the compound of the invention or, preferably, in the presence of a compound of the invention with a non-targeting antibody indicates stimulation or inhibition of NKT cells.

The NKT cells employed in the assays are incubated under conditions suitable for proliferation. For example, an NKT cell hybridoma is suitably incubated at about 37° C. and 5% CO2 in complete culture medium (RPMI 1640 supplemented with 10% FBS, penicillin/streptomycin, L-glutamine and 5×10–5 M 2-mercaptoethanol). Serial dilutions of the compound can be added to the NKT cell culture medium. Suitable concentrations of the compound added to the NKT cells typically will be in the range of from $10^{-12}$ to $10^{-6}$ M. Use of antigen dose and APC numbers giving slightly submaximal NKT cell activation is preferred to detect stimulation or inhibition of NKT cell responses by the compounds of the invention.

Alternatively, rather than measurement of an expressed protein such as IL-4 or IFN-γ, modulation of NKT cell activation can be determined by changes in antigen-dependent T cell proliferation as measured by radiolabelling techniques as are recognized in the art. For example, a labeled (e.g., tritiated) nucleotide may be introduced to an assay culture medium. Incorporation of such a tagged nucleotide into DNA serves as a measure of T cell proliferation. This assay is not suitable for NKT cells that do not require antigen presentation for growth, e.g., NKT cell hybridomas. A difference in the level of T cell proliferation following contact with the compound of the invention indicates the complex modulates activity of the T cells. For example, a decrease in NKT cell proliferation indicates the compound can suppress an immune response. An increase in NKT cell proliferation indicates the compound can stimulate an immune response.

Additionally, the $^{51}$Cr release assay, described below, can be used to determine cytotoxic activity.

These in vitro assays can be employed to select and identify soluble CD1d complexes and compositions comprising same that are capable of modulating an immune response. Assays described above, e.g., measurement of IL-4 or IFN-γ production or NKT cell proliferation, are employed to determine if contact with the compound modulates T cell activation.

In vivo assays also may be suitably employed to determine the ability of a composition of the invention to modulate the activity of NKT cells. For example, a composition of interest can be assayed for its ability to stimulate NKT cell activation or inhibit tumor growth. For example, a composition of the invention can be administered to a mammal such as a mouse, before or after challenge with a tumorigenic dose of transformed cells and the presence or size of growing tumors may be monitored.

Compositions of the present invention further comprise a suitable carrier. Such compositions comprise a therapeutically effective amount of the soluble CD1d complex and a pharmaceutically acceptable carrier or excipient. Such a carrier includes but is not limited to saline, buffered saline, dextrose, water, glycerol, ethanol, and combinations thereof. The formulation should suit the mode of administration.

Methods of Treatment

The present invention also includes a method of modulating, i.e., either stimulating or inhibiting an immune response, comprising administering to an animal an effective amount of a composition comprising a soluble CD1d complex loaded with a ceramide-like glycolipid antigen as described herein.

The present invention further provides a method of treating a disease in an animal, comprising administering to an animal with that disease, or prone to contract that disease, a composition comprising a soluble CD1d complex loaded with a ceramide-like glycolipid antigen as described herein.

According to these methods, a composition if the present invention is administered in an amount sufficient to alter the progression of said disease.

Certain embodiments of the present invention include a method of reducing or eliminating the anergic response of NKT cells to multiple administrations of ceramide-like glycolipid antigens administered by themselves, which are therefore presented to NKT cells in the context of cell-bound CD1d. It has been shown that multiple administrations of α-GalCer, administered by itself, causes NKT cells to become non-responsive for an extended period of time. The present invention, in which glycolipids such as α-GalCer are administered as part of a soluble CD1d complex, protects NKT cells from anergy in response to antigen, and allows for a prolonged response upon multiple administrations. Accordingly, NKT cells are activated in response to stimulation with soluble CD1d complexes loaded with a ceramide-like glycolipid antigen of the present invention and furthermore, NKT cells can be reactivated in response to restimulation by soluble CD1d complexes loaded with a ceramide-like glycolipid antigen of the present invention.

In certain embodiments, soluble CD1d complexes for use in the methods described herein are "non-specific" soluble CD1d complexes, i.e., they are not targeted to a specific organ, tissue, cell, or cell surface marker, rather they are administrated systemically.

According to the methods of the present invention, a composition comprising a soluble CD1d complex is administered to modulate an immune response in an animal, e.g., a vertebrate, e.g., a mammal, e.g., a human. In certain embodiments, the the methods of the present invention result in the enhancement of an immune response, e.g., to an immunogen delivered before, after, or concurrently with a soluble CD1d complex. Administration of soluble CD1d complexes of the invention, e.g., with an immunogen, may typically result in the release of a cytokines from immune cells, e.g., NKT cells or NK cells. Cytokines released in response to administration of compositions of the invention may be those associated with a TH1-type immune response, e.g., interferon gamma and TNF-alpha. Alternatively, or in addition, administration of compositions of the present invention may result in the release of cytokines associated with a TH2-type immune response, e.g., IL-4, IL-5, IL-10, or IL-13. Alternatively, or in addition, administration of compositions of the present invention may result in the release of other cytokines, e.g., IL-2, IL-1β, IL-12, IL-17, IL-23, TNF-β/LT, MCP-2, oncostatin-M, and RANTES. Methods to modulate the type of cytokines released include varying the ceramide-like glycolipid antigen of the soluble CD1d complex. Choosing and testing various ceramide-like glycolipid antigens for their effect on cytokine release from NKT or other immune cells may be performed using in vitro assays described elsewhere herein and in Porcelli, U.S. Patent Appl. Publ. No. 2006/0052316, as well as by additional methods well-known by those of ordinary skill in the art. Administration of soluble CD1d complexes of the present invention and compositions comprising same may further modulate an immune response by inducing proliferation of NKT cells, and also by inducing recruitment and or activation of other immune cells including, but not limited to NK cells, CTLs, other T lymphocytes, e.g., CD8+ or CD4+ T lymphocytes, dendritic cells, B lymphocytes, and others.

In certain embodiments, administration of soluble CD1d complexes of the present invention and compositions comprising same results in the suppression or inhibition of an undesired immune response, e.g., inflammation or autoimmunity.

In certain embodiments, administration of soluble CD1d complexes of the present invention and compositions comprising same affects one or more NKT cell activities such as, but not limited to cell proliferation, the production of one or more cytokines, or recruitment and/or activation of non-NKT immune system cells including, but not limited to NK cells, CTLs, other T lymphocytes, e.g., CD8+ or CD4+ T lymphocytes, dendritic cells, B lymphocytes, and others.

Certain embodiments of the present invention involve use of soluble CD1d complexes of the invention as adjuvants, i.e., to modulate an immune response to a specific immunogen. Accordingly, the present invention provides a method of modulating an immune response to an immunogen in an animal, where the method comprises administering to an animal in need of such modulation a composition comprising an immunogen, a soluble CD1d complex loaded with a ceramide-like glycolipid antigen as described elsewhere herein, and a suitable carrier. According to this embodiment, the soluble CD1d complex is administered in an amount sufficient to modulate the immune response against the immunogen relative to administration of the immunogen without the soluble CD1d complex. A soluble CD1d complex for use as an adjuvant as described herein may in certain embodiments be a non-specific soluble CD1d complex. In other embodiments, a soluble CD1d complex for use as an adjuvant may be targeted to a particular organ, tissue, cell or cell surface marker as described, e.g., in Bruno et al U.S. Patent Appl. Publ. No. 2006/0269540.

In certain embodiments, soluble CD1d complexes of the present invention and compositions comprising same are administered with an immunogen as a therapeutic vaccine, e.g., to an animal already suffering from a disease such as cancer. According to these methods, the immune response elicited by the immunogen/adjvant composition is effective in treating, e.g., affecting the outcome of the disease by reducing symptoms or lessening the severity of the disease, and the non-specific CD1d complex is administered in an amount sufficient to modulate the immune response against the immunogen relative to administration of the immunogen in the absence of the non-specific soluble CD1d complex. Alternatively, soluble CD1d complexes of the present invention and compositions comprising same are administered with an immunogen as a prophylactic vaccine, i.e., to prevent, or reduce symptoms to a disease, such as an infectious disease that might be contracted by that animal in the future. According to these methods, the immune response elicited by the immunogen/adjvant composition is effective in preventing, e.g., affecting the outcome of the disease by reducing symptoms or lessening the severity of the disease, and the non-specific CD1d complex is administered in an amount sufficient to modulate the immune response against the immunogen relative to administration of the immunogen in the absence of the non-specific soluble CD1d complex.

The present invention also provides immunogen/adjuvant compositions for use in the methods described herein. Such compositions comprise an immunogen and a soluble CD1d complex as described elsewhere herein. Immunogen/adjuvant compositions of the present invention typically include non-specific soluble CD1d complex, but may, in certain embodiments, include targeted soluble CD1d complexes.

The methods and compositions as described herein are useful for raising an immune response and treating hyperproliferative disorders. Examples of hyperproliferative disorders that can be treated by the compounds of the invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated by the compounds of the invention. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

The methods and compositions as described herein are also useful for raising an immune response against infectious agents. Viruses are one example of an infectious agent that can cause disease or symptoms that can be treated by the compounds of the invention. Examples of viruses, include, but are not limited to the following DNA and RNA viral families: Arbovirus, Adenoviridae, Arenaviridae, Arterivirus, Bimaviridae, Bunyaviridae, Caliciviridae, Circoviridae, Coronaviridae, Flaviviridae, Hepadnaviridae (hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picomaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, measles, mumps, parainfluenza, rabies, the common cold, Polio, leukemia, Rubella, sexually transmitted diseases, skin diseases (e.g., Kaposi's, warts), and viremia.

Similarly, bacterial or fungal agents that can cause disease or symptoms can be treated or prevented by the methods and compositions of the invention. These include, but are not limited to, the following Gram-Negative and Gram-positive bacterial families and fungi: Actinomycetales (e.g., *Corynebacterium, Mycobacterium, Norcardia*), Aspergillosis, Bacillaceae (e.g., Anthrax, *Clostridium*), Bacteroidaceae, Blastomycosis, *Bordetella, Borrelia,* Brucellosis, Candidiasis, *Campylobacter,* Coccidioidomycosis, Cryptococcosis, Dermatocycoses, Enterobacteriaceae (*Klebsiella, Salmonella, Serratia, Yersinia*), Erysipelothrix, *Helicobacter,* Legionellosis, Leptospirosis, *Listeria,* Mycoplasmatales, Neisseriaceae (e.g., *Acinetobacter,* Gonorrhea, Menigococcal), Pasteurellacea Infections (e.g., *Actinobacillus,* Heamophilus, *Pasteurella*), *Pseudomonas,* Rickettsiaceae, Chlamydiaceae, Syphilis, and *Staphylococcal*. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections.

Moreover, the methods and compositions of the present invention may be used to treat or prevent diseases caused by parasitic agents. These include, but are not limited to that can be treated by the compounds of the invention include, but are not limited to, the following families: amebiasis, babesiosis, coccidiosis, cryptosporidiosis, dientamoebiasis, dourine, ectoparasitic, giardiasis, helminthiasis, leishmaniasis, theileriasis, toxoplasmosis, trypanosomiasis, and trichomonas.

Additionally, the methods and compositions of the present invention may be used to treat or prevent autoimmune diseases. An autoimmune disease is characterized by the attack by the immune system on the tissues of the victim. In autoimmune diseases, the recognition of tissues as "self" apparently does not occur, and the tissue of the afflicted subject is treated as an invader—i.e., the immune system sets about destroying this presumed foreign target. The compounds of the present invention are therefor useful for treating autoimmune diseases by desensitizing the immune system to these self antigens by, for example, immune deviation away from a destructive HG1 type response.

Examples of autoimmune diseases which may be treated using the compounds of the present invention include, but are not limited to Addison's Disease, hemolytic anemia, antiphospholipid syndrome, rheumatoid arthritis, dermatitis, allergic encephalomyelitis, glomerulonephritis, Goodpasture's Syndrome, Graves' Disease, multiple sclerosis, myasthenia gravis, neuritis, ophthalmia, bullous pemphigoid, pemphigus, polyendocrinopathies, purpura, Reiter's Disease, Stiff-Man Syndrome, autoimmune thyroiditis, systemic lupus erythematosus, autoimmune pulmonary inflammation, Guillain-Barre Syndrome, insulin dependent diabetes mellitis, autoimmune inflammatory eye disease, autoimmune hemolysis, psoriasis, juvenile diabetes, primary idiopathic myxedema, autoimmune asthma, scleroderma, chronic hepatitis, hypogonadism, pernicious anemia, vitiligo, alopecia areata, Coeliac disease, autoimmune enteropathy syndrome, idiopathic thrombocytic purpura, acquired splenic atrophy, idiopathic diabetes insipidus, infertility due to antispermatazoan antibodies, sudden hearing loss, sensoneural hearing loss, polymyositis, autoimmune demyelinating diseases, traverse myelitis, ataxic sclerosis, progressive systemic sclerosis, dermatomyositis, polyarteritis nodosa, idiopathic facial paralysis, cryoglobulinemia, inflammatory bowel diseases, Hashimoto's disease, adrenalitis, hypoparathyroidism, and ulcerative colitis.

Similarly, allergic reactions and conditions, such as asthma (particularly allergic asthma) or other respiratory problems, may also be treated by the methods and compositions of the invention. In one embodiment, the invention provides for effective delivery of signals that inhibit or skew cytokine production by NKT cells resulting in reduced immune responses or immune deviation. For example, the methods and compositions of the invention can be used to treat anaphylaxis, hypersensitivity to an antigenic molecule, or blood group incompatibility.

The methods and compositions of the invention may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of the compounds of the invention that inhibit or result in immune deviation of an immune response may be an effective therapy in preventing organ rejection or GVHD.

Certain compositions of the invention described elsewhere herein which can inhibit an immune response upon administration are also useful for treating and/or preventing atherosclerosis; olitis; regional enteritis; adult respiratory distress syndrome; local manifestations of drug reactions, such as dermatitis, etc.; inflammation-associated or allergic reaction patterns of the skin; atopic dermatitis and infantile eczema; contact dermatitis; psoriasis; lichen planus; allergic enteropathies; allergic rhinitis; bronchial asthma; hypersensitivity or destructive responses to infectious agents; post-streptococcal diseases, e.g. cardiac manifestations of rheumatic fever, and the like.

According to the disclosed methods, compositions for use in the methods of the present invention can be administered, for example, by intramuscular (i.m.), subcutaneous (s.c.), or intrapulmonary routes. Other suitable routes of administration include, but are not limited to intratracheal, transdermal, intraocular, intranasal, inhalation, intracavity, intravenous (i.v.), intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), inraatrial (i.e., into the heart atrium) and sub arachnoid (i.e., into the sub arachnoid spaces of the brain) administration.

Pharmaceutical Compositions

Soluble CD1d complexes of the present invention may be administered in pharmaceutical compositions either with our without an immunogen, in combination with one or more pharmaceutically acceptable excipients. It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition of another agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts. Suitable formulations, known in the art, can be found in Remington's Pharmaceutical Sciences (latest edition), Mack Publishing Company, Easton, Pa.

A pharmaceutical composition to be used in a given therapeutic treatment will be formulated and dosed in a fashion consistent with good medical practice, taking into account the clinical condition of the individual patient (especially the side effects of treatment with the compounds alone), the site of delivery of the compound, the method of administration, the scheduling of administration, and other factors known to practitioners. The "effective amount" of the compounds of the invention for purposes herein is thus determined by such considerations.

Pharmaceutical compositions of the invention may be administered orally, intravenously, rectally, parenterally, intracistemally, intradermally, intravaginally, intraperitoneally, topically (as by powders, ointments, gels, creams, drops or transdermal patch), bucally, or as an oral or nasal spray. The term "parenteral" as used herein refers to modes of administration which include intravenous, intramuscular, intraperitoneal, intrasternal, subcutaneous and intraarticular injection and infusion.

The pharmaceutical compositions are administered in an amount which is effective for treating and/or prophylaxis of the specific indication. In most cases, the dosage is from about 1 µg/kg to about 30 mg/kg body weight daily, taking into account the routes of administration, symptoms, etc. However, the dosage can be as low as 0.001 µg/kg.

As a general proposition, the total pharmaceutically effective amount of the compositions administered parenterally per dose will be in the range of about 1 µg/kg/day to 100 mg/kg/day of patient body weight, although, as noted above, this will be subject to therapeutic discretion. If given continuously, the composition is typically administered at a dose rate of about 1 µg/kg/hour to about 5 mg/kg/hour, either by 1-4 injections per day or by continuous subcutaneous infusions, for example, using a mini-pump. An intravenous bag solution or bottle solution may also be employed.

The compositions of the invention may also be suitably administered by sustained-release systems. Suitable examples of sustained-release compositions include semipermeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (U. Sidman et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained-release compositions also include liposomally entrapped compositions of the present invention. Liposomes are prepared by methods known per se: DE 3,218,121; Epstein, et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, in one embodiment, a composition of the invention is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compositions that are known to be deleterious to polypeptides.

Generally, the formulations are prepared by contacting a soluble CD1d complex and optionally an immunogen of the invention uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Suitable formulations, known in the art, can be found in Remington's Pharmaceutical Sciences (latest edition), Mack Publishing Company, Easton, Pa.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The compositions are typically formulated in such vehicles at a non-limiting concentration of about 0.01 µg/ml to 100 mg/ml, for example about 0.01 µg/ml to 10 mg/ml, at a pH of about 3 to 8. It will be understood that the use of certain of the foregoing excipients, carriers, or stabilizers will result in the formation of salts.

Compositions to be used for therapeutic administration must be sterile. Sterility is readily accomplished by filtration through sterile filtration membranes (e.g., 0.2 micron membranes). Therapeutic compositions generally are placed into a container having a sterile access port, for example, an intravenous solution bag or vial having a stopper pierceable by a hypodermic injection needle.

Compositions of the invention ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized composition using bacteriostatic Water-for-Injection.

Dosaging may also be arranged in a patient specific manner to provide a predetermined concentration of activity in the blood, as determined by an RIA technique, for instance. Thus patient dosaging may be adjusted to achieve regular on-going trough blood levels, as measured by RIA, on the order of from 50 to 1000 ng/ml, preferably 150 to 500 ng/ml.

Compositions of the invention are useful for administration to any animal, preferably a mammal (such as apes, cows, horses, pigs, boars, sheep, rodents, goats, dogs, cats, chickens, monkeys, rabbits, ferrets, whales, and dolphins), and more preferably a human.

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration. In addition, the compositions of the present invention may be employed in conjunction with other therapeutic compositions.

Other therapeutic compositions useful for administration along with a composition of the present invention include cytotoxic drugs, particularly those which are used for cancer therapy. Such drugs include, in general, alkylating agents, anti-proliferative agents, tubulin binding agents and the like. Preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, carminomycin, daunorubicin, aminopterin, methotrexate, methopterin, dichloromethotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine and the like. As noted previously, one skilled in the art may make chemical modifications to the desired compound in order to make reactions of that compound more convenient for purposes of preparing conjugates of the invention.

The compositions of the invention can be used to treat tumor-bearing animals, including humans, to generate an immune response against tumor cells. The generation of an adequate and appropriate immune response leads to tumor regression in vivo. Such "vaccines" can be used either alone or in combination with other therapeutic regimens, including but not limited to chemotherapy, radiation therapy, surgery, bone marrow transplantation, etc. for the treatment of tumors. For example, surgical or radiation techniques could be used to debulk the tumor mass, after which, the vaccine formulations of the invention can be administered to ensure the regression and prevent the progression of remaining tumor masses or micrometastases in the body. Alternatively, administration of the "vaccine" can precede such surgical, radiation or chemotherapeutic treatment.

Alternatively, the compositions of the invention can be used to immunize or "vaccinate" tumor-free subjects to prevent tumor formation. With the advent of genetic testing, it is now possible to predict a subject's predisposition for certain cancers. Such subjects, therefore, may be immunized using a compound comprising one or more antigenic ligands derived from tumors.

Suitable preparations of such vaccines include injectables, either as liquid solutions or suspensions; solid forms suitable for solution in, or suspension in liquid prior to injection, may also be prepared. The preparation may also be emulsified, or the polypeptides encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

Compositions of the present invention which comprise a soluble CD1d complex and an immunogen may further comprise additional adjuvants. Examples of adjuvants which may be effective, include, but are not limited to: aluminum hydroxide, N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, GM-CSF, QS-21 (investigational drug, Progenics Pharmaceuticals, Inc.), DETOX (investigational drug, Ribi Pharmaceuticals), BCG, and CpG rich oligonucleotides.

Compositions of the present invention which comprise a soluble CD1d complex and an immunogen may further comprise additional adjuvants which are also Toll-like receptor (TLR) agonists. Examples of TLR agonist adjuvants which may be effective, include, but are not limited to: N-acetylmuramyl-L-alanine-D-isoglutamine (MDP), lipopolysaccharides (LPS), genetically modified and/or degraded LPS, alum, glucan, colony stimulating factors (e.g., EPO, GM-CSF, G-CSF, M-CSF, PEGylated G-CSF, SCF, IL-3, IL6, PIXY 321), interferons (e.g., γ-interferon, α-interferon), interleukins (e.g., IL-2, IL-7, IL-12, IL-15, IL-18), saponins (e.g., QS21), monophosphoryl lipid A (MPL), 3 De-O-acylated monophosphoryl lipid A (3D-MPL), unmethylated CpG sequences, 1-methyl tryptophan, arginase inhibitors, cyclophosphamnide, antibodies that block immunosuppressive functions (e.g., anti-CTLA4 antibodies), lipids (such as palmitic acid residues), tripalmitoyl-S-glycerylcystein lyseryl-serine (P₃ CSS), and Freund's adjuvant. Other adjuvant examples include compounds such as isatoribin and it derivatives (Anadys Pharmaceuticals) or imidazoquinolinamines, such as imiquimod and resiquimod (Dockrell & Kinghom, *J. Antimicrob. Chemother.,* 48:751-755 (2001) and Hemmi et al., *Nat. Immunol.,* 3:196-200 (2002), guanine ribonucleosides, such as C8-substituted or N7, C-8-disubstituted guanine ribonucleosides (Lee et al., *Proc. Natl. Acad. Sci. USA,* 100:6646-6651 (2003) and the compounds that are disclosed in Pat. Pub. Nos. JP-2005-089,334; WO99/32122; WO98/01448 WO05/092893; and WO05/092892, and TLR-7 agonist SM360320 (9-benzyl-8-hydroxy-2-(2-methoxy-ethoxy)adenine) disclosed in Lee et al., *Proc Natl Acad Sci USA,* 103(6):1828-1833 (2006).

In addition to isatoribin, other TLR agonist adjuvants include 9-benzyl-8-hydroxy-2-(2-methoxyethoxy)adenine (SM360320), Actilon™ (Coley Pharmaceutical Group, Inc.), and the following compounds by Sumitmo Pharmaceutical Co, Ltd.:

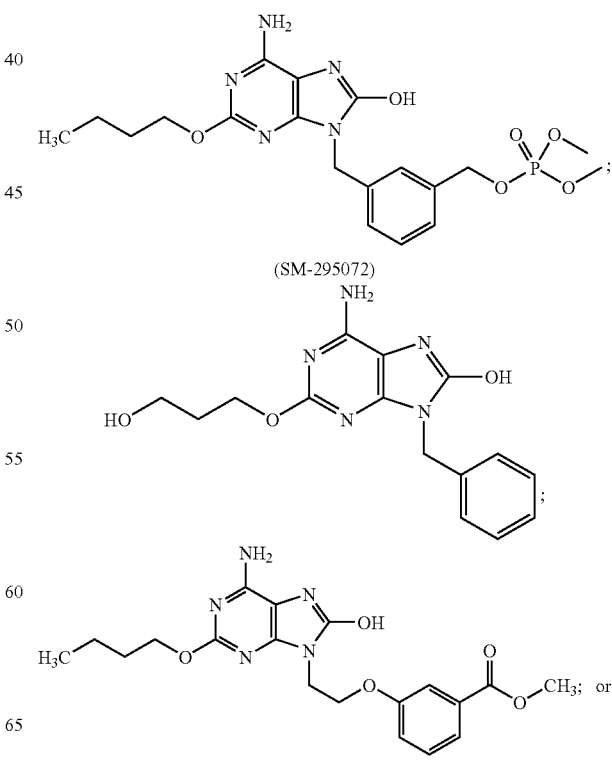

-continued

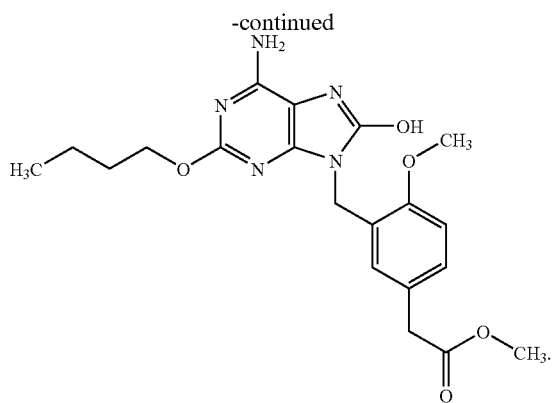

Other adjuvants which may be used in conjunction with the composition of the present invention are disclosed in PCT Pub. No. WO 2005/000348, U.S. Pat. Pub. No. 2007/0292418, and U.S. Pat. Pub. No. 2007/0287664.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

In an alternate embodiment, compositions of the present invention may be used in adoptive immunotherapeutic methods for the activation of NKT lymphocytes that are histocompatible with the patient. (for methods of adoptive immunotherapy, see, e.g., Rosenberg, U.S. Pat. No. 4,690,915, issued Sep. 1, 1987; Zarling, et al., U.S. Pat. No. 5,081,029, issued Jan. 14, 1992). Such NKT lymphocytes may be isolated from the patient or a histocompatible donor. The NKT lymphocytes are activated in vitro by exposure to a composition of the invention. Activated NKT lymphocytes are expanded and inoculated into the patient in order to transfer NKT cell immunity directed against the particular antigenic peptide or peptides.

The compositions of the present invention may further comprise other compounds which modulate an immune response, for example, cytokines. The term "cytokine" refers to polypeptides, including, but not limited to, interleukins (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, and IL-18), α interferons (e.g., IFN-α), β interferon (IFN-β), γ interferons (e.g., IFN-γ), colony stimulating factors (CSFS, e.g., CSF-1, CSF-2, and CSF-3), granulocyte-macrophage colony stimulating factor (GMCSF), transforming growth factor (TGF, e.g., TGFα and TGFβ), and insulin-like growth factors (IGFs, e.g., IGF-I and IGF-II).

In certain embodiments, therapeutic compositions useful in systemic administration, include soluble CD1d complexes of the present invention complexed to a delivery vehicle. Suitable delivery vehicles for use with systemic administration comprise liposomes comprising ligands for targeting the vehicle to a particular site, for example, ligands for targeting the vehicle to a tissue of interest. Targeting vehicles for other tissues and organs are well known to skilled artisans. In other embodiments, soluble CD1d complexes of the present invention are non-specific, i.e., they are not targeted to any particular tissue, organ, cell, or cell surface marker.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189: 11277-11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); Molecular Cloning: A Laboratory Manual, Sambrook et al., ed., Cold Springs Harbor Laboratory, New York (1992), DNA Cloning, D. N. Glover ed., Volumes I and II (1985); Oligonucleotide Synthesis, M. J. Gait ed., (1984); Mullis et al. U.S. Pat. No. 4,683,195; Nucleic Acid Hybridization, B. D. Hames & S. J. Higgins eds. (1984); Transcription And Translation, B. D. Hames & S. J. Higgins eds. (1984); Culture Of Animal Cells, R. I. Freshney, Alan R. Liss, Inc., (1987); Immobilized Cells And Enzymes, IRL Press, (1986); B. Perbal, A Practical Guide To Molecular Cloning (1984); the treatise, Methods In Enzymology, Academic Press, Inc., N.Y.; Gene Transfer Vectors For Mammalian Cells, J. H. Miller and M. P. Calos eds., Cold Spring Harbor Laboratory (1987); Methods In Enzymology, Vols. 154 and 155 (Wu et al. eds.); Immunochemical Methods In Cell And Molecular Biology, Mayer and Walker, eds., Academic Press, London (1987); Handbook Of Experimental Immunology, Volumes I-IV, D. M. Weir and C. C. Blackwell, eds., (1986); Manipulating the Mouse Embryo, Cold Spring Harbor Laboratory Press, Cold Spring Harbor, N.Y., (1986); and in Ausubel et al., Current Protocols in Molecular Biology, John Wiley and Sons, Baltimore, Md. (1989).

General principles of antibody engineering are set forth in Antibody Engineering, 2nd edition, C.A.K. Borrebaeck, Ed., Oxford Univ. Press (1995). General principles of protein engineering are set forth in Protein Engineering, A Practical Approach, Rickwood, D., et al., Eds., IRL Press at Oxford Univ. Press, Oxford, Eng. (1995). General principles of antibodies and antibody-hapten binding are set forth in: Nisonoff, A., Molecular Immunology, 2nd ed., Sinauer Associates, Sunderland, Mass. (1984); and Steward, M. W., Antibodies, Their Structure and Function, Chapman and Hall, New York, N.Y. (1984). Additionally, standard methods in immunology known in the art and not specifically described are generally followed as in Current Protocols in Immunology, John Wiley & Sons, New York; Stites et al. (eds), Basic and Clinical-Immunology (8th ed.), Appleton & Lange, Norwalk, Conn. (1994) and Mishell and Shiigi (eds), Selected Methods in Cellular Immunology, W.H. Freeman and Co., New York (1980).

Standard reference works setting forth general principles of immunology include Current Protocols in Immunology, John Wiley & Sons, New York; Klein, J., Immunology: The Science of Self-Nonself Discrimination, John Wiley & Sons, New York (1982); Kennett, R., et al., eds., Monoclonal Antibodies, Hybridoma: A New Dimension in Biological Analyses, Plenum Press, New York (1980); Campbell, A., "Monoclonal Antibody Technology" in Burden, R., et al., eds., Laboratory Techniques in Biochemistry and Molecular Biology, Vol. 13, Elsevere, Amsterdam (1984), Kuby Immunology 4th ed. Ed. Richard A. Goldsby, Thomas J. Kindt and Barbara A. Osborne, H. Freemand & Co. (2000); Roitt, I., Brostoff, J. and Male D., Immunology 6th ed. London: Mosby (2001); Abbas A., Abul, A. and Lichtman, A., Cellular and Molecular Immunology Ed. 5, Elsevier Health Sciences Division (2005); Kontermann and Dubel, Antibody Engineering, Springer Verlan (2001); Sambrook and Russell, Molecular Cloning: A Laboratory Manual. Cold Spring Harbor Press (2001); Lewin, Genes VIII, Prentice Hall (2003); Harlow and Lane, Antibodies: A Laboratory Manual, Cold Spring Harbor Press (1988); Dieffenbach and Dveksler, PCR Primer Cold Spring Harbor Press (2003).

All of the references cited above, as well as all references cited herein, are incorporated herein by reference in their entireties.

EXAMPLES

Materials and Methods

Construction of soluble β2m-CD1d ("CD1d") and β2m-CD1d-4D5 scFv fusion ("CD1d fusion") proteins. Mouse beta2-microglobulin (β2m), soluble CD1, and the murine anti-HER2 antibody single chain 4D5 scFv were cloned by PCR. Total RNA was extracted from the CD1d transfected mouse RMA.S cell line using the RNeasy Mini Kit (QIAGEN). For the anti-HER2 antibody part, the plasmid pIG6-4D5 containing the scFv fragment derived from the mouse anti-HER2 antibody 4D5 was used as template (Worn, A., and Pluckthun, A. *FEBS Lett:* 427, 357-361 (1998)). Briefly, the entire mouse β2m was amplified with a Hind III site at the N-terminus for subsequent cloning in the PEAK 8 expression vector (EdgeBiosystems, MD, USA) and an Nhe I site at its C-terminus for its ligation to the N-terminal sequence of the α1 domain of CD1d with the insertion of a sequence encoding a flexible glycine/serine-rich peptide linker (GGGGSGGSGSGGG (SEQ ID NO:12)). The primers used for this PCR were 5!-TTAAGCTT ATGGCTCGCTCGGTGA (SEQ ID NO:13) and 5'AAGA-TATCGCTAGCTCCACCTCCAGA-ACCGGATCCACCTGATCCACCTC CACCCATGTCTC-GATCCCAGTAGA (SEQ ID NO:14). The C-terminus of the soluble CD1d fragment was either directly fused to a 6×His tag via a small linker (SSGSGG (SEQ ID NO:15)) (for soluble β2m-CD1d) or ligated to the N-terminus of the 4D5 scFv fragment via the same flexible linker as above (GGGGSGGSGSGGG (SEQ ID NO:12)) and a Nar I restriction site (for the CD1d-4D5 fusion). The primers for this PCR were 5'-TTCTCGAGGCTAGCCAGCAAAA GAATTACACCTTC (sense, SEQ ID NO:16) and 5'-TT-GAATTCGGCGCCTCCACCTCCAG-AACCGGATCCACCTGATCCACCTCCA CCGC-CCACGGGTGCTTGCCTGGCAT (reverse, SEQ ID NO:17). The DNA fragment for the anti-HER2 4D5 scFv was fused at the C-terminus to the small glycine-/serine-rich linker (SSGSGG (SEQ ID NO:18) followed by the 6×His tag, a stop codon and a Not I site for subcloning. The PCR primers were 5'-TTCTCGAG GGCGCCGACTACAAAGATATCGTTAT (sense, SEQ ID NO:19) and 5'-AAGCGGCCGCTTAA-TGGTGGTGATGATGATGTCCTCCAGAACCAGAAG AA ACGGTAACGGTGGTA (reverse, SEQ ID NO:20). PCR was performed using Pwo Polymerase (Roche) and amplified DNA fragments were cloned into pCR®-Blunt vector (Invitrogen) and sequenced to ensure no mutation was introduced. Using the described restriction sites, a two or three-part ligation reaction was performed to join the β2m and linker to the soluble CD1d and, in the case of the fusion, to the 4D5 scFv DNA part with concomitant subcloning into the pEAK8 expression vector (EdgeBiosystems).

Recombinant protein production by transient transfection. The human cell line HEK293EBNA was adapted to serum-free suspension growth in Excell™-293 medium (JRH Biosciences, Lexana, Kans.) in 1-liter glass bottles placed on an orbital shaker (Kühner AG, Switzerland). For large scale transfection in suspension cultures, cells were seeded in serum-free RPMI medium (with 25 mM Hepes, Cambrex Biosciences, Verviers, Belgium) at a density of 2×10⁶ cells/ml, and transfected using linear 25-kD polyethyleneimine, as described in Baldi, L., et al. *Biotechnol Prog* 21:148-153 (2005). The addition to the DNA/PEI mix of 1% (corresponding to 25 ng/ml) pEGFP-N1 plasmid DNA (Clontech, Palo Alto, Calif.) allowed direct visual estimation of transfection efficiency under a fluorescence light microscope (Zeiss Axiovert). Four hours post-transfection, the culture was diluted by adding one volume of Pro-293s medium (Cambrex). After 6 days, the culture was centrifuged, and the supernatant was saved for protein purification.

Affinity purification of recombinant proteins and αGalCer loading on CD1d. The His-tagged soluble CD1d and the CD1d-4D5 fusion proteins were purified from the HEK293 supernatants using Ni—NTA resin batch-wise (Ni—NTA Superflow, QIAGEN) and bound proteins were eluted with 0.25 M Imidazole. Purity was analyzed on a 10% SDS-PAGE. Depending the batch, the yield could reach up to10 mg/L supernatant of pure soluble or anti-HER2 CD1d fusion proteins. After purification, CD1d was loaded overnight at RT with a three-fold molar excess of αGalCer and the unbound glycolipid was removed by FPLC (SUPERDEX™ 200 or Sephacryl S100, Pharmacia Biotech). Binding to the HER2 tumor antigen and proper folding of the CD1d protein were assessed on the B16-HER2 and SKBR3 target cell lines by flow cytometry using either an anti-His or anti-CD1d mAbs (BD Biosciences).

Generation of CD1d tetramer. For this purpose, the soluble β2m-CD1d molecule was modified at the C-terminus by the addition of a cysteine after the stretch of histidine residues. After a mild reduction with 0.5 mM β-mercaptoethanol for 30 min at 30C and purification on a PD10 desalting column, the pure recombinant protein was biotinylated on the cystein residue by the chemical coupling of a biotin-maleimide linker (EZ-linked BM, Pierce) in 2M excess overnight at RT. The excess of linker was removed by gel filtration on a SUPERDEX™S200 column (Pharmacia Biotech). The biotinylated CD1d was loaded with αGalCer as described above and was tetramerized on EXTRAVI-DIN®-PE (Sigma) and resulting complex was used at 5 μg/ml for NKT cell staining.

Mice, cell lines and antibodies. Female mice C57BL/6, 6-8 weeks old, were purchased from Harlan (Zeist, Holland).

The B16-F10 melanoma cell line (ATCC/CRL-6475) was stably transfected with the human HER2 antigen (Cesson, V., et al. *Clin Cancer Res* 12:7422-7430 (2006)). Transfected cells were selected with 1.2 mg/ml G418 and grafted intravenously (i.v.) into naïve mice. High HER2 expressing clones were established from lung metastases and expanded in DMEM supplied with 10% FCS, antibiotics and 1.2 mg/ml G418. Expression of HER2 was monitored by flow cytometry (BD FACScan) with 10 μg/ml of the humanized anti-HER2 monoclonal antibody HERCEPTIN®(TRASTU-ZUMAB, Hoffmann-La-Roche) and goat anti-human IgG-FITC (Sigma). All other antibodies, unless specified, were from Becton Dickinson (BD Biosciences). The software used was CELLQUEST™ (BD Biosciences).

Isolation of liver, lung and spleen lymphocytes. Mouse livers and lungs were homogenized with 100 μm strainer and lymphocytes were isolated using a PERCOLL™ density gradient (Amersham Biosciences). After two washings, cells were either re-challenged or directly analyzed by fluorescence cytometry. Spleens were homogenized with a 70 μm strainer, debris were eliminated by spontaneous sedimentation and splenocytes were recovered by centrifugation. They were then depleted from B cells by incubation with anti-CD19 MACS microbeads and elution on LD columns according to manufacturer recommendation (Myltenyi Biotec).

Serum cytokines. Serum TNFα was measured by the QUANTIKINE® immunoassay kit from R&D Systems Inc. (Minneapolis, USA).

Quantification of lung metastasis. Metastatic nodule surface area was measured on 2560×1920 pixels photographs of the whole organs, taken on an Zeiss STEMI SV11 dissection microscope (Carl Zeiss, Jena, Germany) equipped with a PROGRES-C10plus Color Camera (Jenoptik, Jena, Germany). Each image was analyzed with the ImageJ program (rsb.info.nih.gov/ij/) using a k-means clustering algorithm (plugin available on ij-plugins.sourceforge.net). Images were segmented into 9 segments cluster tolerance 1×10−4, randomization seed: 48) and the appropriate segments were selected based on the color of the metastasis reaching the surface of the organ. The area of the sum of selected color segments was expressed as percentage of the area occupied by the lungs. Both sides of the lung were analyzed. This method takes into account both the number and the size of the tumor nodules. Since nodules are often heterogenous the percentage of metastatic lung surface area is a more sensitive measure of tumor growth than just counting tumor nodules.

Example 1

Sustained Activation of iNKT Cells with Repeated Injections of Recombinant αGalCer-Loaded CD1d Molecules This Example demonstrates that a soluble monomeric form of CD1d loaded with αGalCer can fully activate mouse iNKT cells in vitro and in vivo and that this activation is due to the complex per se and not to the in vivo release of αGalCer. In particular, this Example shows that iNKT cells remain responsive following repeated injections of αGalCer/sCD1d and αGalCer/CD1d-anti HER2 (αGalCer/sCD1d linked to a scFv fragment of anti-Her2 antibody). This is in sharp contrast to stimulation with αGalCer alone, which was previously shown to induce unresponsiveness after a single injection. Parameters of iNKT activation include invTCR (the invariant T cell receptor of NKT cells) downmodulation, production of IFNγ, increased iNKT frequency during systemic treatment and resistance to tumor development after pretreatment.

InvTCR downmodulation: free αGalCer (5 μg), sCD1d (20 μg) and CD1d-anti HER2 fusion (40 μg), loaded or not with αGalCer, were injected intraperitoneally into 6 groups of 5 mice. Mice were sacrificed 20 hours later. Liver lymphocytes were prepared as described above and stained with αGalCer/CD1d tetramer+anti-CD3 for analysis by FACS. FIG. 1 shows that inv TCR downmodulation occurred following a single injection of either free αGalCer or recombinant CD1d molecules loaded with αGalCer. The following experiments demonstrate that this result is not due to the in vivo release of αGalCer but is due to direct stimulation by the complex per se since the outcome of the two modes of stimulation differ.

Figure 2:
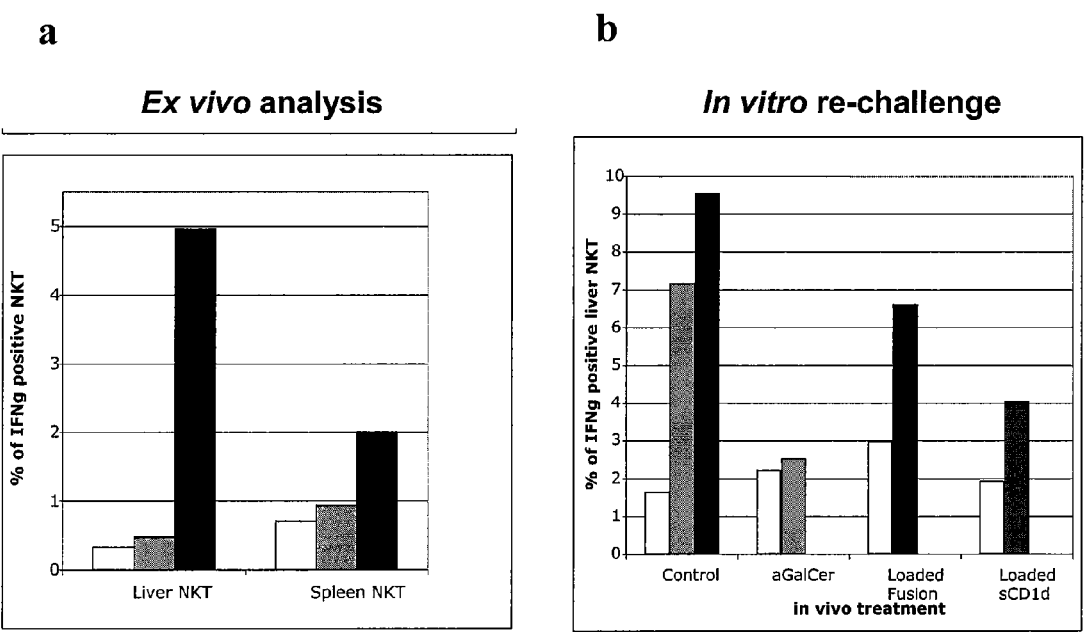

Sustained production of IFNγ after repeated i.v. injections: cytokine production was tested by IntraCellular Cytokine Staining (ICCS). Liver and spleen lymphocytes ($2 \times 10^6$/ml) from treated mice (5 to 6 i.v. injections every three days) were activated "in vitro" or "ex vivo" by either 200 ng/ml αGalCer or by αGalCer/CD1d-anti HER2 fusion (10 μg/ml) bound to plastic-coated anti-His antibody. GOLGI PLUG™ (BD) was added after 1 hour to block secretion and after a total of 6 hours incubation, activated lymphocytes were stained with different antibody combinations to gate on NKT cells. Anti-CD3-FITC was generally tested with αGalCer-CD1d tetramer-PE or, in case of NKT TCR downmodulation, anti-CD3-FITC was used with NK1.1-PerCP. After fixation and permeabilization with CYTOFIX/CYTOPERM™ (BD), intracellular IFNγ was detected with an APC-labeled anti-IFNγ monoclonal antibody. Cells were analyzed by flow cytometry on a FACS Calibur (CELLQUEST™ Software; BD). For ex vivo measurement following an i.v. injection, the procedure was similar except that the six hour incubation was omitted. FIG. 2 summarizes the results. For "ex vivo" measurements, liver and spleen cells were analyzed (FIG. 2*a*), whereas for "in vitro" analysis, data show only liver cells (FIG. 2*b*). Results demonstrate that in the two settings, the αGalCer/CD1d-anti HER2 fusion and the soluble αGalCer/sCD1d stimulate iNKT to produce IFNγ following repeated in vivo stimulation with the same material, whereas free αGalCer is only active in naïve (PBS control) mice and has no more effect in αGalCer-treated mice. No significant amount of IL-4 was measured in any of the mice (data not shown), suggesting that under these conditions, activated iNKT cells develop a pro-inflammatory cytokine bias.

Figure 3:
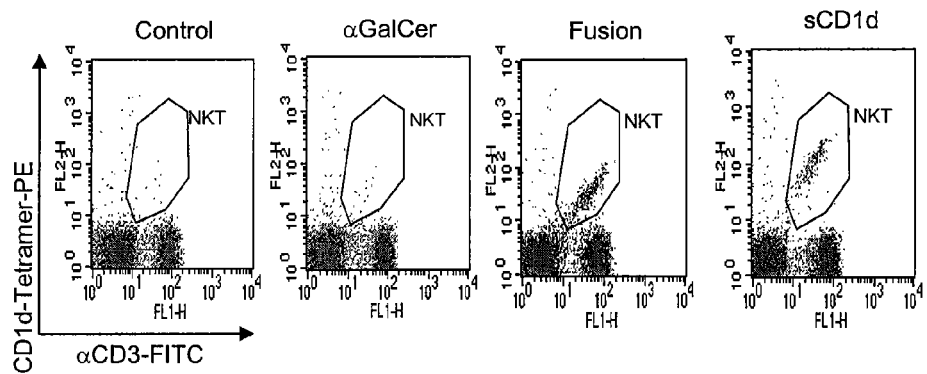
FIG. 3: iNKT expansion in blood during systemic treatment with αGalCer loaded recombinant CD1d molecules. Mice were bled after the third injection of either PBS (control) αGalCer (0.4 µg), αGalCer/CD1d-anti-Her2 fusion protein (Fusion, 40 µg), or αGalCer/sCD1d (sCD1d, 20 µg). NKT cells were stained in PBMCs using the CD1d-Tetramer-PE and anti CD3 FITC antibody. a representative dot blot of one mouse from each group. b graph representing several mice per group expressed as CD1d tetramer positive and CD3+ cells as percentage of total PBMC.
Figure 3:
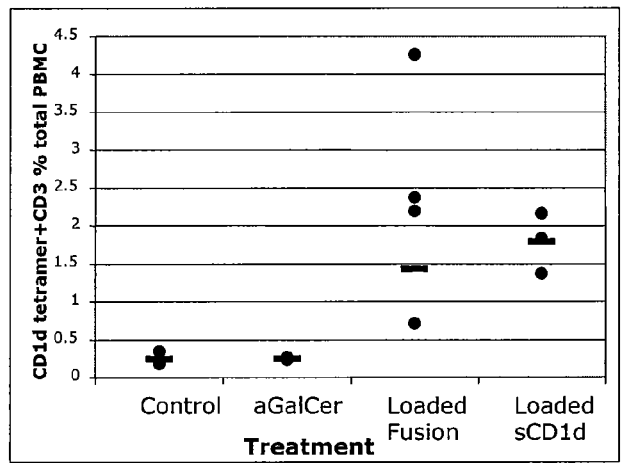

Increased frequency of iNKT cells during systemic treatment: normally iNKT cells are not detectable in mouse peripheral blood as shown on FIG. 3. In contrast, they became clearly detectable upon systemic treatment with recombinant αGalCer/CD1d molecules, whereas there was no change with αGalCer alone. FIG. 3*a* gives representative dot plots of FACS staining with CD1d-tetramer+anti-CD3 on PBMC 3 days after the third injection with either PBS, free αGalCer, αGalCer/CD1d-anti HER2, or αGalCer/sCD1d (five mice per group, i.v., injection every 3 days). Percentages of iNKT are given in FIG. 3*b*.

Figure 4:
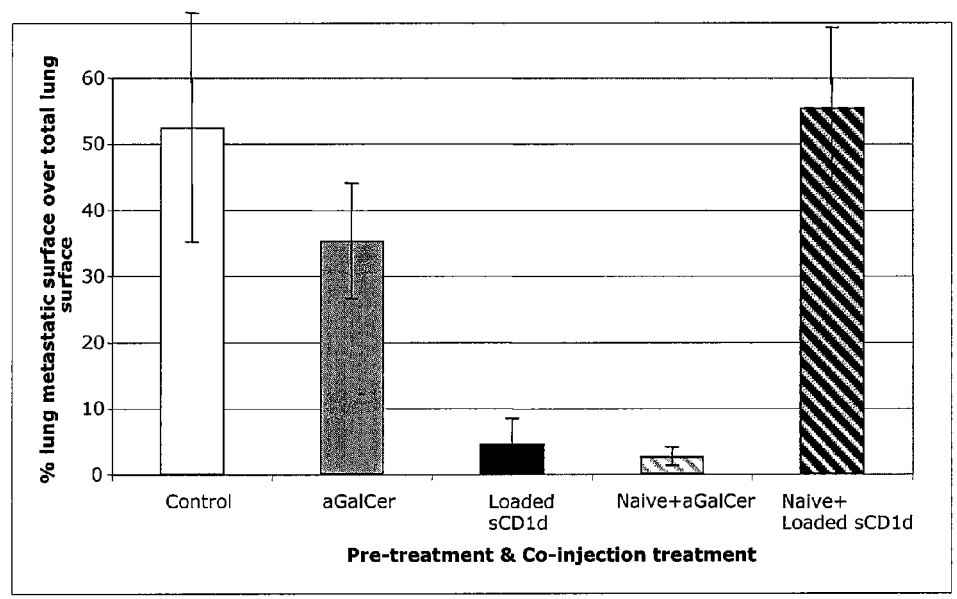
FIG. 4: Sustained iNKT activation in vivo due to repeated injections of αGalCer/sCD1d prevents formation of lung metastases. Mice were treated 5 times with PBS (Control, white), αGalCer (0.4 µg, light grey), or αGalCer/sCD1d (sCD1d, 20 µg, black) and then grafted with 700,000 B16 wild type cells plus co-injection of the respective treatment. 2 naive groups were included that had no pretreatment and got only tumor cell graft+co-injection of αGalCer (striped grey) or αGalCer/sCD1d (sCD1d, dark striped grey) respectively. Lung metastases formation was analysed 2 weeks after graft with the ImageJ k-means clustering program and results are expressed as percent of black metastatic surface over total lung surface. P values for αGalCer/sCD1d pretreated and naive+αGalCer groups compared to control *P<0.04, and compared to αGalCer pretreated group *P<0.02.

Pretreatment generates tumor protection: the sustained activation of iNKT cells by recombinant αGalCer/CD1d molecules was further demonstrated by the following experiment. Pretreatment of mice with five sequential i.v. injections of αGalCer/sCD1d (5×25 μg every 3 days) rendered them resistant to B16 melanoma cells (700,000 cells) co-injected with αGalCer/sCD1d (25 μg) (FIG. 4). As previously reported by Parekh et al. Parekh, V. V. et al. *J Clin*

*Invest* 115:2572-2583 (2005), mice pretreated with free αGalCer (5×0.4 μg) were not able to block lung metastasis when αGalCer was co-injected with the tumor cells. This is most likely due to the anergic state of iNKT cells induced by free αGalCer. In contrast, in naïve mice, opposite results were obtained. Co-injection of αGalCer alone completely blocked tumor development, while co-injection of αGalCer/sCD1d had no effect. The key finding is that multiple prior injections of αGalCer loaded recombinant CD1d molecules but not of free αGalCer confers resistance to tumor development. This supports a sustained activation of iNKT cells exhibiting cytotoxic activity against tumor cells directly and/or indirectly through activation of other cells such as NK cells.

Example 2

The αGalCer/CD1d-anti HER2 Fusion Protein has Anti Tumor Activity when Targeted to HER2-Expressing Tumors This Example demonstrates that the sustained activation of iNKT cells can be redirected to the tumor site by fusing the CD1d to an anti-tumor antibody fragment.

Figure 5:
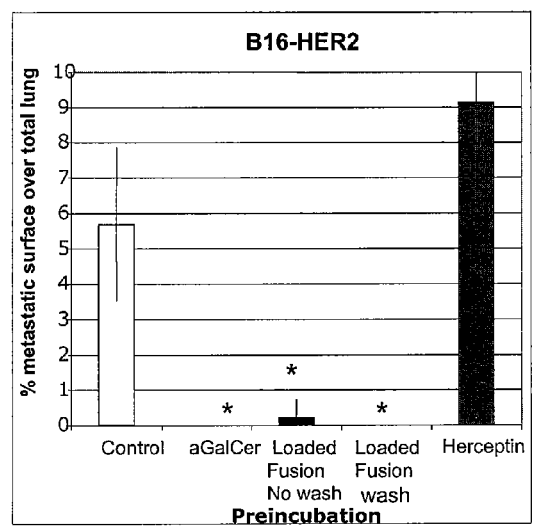
FIG. 5: Precoating experiment. B16-HER2 (a) and B16 wild type (B16 wt) cells (b) were precoated for 1 hour with 0.4 µg/ml αGalCer, 40 µg/ml αGalCer/CD1d-Her2 Fusion protein (Fusion), 10 µg/ml HERCEPTIN®, or 20 µg/ml αGalCer/sCD1d (sCD1d) and, with or without a previous wash, cells were injected i.v. Lung metastases were analyzed 3 weeks after graft with the ImageJ k-means clustering program and results are expressed as percentage of black metastatic surface over total lung surface. *P<0.005 compared to PBS control.
Figure 5:
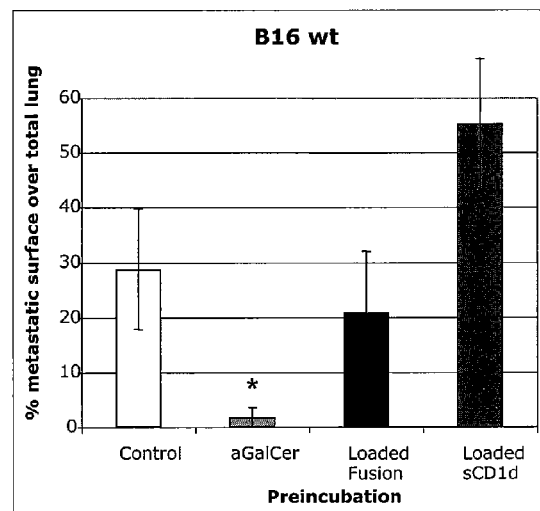

Precoating experiments: as a first approach to test the anti-tumor activity of the αGalCer/CD1d fused or not fused to the anti HER2 scFv, B16 melanoma cells, wild type or stably transfected with the human HER2 antigen, were pre-incubated with either (i) αGalCer alone; (ii) αGalCer/CD1d-anti HER2 fusion; (iii) αGalCer/sCD1d; or (iv) intact anti HER2 mAb (HERCEPTIN®), before being injected i.v. into naïve mice (FIG. 5*a,b*). As already reported Kawano, T. et al. *Science* 278:1626-1629 (1997), co-injection of αGalCer with tumor cells completely inhibited tumor development, whether the tumor cells expressed or did not express the HER2 antigen. This affect may be caused by a transient association of the αGalCer with the tumor cell surface, or by transient uptake of the free αGalCer. In contrast, the αGalCer/CD1d-anti HER2 fusion inhibited tumor metastases only when HER2 was expressed on the tumor cells. This effect was maintained even after several washings of the tumor cells, indicating that the anti tumor effect was due to specifically bound anti-HER2 fusion protein. Intact anti-HER2 mAb was unable to inhibit lung metastases of B16-HER2 tumor cells, supporting that the antitumor effect of the bound fusion protein was NKT cell mediated. Soluble αGalCer/sCD1d was also not able to block tumor growth of wild-type B16 melanoma cells confirming that recombinant CD1d molecules need to be bound to the tumor cells to block metastasis development. In these precoating settings, the anti tumor activity of the CD1d-anti HER2 was not superior to the already optimal effect of free αGalCer co-injected with tumor cells. However, the dependence on HER2 binding suggests that the CD1d-anti HER2 fusion can be efficiently targeted to HER2-expressing cancer cells and may redirect iNKT cells to the tumor site. In addition, these results demonstrate that the HER2-dependent anti tumor activity is due to the αGalCer/CD1d-anti HER2 per se and not to in vivo release of αGalCer.

Figure 6:
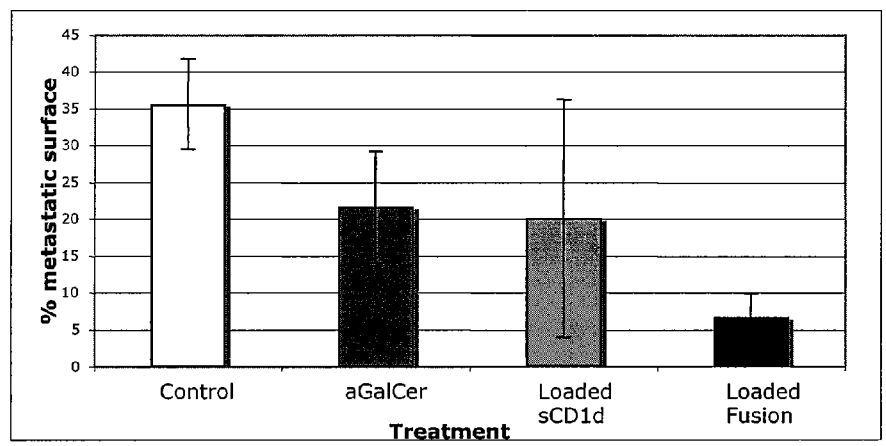
FIG. 6: In vivo anti tumor activity—Systemic Treatment. a Mice were grafted i.v. with 700.000 B16-HER2 cells and i.v. treatment was started 48 hours later. Mice were injected i.v. 5 times every 2 to 3 days with PBS (control), αGalCer (0.4 µg), αGalCer/sCD1d (sCD1d, 25 µg), or αGalCer/CD1d-anti-HER2 fusion (Fusion, 40 µg). Lung metastases were analysed after 3 weeks by the ImageJ k-means clustering program and expressed as percent metastatic surface over total lung surface. Treatment with αGalCer/CD1d-anti-HER2 fusion protein significantly inhibited the metastases formation. *P<0.005 versus control, *P<0.06 versus αGalCer b Treatment was started 6 days after graft. Mice were injected i.v. with 700,000 B16-HER2 cells and treatment with PBS (Control), αGalCer, or αGalCer/CD1d-anti-HER2 fusion protein (Fusion) was started 6 days after graft. Mice were treated 3× i.v. every 2-3 days and lung metastases were analyzed after 3 weeks as described above. Only treatment with the CD1d-anti HER2 fusion protein significantly reduced metastatic growth. *P<0.01 versus control.
Figure 6:
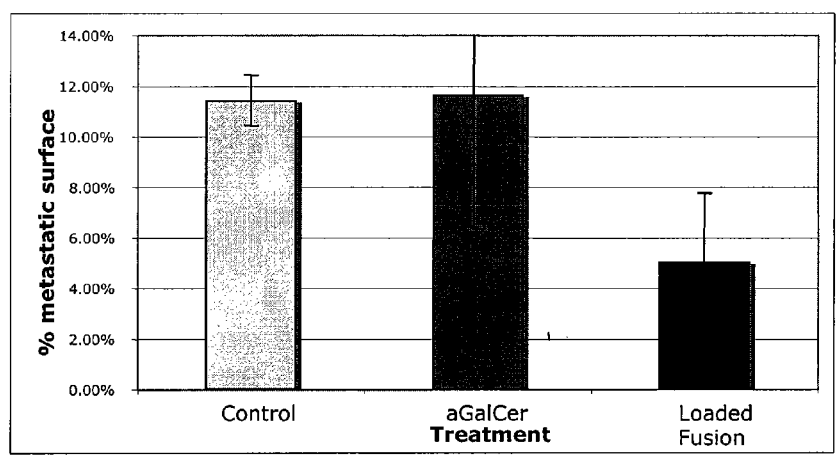

Systemic treatment: In view of the success obtained in precoating experiments, systemic treatments were started at different time points after the injection of B16-HER2 melanoma cells. FIG. 6*a* illustrates results obtained when treatment was initiated 48 hours after injecting B16-HER2 tumor cells. The mean of tumor metastasis in each group of five mice is expressed as the percentage of lung surface invaded by melanin-loaded nodules quantified as described in Materials and Methods. Free αGalCer administered in a series of 5 injections starting two days after tumor graft had no significant anti tumor effect. In contrast, αGalCer/CD1d-anti HER2 fusion protein administered on the same schedule had a potent anti metastatic effect with an average of 7% of the lungs invaded by melanin as compared with 35% in untreated animals (p<0.005). Even when treatment was started six days after injection of the tumor cells, the αGalCer/CD1d-anti HER2 fusion protein still had a significant anti tumor effect with 60% less metastasis than in untreated or free αGalCer-treated mice (p<0.01) (FIG. 6*b*). Interestingly, treatment with αGalCer/sCD1d had anti tumor activity which was very variable from mouse to mouse as shown by the large standard deviation (FIG. 6*a*). This in spite of the fact that the experiment of NKT TCR downmodulation did demonstrate that soluble αGalCer/sCD1d was functional to the same extent as the CD1d-anti HER2 fusion (FIG. 1).

Altogether, the efficient anti tumor activity obtained with the αGalCer/CD1d-anti HER2 fusion protein indicates that activated iNKT cells can be efficiently re-directed to the tumor site. Most importantly, these experiments again demonstrate that NKT cells can be repeatedly stimulated with αGalCer administered in association with CD1d, in this case, linked to anti-HER2 scFv, and also untargeted, as illustrated in Example 1.

Figure 7:
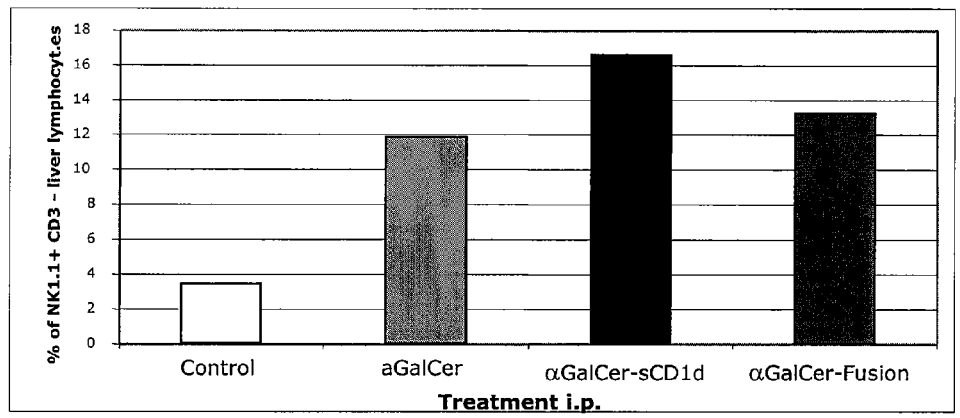
FIG. 7: Transactivation of NK, DCs and T cells by αGalCer/sCD1d or αGalCer/CD1d-anti-HER2 fusion protein activated iNKT cells. a Increase of liver NK cell numbers 20 hours after i.p. treatment with either PBS (control, white bar), 5 µg αGalCer (light grey bar), or 20 µg αGalCer-loaded sCD1d or 40 µg αGalCer/CD1d-anti-HER2 fusion protein (αGalCer-sCD1d, dark grey and αGalCer-Fusion, black bars, respectively). Cells were stained with anti NK1.1-PE and anti CD3-FITC and analysed by flow cytometry. NK cells are reported as NK1.1 positive/CD3 negative population. b c Induction of DC maturation and T cell proliferation by αGalCer/sCD1d activated NKT cells in vivo. Splenocytes were isolated after five treatments i.v. with either PBS (control), αGalCer, or αGalCer/sCD1d and cultured for 4 days with GM-CSF and then 3 more days with either PBS (control, white bars), αGalCer (grey bars), or αGalCer/sCD1d (sCD1d, black bars). Cells were then stained with anti CD11c-FITC and biotinylated anti CD40 and Streptavidin-PE to detect double positive mature DCs (c), or with anti NK1.1-PE and anti CD3-FITC to detect CD3 single positive T cells (d) by flow cytometry.
Figure 7:
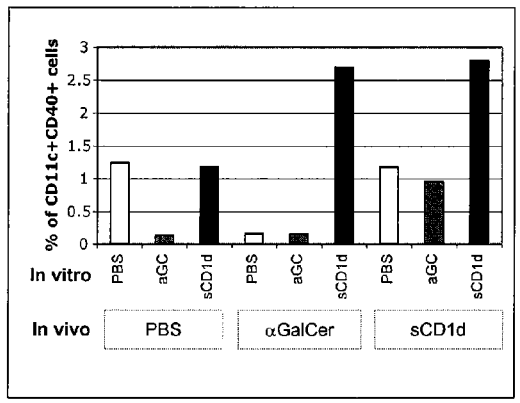
Figure 7:
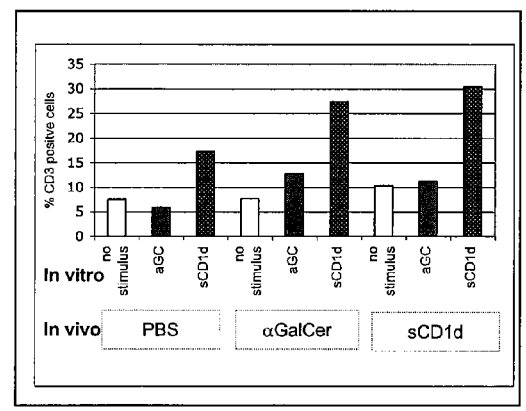

Example 3 iNKT Activated by Recombinant CD1d Molecules Retain their Capacity to Transactivate NK Cells, DC and T Lymphocytes In absence of a specific antigen: Several reports have described the capacity of iNKT cells to transactivate NK, DC and T cells upon activation with free αGalCer or αGalCer-pulsed dendritic cells (Nieda, M., et al. *Blood* 103:383-389 (2004); Hermans, I. F., et al. *J Immunol* 171:5140-5147 (2003); Smyth, M. J., et al. *J Exp Med* 201:1973-1985 (2005)). This Example demonstrates that these modulating properties of iNKT were retained upon their activation with recombinant αGalCer/sCD1d complexes. Regarding NK cells, their frequency indeed increased after a single injection of free αGalCer or of αGalCer/sCD1d with or without anti HER2, as shown by the increase of the NK1.1$^+$ CD3$^-$ cell population (FIG. 7*a*). Markers for DC maturation were also analyzed after 5 days in vitro culture of splenocytes isolated at the end of a systemic treatment, as described in Example 1. The percentage of CD11c$^+$ CD40$^+$ double positive cells was increased after in vitro stimulation with αGalCer/sCD1d indicating that activated iNKT cells promote DC maturation (FIG. 7*b*). This positive effect of αGalCer/sCD1d on DC in vitro was seen in splenocytes from αGalCer or αGalCer/sCD1d-treated mice, whereas αGalCer alone had no effect in any of the mice. The conventional T cell population of CD3$^+$ cells negative for CD1d tetramer and NK1.1, was analyzed in the same splenocytes cultures and it was significantly increased after in vitro stimulation by recombinant αGalCer/sCD1d complex while αGalCer alone had no significant effect (FIG. 7*c*). From 7% of total spleen cells without stimulation, percentage of CD3$^+$ cells increased to 17, 27 and 30%, respectively in naïve, αGalCer and αGalCer/sCD1d treated mice. In contrast, αGalCer alone had no significant effect in any of the mice (FIG. 7*c*).

Figure 8:
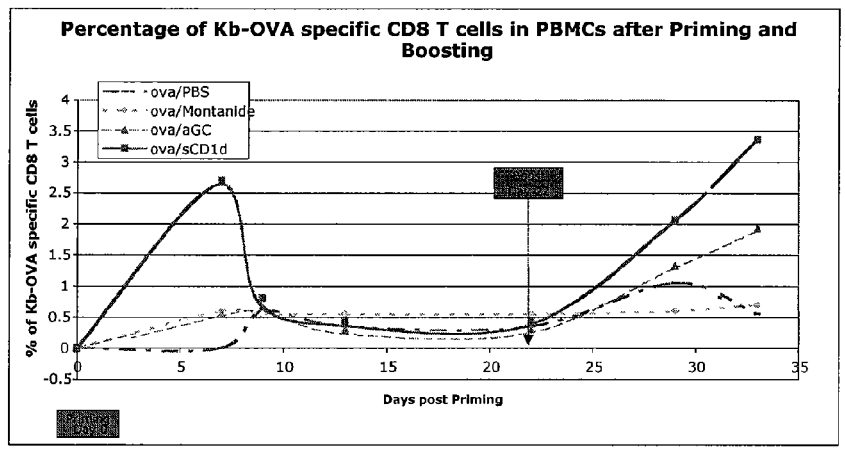
FIG. 8: αGalCer loaded sCD1d acts as a strong adjuvant for the expansion of antigen-specific T cells upon active immunization. a kinetics of expansion of H-2K$^b$/OVA specific CTLs. Mice were primed with 200 µg ovalbumin either as such (i.v.) or with MONTANIDE™ adjuvant (3:7 ratio, s.c.) or with 1 µg αGalCer or 20 µg αGalCer/sCD1d (i.v.). Mice were bled every 5-7 days and PBMC were stained with H-2K$^b$/oVA tetramer+anti-CD8. Results were expressed as tetramer+ and CD8+ NKT cells as a percentage of total CD8+ T cells. Mice were boosted with OVA peptide (20 µg) on day 22 employing the same adjuvants and route of injection as for primary immunization. b Ten days later, mice were sacrificed and splenocytes were cultured another five days either with no stimuli or with the same stimuli and adjuvants as for the in vivo boost. Frequency of OVA specific T cells was measured as in a. c The presence of mature DC in the same cultures as in b was analyzed by surface staining with anti CD11c and anti CD40 antibodies.
Figure 8:
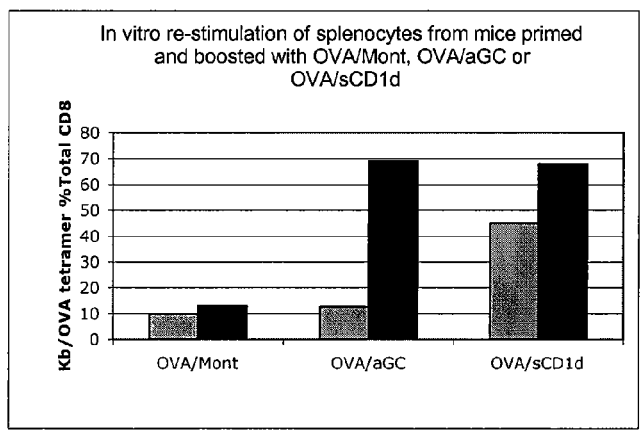
Figure 8:
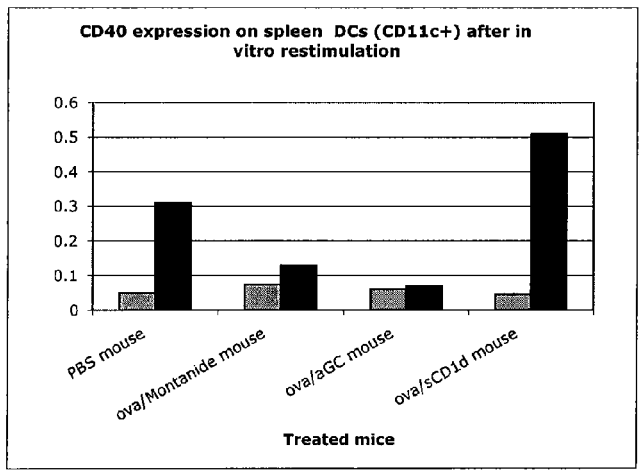

Together with active OVA immunization: An adjuvant effect has previously been attributed to free αGalCer and its potential use in vaccination has been proposed (Silk, J. D., et al. *J Clin Invest* 114:1800-1811 (2004)). The present data suggest that αGalCer/sCD1d would have superior adjuvant properties compared to free αGalCer. In this context, the adjuvant effect on the expansion of antigen-specific T cells in the model of C57 BL/6 mice immunized with ovalbumin was investigated (Hermans, I. F., et al. *J Immunol* 171:5140-5147 (2003)). After priming, specific H-2K$^b$/OVA$_{257-264}$ tetramer CD8 double positive T cells could be detected only in mice that received 200 μg ovalbumin together with αGalCer/sCD1d, whereas no H-2K$^b$/OVA$_{257-264}$ tetramer CD8 double positive T cells could be detected in mice primed with the same amount of antigen together with montanide or free αGalCer as adjuvant, (FIG. 8a). Furthermore, after boosting these same mice with OVA peptide in the same adjuvants in vivo and then 5 days in vitro culture without further stimulation, the frequency of K$^b$/OVA specific CTLs in the spleens reached up to 45% of total CD8 in mice that received a boost of OVA peptide with αGalCer/sCD1d, whereas the frequency was 12% in mice boosted with peptide and αGalCer alone (FIG. 8b). A further increase could be obtained by in vitro re-stimulation with the same respective stimuli and the frequency of specific T cells reached close to 70% in both αGalCer and αGalCer/sCD1d-treated mice (FIG. 8b). In the same cultures, there was also an increased frequency of mature DC following restimulation with αGalCer/sCD1d but not free αGalCer as shown by CD11c+CD40+ FACS staining (FIG. 8c)

The entire disclosure of all publications (including patents, patent applications, journal articles, laboratory manuals, books, or other documents) cited herein are hereby incorporated by reference.

What is claimed is:

1. A method of enhancing an immune response to a polypeptide immunogen in an animal, comprising administering to an animal in need thereof a composition comprising:
   (a) a polypeptide immunogen;
   (b) a nonspecific CD1d complex, said complex comprising:
      (i) a soluble CD1d polypeptide sufficient to associate with β2-microglobulin and bind a ceramide-like glycolipid antigen;
      (ii) a polypeptide comprising β2-microglobulin or a fragment thereof associated with said CD1d polypeptide;
      (iii) a ceramide-like glycolipid antigen bound to said CD1d polypeptide, wherein said ceramide-like glycolipid antigen has an α-linked galactose or glucose and is capable of activating NKT cells; and
   (c) a carrier;
   wherein said CD1d complex is administered in an amount sufficient to enhance the immune response against said polypeptide immunogen relative to administration of said polypeptide immunogen in the absence of said CD1d complex.

2. The method of claim 1, wherein said composition additionally comprises an adjuvant.

3. The method of claim 1, wherein said ceramide-like glycolipid antigen comprises an α-galactosylceramide.

4. The method of claim 2, wherein said adjuvant is a Toll-like receptor (TLR) agonist selected from the group consisting of: monophosphoryl lipid A (MPL), CpG, and BCG.

5. The method of claim 4, wherein said adjuvant is MPL.

6. The method of claim 1, wherein said soluble CD1d polypeptide comprises an amino acid sequence at least 90% identical to amino acids 21 to 295 of SEQ ID NO: 1.

7. The method of claim 6, wherein said soluble CD1d polypeptide comprises an amino acid sequence at least 95% identical to amino acids 21 to 295 of SEQ ID NO: 1.

8. The method of claim 7, wherein said soluble CD1d polypeptide comprises amino acids 21 to 295 of SEQ ID NO: 1.

9. The method of claim 7, wherein said soluble CD1d polypeptide comprises amino acids 1 to 295 of SEQ ID NO: 1.

10. The method of claim 1, wherein said soluble CD1d polypeptide comprises amino acids 20 to 295 of SEQ ID NO: 1, except for at least one but less than 10 conservative amino acid substitutions.

11. The method of claim 1, wherein said soluble CD1d polypeptide further comprises a heterologous polypeptide.

12. The method of claim 1, wherein said β2-microglobulin polypeptide comprises an amino acid sequence at least 90% identical to amino acids 21 to 113 of SEQ ID NO: 2.

13. The method of claim 1, wherein said β2-microglobulin polypeptide comprises amino acids 21 to 113 of SEQ ID NO: 2.

14. The method of claim 1, wherein said β2-microglobulin polypeptide comprises amino acids 1 to 119 of SEQ ID NO: 2.

15. The method of claim 3, wherein said α-galactosylceramide comprises the formula:

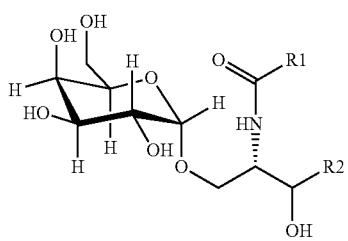

Formula I wherein
R1 is a linear or branched $C_2$-$C_{27}$ alkene with at least one C=C bond but not —$(CH_2)_7$CH=CH$(CH_2)_7$CH$_3$, or R1 is C(OH) R3 wherein R3 is a linear or branched $C_2$-$C_{26}$ alkene with at least one C=C bond; and
R2 is one of the following (a)-(e):
(a) —$CH_2(CH_2)_x$CH$_3$,
(b) —CH(OH)$(CH_2)_x$CH$_3$,
(c) —CH(OH)$(CH_2)_x$(CH)(CH$_3$)$_2$,
(d) —CH=CH$(CH_2)_x$CH$_3$, and
(e) —CH(OH)$(CH_2)_x$CH(CH$_3$)CH$_2$CH$_3$,
wherein X is an integer ranging from 5-17.

16. The method of claim 1, wherein said composition further comprises a costimulatory molecule.

17. The method of claim 16, wherein said costimulatory molecule is B71.

18. A method of enhancing an immune response to a polypeptide immunogen in an animal and inhibiting an anergic effect of a ceramide-like glycolipid antigen on NKT cell activity, said method comprising:
(a) administering to an animal in need thereof a composition comprising:
(i) a polypeptide immunogen;
(ii) a nonspecific CD1d complex, said complex comprising:
(1) a soluble CD1d polypeptide sufficient to associate with β2microglobulin and bind a ceramide-like glycolipid antigen; and
(2) a polypeptide comprising β2-microglobulin or a fragment thereof associated with said CD1d polypeptide;
(3) a ceramide-like glycolipid antigen bound to said CD1d polypeptide, wherein said ceramide-like glycolipid antigen has an α-linked galactose or glucose and is capable of activating NKT cells; and
(iii) a carrier;
wherein said CD1d complex is administered in an amount sufficient to enhance the immune response against said polypeptide immunogen relative to administration of said polypeptide immunogen in the absence of said CD1d complex; and
(b) readministering said composition to said animal one or more times, wherein said NKT cells are activated in response to readministration of said composition.

* * * * *

```
SEQUENCE LISTING

<160> NUMBER OF SEQ ID NOS: 20

<210> SEQ ID NO 1
<211> LENGTH: 335
<212> TYPE: PRT
<213> ORGANISM: Homo sapiens

<400> SEQUENCE: 1

Met Gly Cys Leu Leu Phe Leu Leu Leu Trp Ala Leu Leu Gln Ala Trp
1               5                   10                  15

Gly Ser Ala Glu Val Pro Gln Arg Leu Phe Pro Leu Arg Cys Leu Gln
            20                  25                  30

Ile Ser Ser Phe Ala Asn Ser Ser Trp Thr Arg Thr Asp Gly Leu Ala
        35                  40                  45

Trp Leu Gly Glu Leu Gln Thr His Ser Trp Ser Asn Asp Ser Asp Thr
    50                  55                  60

Val Arg Ser Leu Lys Pro Trp Ser Gln Gly Thr Phe Ser Asp Gln Gln
65                  70                  75                  80

Trp Glu Thr Leu Gln His Ile Phe Arg Val Tyr Arg Ser Ser Phe Thr
                85                  90                  95

Arg Asp Val Lys Glu Phe Ala Lys Met Leu Arg Leu Ser Tyr Pro Leu
            100                 105                 110

Glu Leu Gln Val Ser Ala Gly Cys Glu Val His Pro Gly Asn Ala Ser
        115                 120                 125

Asn Asn Phe Phe His Val Ala Phe Gln Gly Lys Asp Ile Leu Ser Phe
    130                 135                 140

Gln Gly Thr Ser Trp Glu Pro Thr Gln Glu Ala Pro Leu Trp Val Asn
145                 150                 155                 160

Leu Ala Ile Gln Val Leu Asn Gln Asp Lys Trp Thr Arg Glu Thr Val
                165                 170                 175

Gln Trp Leu Leu Asn Gly Thr Cys Pro Gln Phe Val Ser Gly Leu Leu
            180                 185                 190

Glu Ser Gly Lys Ser Glu Leu Lys Lys Gln Val Lys Pro Lys Ala Trp
        195                 200                 205

Leu Ser Arg Gly Pro Ser Pro Gly Pro Gly Arg Leu Leu Leu Val Cys
    210                 215                 220

His Val Ser Gly Phe Tyr Pro Lys Pro Val Trp Val Lys Trp Met Arg
225                 230                 235                 240

Gly Glu Gln Glu Gln Gln Gly Thr Gln Pro Gly Asp Ile Leu Pro Asn
                245                 250                 255
```

```
Ala Asp Glu Thr Trp Tyr Leu Arg Ala Thr Leu Asp Val Val Ala Gly
            260                 265                 270

Glu Ala Ala Gly Leu Ser Cys Arg Val Lys His Ser Ser Leu Glu Gly
        275                 280                 285

Gln Asp Ile Val Leu Tyr Trp Gly Gly Ser Tyr Thr Ser Met Gly Leu
    290                 295                 300

Ile Ala Leu Ala Val Leu Ala Cys Leu Leu Phe Leu Leu Ile Val Gly
305                 310                 315                 320

Phe Thr Ser Arg Phe Lys Arg Gln Thr Ser Tyr Gln Gly Val Leu
                325                 330                 335

<210> SEQ ID NO 2
<211> LENGTH: 119
<212> TYPE: PRT
<213> ORGANISM: Homo sapiens

<400> SEQUENCE: 2

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 3
<211> LENGTH: 15
<212> TYPE: PRT
<213> ORGANISM: Artificial Sequence
<220> FEATURE:
<223> OTHER INFORMATION: Synthetic linker

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synethetic linker

<400> SEQUENCE: 4

Gly Gly Gly Gly Ser Gly Gly Gly Gly Ser Gly Gly Gly Ala Ser
1               5                   10                  15

<210> SEQ ID NO 5
<211> LENGTH: 8
<212> TYPE: PRT
<213> ORGANISM: Artificial Sequence
<220> FEATURE:
```

<223> OTHER INFORMATION: Synthetic FLAG

<400> SEQUENCE: 5

Asp Tyr Lys Asp Asp Asp Asp Lys
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic FLAG

<400> SEQUENCE: 6

Asp Tyr Lys Asp Glu Asp Asp Lys
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic STREP

<400> SEQUENCE: 7

Ala Trp Arg His Pro Gln Phe Gly Gly
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic VSV-G

<400> SEQUENCE: 8

Tyr Thr Asp Ile Glu Met Asn Arg Leu Gly Lys
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Synthetic poly-His

<400> SEQUENCE: 9

His His His His His His
1               5

<210> SEQ ID NO 10
<211> LENGTH: 13
<212> TYPE: PRT
<213> ORGANISM: Influenza virus

<400> SEQUENCE: 10

Tyr Pro Tyr Asp Val Pro Asp Tyr Ala Ile Glu Gly Arg
1               5                   10

<210> SEQ ID NO 11
<211> LENGTH: 11
<212> TYPE: PRT
<213> ORGANISM: Homo sapiens

<400> SEQUENCE: 11

Glu Gln Lys Leu Leu Ser Glu Glu Asp Leu Asn

<210> SEQ ID NO 12
<211> LENGTH: 13
<212> TYPE: PRT
<213> ORGANISM: Artificial Sequence
<220> FEATURE:
<223> OTHER INFORMATION: Synthetic linker

<400> SEQUENCE: 12

Gly Gly Gly Gly Ser Gly Gly Ser Gly Ser Gly Gly Gly
1               5                   10

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
ttaagcttat ggctcgctcg gtga                                              24

<210> SEQ ID NO 14
<211> LENGTH: 73
<212> TYPE: DNA
<213> ORGANISM: Artificial Sequence
<220> FEATURE:
<223> OTHER INFORMATION: Synthetic primer

<400> SEQUENCE: 14
aagatatcgc tagctccacc tccagaaccg gatccacctg atccacctcc acccatgtct      60
cgatcccagt aga                                                          73

<210> SEQ ID NO 15
<211> LENGTH: 6
<212> TYPE: PRT
<213> ORGANISM: Artificial Sequence
<220> FEATURE:
<223> OTHER INFORMATION: Synthetic linker

<400> SEQUENCE: 15

Ser Ser Gly Ser Gly Gly
1               5

<210> SEQ ID NO 16
<211> LENGTH: 35
<212> TYPE: DNA
<213> ORGANISM: Artificial Sequence
<220> FEATURE:
<223> OTHER INFORMATION: Synthetic primer

<400> SEQUENCE: 16
ttctcgaggc tagccagcaa aagaattaca ccttc                                  35

<210> SEQ ID NO 17
<211> LENGTH: 76
<212> TYPE: DNA
<213> ORGANISM: Artificial Sequence
<220> FEATURE:
<223> OTHER INFORMATION: Synthetic primer

<400> SEQUENCE: 17
ttgaattcgg cgcctccacc tccagaaccg gatccacctg atccacctcc accgcccacg      60
ggtgcttgcc tggcat                                                       76

```
<210> SEQ ID NO 18
<211> LENGTH: 6
<212> TYPE: PRT
<213> ORGANISM: Artificial Sequence
<220> FEATURE:
<223> OTHER INFORMATION: Synthetic linker

<400> SEQUENCE: 18

Ser Ser Gly Ser Gly Gly
1               5

<210> SEQ ID NO 19
<211> LENGTH: 34
<212> TYPE: DNA
<213> ORGANISM: Artificial Sequence
<220> FEATURE:
<223> OTHER INFORMATION: Synthetic primer

<400> SEQUENCE: 19
ttctcgaggg cgccgactac aaagatatcg ttat                              34

<210> SEQ ID NO 20
<211> LENGTH: 65
<212> TYPE: DNA
<213> ORGANISM: Artificial Sequence
<220> FEATURE:
<223> OTHER INFORMATION: Synthetic primer

<400> SEQUENCE: 20
aagcggccgc ttaatggtgg tgatgatgat gtcctccaga accagaagaa acggtaacgg  60
tggta                                                             65
```